(12) United States Patent
Baba et al.

(10) Patent No.: US 12,381,011 B2
(45) Date of Patent: Aug. 5, 2025

(54) INFORMATION PROCESSING APPARATUS AND NON-TRANSITORY COMPUTER READABLE MEDIUM

(71) Applicant: Agama-X Co., Ltd., Tokyo (JP)

(72) Inventors: Motofumi Baba, Kanagawa (JP); Masahiro Sato, Kanagawa (JP); Kengo Tokuchi, Kanagawa (JP); Kiichiro Arikawa, Kanagawa (JP); Monta Ido, Kanagawa (JP); Kosuke Aoki, Kanagawa (JP); Tadashi Suto, Kanagawa (JP); Tsutomu Kimura, Kanagawa (JP); Hanako Kariya, Kanagawa (JP)

(73) Assignee: Agama-X Co., Ltd., Tokyo (JP)

( * ) Notice: Subject to any disclaimer, the term of this patent is extended or adjusted under 35 U.S.C. 154(b) by 0 days.

(21) Appl. No.: 18/731,416

(22) Filed: Jun. 3, 2024

(65) Prior Publication Data

US 2024/0321462 A1    Sep. 26, 2024

Related U.S. Application Data

(63) Continuation of application No. 18/232,356, filed on Aug. 10, 2023, now Pat. No. 12,033,758, which is a
(Continued)

(30) Foreign Application Priority Data

Oct. 1, 2020   (JP) .............................. JP2020-166688

(51) Int. Cl.
*G16H 50/30*    (2018.01)
*G06N 5/022*    (2023.01)
*G16H 50/70*    (2018.01)

(52) U.S. Cl.
CPC ............. *G16H 50/30* (2018.01); *G06N 5/022* (2013.01); *G16H 50/70* (2018.01)

(58) Field of Classification Search
CPC .......... G06N 5/04; G06N 5/022; G06N 20/00; G16H 50/20; G16H 50/30; G16H 30/40; G16H 40/40; G16H 20/70; G16H 50/70
See application file for complete search history.

(56) References Cited

U.S. PATENT DOCUMENTS 8,798,736 B2   8/2014   Sullivan et al.
9,582,080 B1   2/2017   Tilton et al.
(Continued)

FOREIGN PATENT DOCUMENTS

AU   2005321925   7/2006
CA      288597    4/2014
(Continued)

OTHER PUBLICATIONS

European Search Report and the European Search Opinion Dated Jun. 16, 2021 From the European Patent Office Re. Application No. 20216789.6.
(Continued)

*Primary Examiner* — Vinh T Lam

(57) ABSTRACT

An information processing apparatus includes a processor configured to acquire biological information of plural users determined to be within a predetermined area and operate an apparatus based on the biological information of the plural users.

4 Claims, 33 Drawing Sheets

Related U.S. Application Data continuation of application No. 17/707,999, filed on Mar. 30, 2022, now Pat. No. 11,769,595, which is a continuation-in-part of application No. 17/131,683, filed on Dec. 22, 2020, now Pat. No. 11,635,816.

(56) References Cited

U.S. PATENT DOCUMENTS

| | | | |
|---|---|---|---|
| 9,949,714 B2 | 4/2018 | Wu et al. | |
| 9,953,453 B2 | 4/2018 | Lynn et al. | |
| 10,271,783 B2* | 4/2019 | Yamada | A61B 5/369 |
| 10,311,373 B2 | 6/2019 | Rapaka et al. | |
| 10,319,477 B1* | 6/2019 | Bill | G01N 33/92 |
| 10,452,982 B2* | 10/2019 | Ichiboshi | G06N 5/04 |
| 10,453,015 B2 | 10/2019 | Chandra et al. | |
| 10,492,684 B2 | 12/2019 | Khachaturian et al. | |
| 10,506,926 B2 | 12/2019 | Khachaturian et al. | |
| 10,593,426 B2* | 3/2020 | Amarasingham | G16H 50/50 |
| 10,602,987 B2 | 3/2020 | Khachaturian et al. | |
| 10,667,738 B2 | 6/2020 | Arai et al. | |
| 10,712,820 B2* | 7/2020 | Artemiadis | G06N 7/01 |
| 10,786,207 B2 | 9/2020 | Arai et al. | |
| 10,842,431 B2 | 11/2020 | Arai et al. | |
| 10,847,049 B2* | 11/2020 | Chuang | A61B 5/14551 |
| 10,856,092 B2* | 12/2020 | Goldstein | G16H 20/10 |
| 10,937,334 B2* | 3/2021 | Ryuzaki | G10L 15/22 |
| 10,960,225 B2 | 3/2021 | Adaikkan et al. | |
| 10,987,014 B2* | 4/2021 | Aoki | G16H 50/20 |
| 10,987,042 B2* | 4/2021 | Kawai | H04N 9/3194 |
| 11,020,202 B2* | 6/2021 | Wada | G06T 17/20 |
| 11,090,000 B2* | 8/2021 | Nishiyama | A61B 5/7275 |
| 11,116,440 B2 | 9/2021 | Prat et al. | |
| 11,231,779 B1* | 1/2022 | Sundberg | G06F 3/016 |
| 11,273,283 B2* | 3/2022 | Poltorak | G16H 20/70 |
| 11,315,033 B2 | 4/2022 | Lei et al. | |
| 11,357,443 B2 | 6/2022 | Arai et al. | |
| 11,382,561 B2 | 7/2022 | Vu et al. | |
| 11,412,974 B2 | 8/2022 | Tokuchi et al. | |
| 11,452,839 B2 | 9/2022 | Poltorak | |
| 11,478,603 B2 | 10/2022 | Poltorak | |
| 11,490,842 B2* | 11/2022 | Nishiyama | G01N 33/497 |
| 11,636,392 B2 | 4/2023 | Sato et al. | |
| 11,687,800 B2* | 6/2023 | Bonutti | G08B 31/00 706/11 |
| 11,741,357 B2* | 8/2023 | Zhang | G16H 50/20 706/25 |
| 11,751,770 B2 | 9/2023 | Brown et al. | |
| 11,779,811 B2* | 10/2023 | Kwatra | A63B 24/0075 482/9 |
| 11,963,802 B2* | 4/2024 | Sato | A61B 5/7235 |
| 12,033,761 B2* | 7/2024 | Foschini | G06N 20/00 |
| 12,073,933 B2* | 8/2024 | Levy | G16H 20/70 |
| 2006/0173663 A1* | 8/2006 | Langheier | G16H 50/20 703/11 |
| 2009/0177068 A1* | 7/2009 | Stivoric | A61B 5/0022 600/365 |
| 2011/0263946 A1* | 10/2011 | El Kaliouby | A61B 5/16 600/300 |
| 2015/0248615 A1 | 9/2015 | Parra et al. | |
| 2015/0351655 A1 | 12/2015 | Coleman | |
| 2016/0063874 A1* | 3/2016 | Czerwinski | G16H 50/20 434/236 |
| 2016/0367183 A1* | 12/2016 | Miyasaka | A61B 5/486 |
| 2017/0102783 A1 | 4/2017 | Shikii et al. | |
| 2017/0323220 A1* | 11/2017 | Gordon | G06N 20/00 |
| 2018/0004742 A1 | 1/2018 | Nakata et al. | |
| 2018/0121784 A1* | 5/2018 | Ichiboshi | G16H 10/20 |
| 2018/0344213 A1* | 12/2018 | Ota | G16H 10/60 |
| 2018/0374211 A1* | 12/2018 | Kurata | A61B 5/0082 |
| 2019/0046056 A1 | 2/2019 | Khachaturian et al. | |
| 2019/0117085 A1 | 4/2019 | Brown et al. | |
| 2019/0231211 A1* | 8/2019 | Tokuchi | A61B 5/7296 |
| 2019/0247662 A1 | 8/2019 | Poltroak | |
| 2019/0258818 A1 | 8/2019 | Yu et al. | |
| 2020/0034739 A1* | 1/2020 | Chung | G16H 40/63 |
| 2020/0035337 A1* | 1/2020 | Söhne | A61B 5/0022 |
| 2020/0077892 A1 | 3/2020 | Tran | |
| 2020/0113503 A1 | 4/2020 | Kim et al. | |
| 2020/0237307 A1 | 7/2020 | Sato et al. | |
| 2020/0301998 A1 | 9/2020 | Takenouchi et al. | |
| 2020/0311587 A1 | 10/2020 | Tsunoda et al. | |
| 2021/0041953 A1 | 2/2021 | Poltorak | |
| 2021/0063977 A1* | 3/2021 | Sato | G16H 50/20 |
| 2021/0098117 A1* | 4/2021 | Hartley | G06Q 30/0284 |
| 2021/0173484 A1 | 6/2021 | Sato et al. | |
| 2021/0174251 A1 | 6/2021 | Sato et al. | |
| 2021/0177325 A1 | 6/2021 | Tokuchi et al. | |
| 2021/0181843 A1 | 6/2021 | Tokuchi et al. | |
| 2021/0247843 A1 | 8/2021 | Lee et al. | |
| 2021/0272696 A1 | 9/2021 | DeMazumder | |
| 2021/0282721 A1 | 9/2021 | Ogasawara et al. | |
| 2022/0023584 A1 | 1/2022 | Lee et al. | |
| 2022/0107686 A1 | 4/2022 | Baba et al. | |
| 2022/0223294 A1 | 7/2022 | Baba et al. | |
| 2022/0236236 A1* | 7/2022 | Arora | G01N 33/483 |
| 2022/0319536 A1 | 10/2022 | Lee | |
| 2022/0400996 A1* | 12/2022 | Kitade | A61B 5/7278 |
| 2023/0386674 A1 | 11/2023 | Baba et al. | |

FOREIGN PATENT DOCUMENTS

| | | |
|---|---|---|
| CN | 106562793 | 4/2017 |
| CN | 109922417 | 6/2019 |
| EP | 3085305 | 10/2016 |
| EP | 3181043 | 6/2017 |
| JP | 2002-166050 | 6/2002 |
| JP | 2014-071825 | 4/2014 |
| JP | 2015-102650 | 6/2015 |
| JP | 2015-211705 | 11/2015 |
| JP | 2016-067922 | 5/2016 |
| JP | 2016-177422 | 10/2016 |
| JP | 2016-217583 | 12/2016 |
| JP | 6067808 | 1/2017 |
| JP | 2021-033678 | 3/2021 |
| JP | 2021-090668 | 6/2021 |
| WO | WO 2014/059234 | 4/2014 |
| WO | WO 2017/102416 | 6/2017 |
| WO | WO 2018/067761 | 4/2018 |
| WO | WO 2020/039206 | 2/2020 |
| WO | WO 2020/251135 | 12/2020 |

OTHER PUBLICATIONS

Interview Summary Dated Oct. 28, 2022 from the US Patent and Trademark Office Re. U.S. Appl. No. 17/131,683. (2 pages).
Notice of Allowance Dated May 11, 2023 From the US Patent and Trademark Office Re. U.S. Appl. No. 17/707,999. (8 Pages).
Notice of Allowance Dated Dec. 12, 2022 from the US Patent and Trademark Office Re. U.S. Appl. No. 17/131,683. (9 pages).
Notice of Allowance Dated Mar. 13, 2024 from the US Patent and Trademark Office Re. U.S. Appl. No. 18/232,356. (14 pages).
Official Action Dated Aug. 5, 2022 from US Patent and Trademark Office Re. U.S. Appl. No. 17/131,683. (14 pages).
Official Action Dated Apr. 27, 2022 from US Patent and Trademark Office Re. U.S. Appl. No. 17/131,683. (18 pages).
Official Action Dated Jan. 31, 2023 from the US Patent and Trademark Office Re. U.S. Appl. No. 17/707,999. (18 pages).
Unknown "Theta Wave Contributes to 'Giving Up': Possibility of Effecting Cognitive Activity via Brain Wave Rhythmic Control", Retrieved from Internet: 1-3, Mar. 24, 2022 with English Summary.

* cited by examiner

FIG. 4

| ID | REFERENCE BRAIN WAVES | OPERATION INFORMATION |
|---|---|---|
| 1 | ⌒ | START COOLING FUNCTION OF AIR CONDITIONER |
| 2 | ⌒ | STOP COOLING FUNCTION OF AIR CONDITIONER |
| ... | ... | ... |

FIG. 5

| ID | REFERENCE BRAIN WAVES | OPERATION INFORMATION | USER INFORMATION |
|---|---|---|---|
| 1 | ⌒ | START COOLING FUNCTION OF AIR CONDITIONER | USER A |
| 2 | ⌒ | START COOLING FUNCTION OF AIR CONDITIONER | USER B |
| 3 | ⌒ | STOP COOLING FUNCTION OF AIR CONDITIONER | USER A |
| ... | ... | ... | ... |

FIG. 6

| ID | REFERENCE BRAIN WAVES | REFERENCE BODY TEMPERATURE | OPERATION INFORMATION | USER INFORMATION |
|---|---|---|---|---|
| 1 |  | HIGHER THAN OR EQUAL TO THRESHOLD | START COOLING FUNCTION OF AIR CONDITIONER | USER A |
| 2 |  | HIGHER THAN OR EQUAL TO THRESHOLD | START COOLING FUNCTION OF AIR CONDITIONER | USER B |
| 3 |  | LOWER THAN THRESHOLD | STOP COOLING FUNCTION OF AIR CONDITIONER | USER A |
| ... | ... | ... | ... | ... |

FIG. 7

| ID | REFERENCE BRAIN WAVES | REFERENCE ENVIRONMENT INFORMATION | OPERATION INFORMATION | USER INFORMATION |
|---|---|---|---|---|
| 1 |  | ROOM TEMPERATURE: HIGHER THAN OR EQUAL TO THRESHOLD | START COOLING FUNCTION OF AIR CONDITIONER | USER A |
| 2 |  | ROOM TEMPERATURE: HIGHER THAN OR EQUAL TO THRESHOLD | START COOLING FUNCTION OF AIR CONDITIONER | USER B |
| 3 |  | ROOM TEMPERATURE: LOWER THAN THRESHOLD | STOP COOLING FUNCTION OF AIR CONDITIONER | USER A |
| ... | ... | ... | ... | ... |

INFORMATION PROCESSING APPARATUS AND NON-TRANSITORY COMPUTER READABLE MEDIUM

RELATED APPLICATIONS

This application is a Continuation of U.S. patent application Ser. No. 18/232,356 filed Aug. 10, 2023, which is a Continuation of U.S. patent application Ser. No. 17/707,999 filed on Mar. 30, 2022, which is a Continuation-in-Part (CIP) of U.S. patent application Ser. No. 17/131,683 filed on Dec. 22, 2020, which claims the benefit of priority of Japanese Patent Application No. 2020-166688 filed on Oct. 1, 2020. The contents of the above applications are all incorporated by reference as if fully set forth herein in their entirety.

FIELD AND BACKGROUND OF THE INVENTION

(i) Technical Field

The present disclosure relates to an information processing apparatus and a non-transitory computer readable medium.

(ii) Related Art

It is possible that operation targets are operated using biological information such as brain waves.

In Japanese Unexamined Patent Application Publication No. 2014-071825, a brain-machine interface (BMI) apparatus that employs steady state visually evoked potential (SSVEP) is described.

In Japanese Unexamined Patent Application Publication No. 2015-211705, a BMI motion assistance apparatus that detects a brain wave biological signal from a user's brain waves, that detects a surface myoelectric potential signal from the user's surface myoelectric potential, and that obtains a control signal on the basis of these biological signals is described.

In Japanese Unexamined Patent Application Publication No. 2015-102650, an imaging control apparatus that stores in advance brain wave conditions, which are conditions of brain waves caused when certain physical motions are imagined, that obtains brain wave information, and that, if brain waves included in the obtained brain wave information satisfy one of the stored brain wave conditions, outputs an imaging condition, which is a condition at a time when an imaging apparatus captures an image of a subject, to the imaging apparatus is described.

In Japanese Unexamined Patent Application Publication No. 2002-166050, a method for matching a brain wave signal and a person's intention is described.

SUMMARY OF THE INVENTION

Aspects of non-limiting embodiments of the present disclosure relate to an operation of an operation target based on biological information regarding plural users.

Aspects of certain non-limiting embodiments of the present disclosure address the above advantages and/or other advantages not described above. However, aspects of the non-limiting embodiments are not required to address the advantages described above, and aspects of the non-limiting embodiments of the present disclosure may not address advantages described above.

According to an aspect of the present disclosure, there is provided an information processing apparatus including a processor configured to acquire biological information of plural users determined to be within a predetermined area and operate an apparatus based on the biological information of the plural users.

BRIEF DESCRIPTION OF THE SEVERAL VIEWS OF THE DRAWINGS

An exemplary embodiment of the present disclosure will be described in detail based on the following figures, wherein:

FIG. 4 is a diagram illustrating a management table;

FIG. 5 is a diagram illustrating the management table;

FIG. 6 is a diagram illustrating the management table;

FIG. 7 is a diagram illustrating the management table;

DESCRIPTION OF SPECIFIC EMBODIMENTS
OF THE INVENTION

Figure 1:
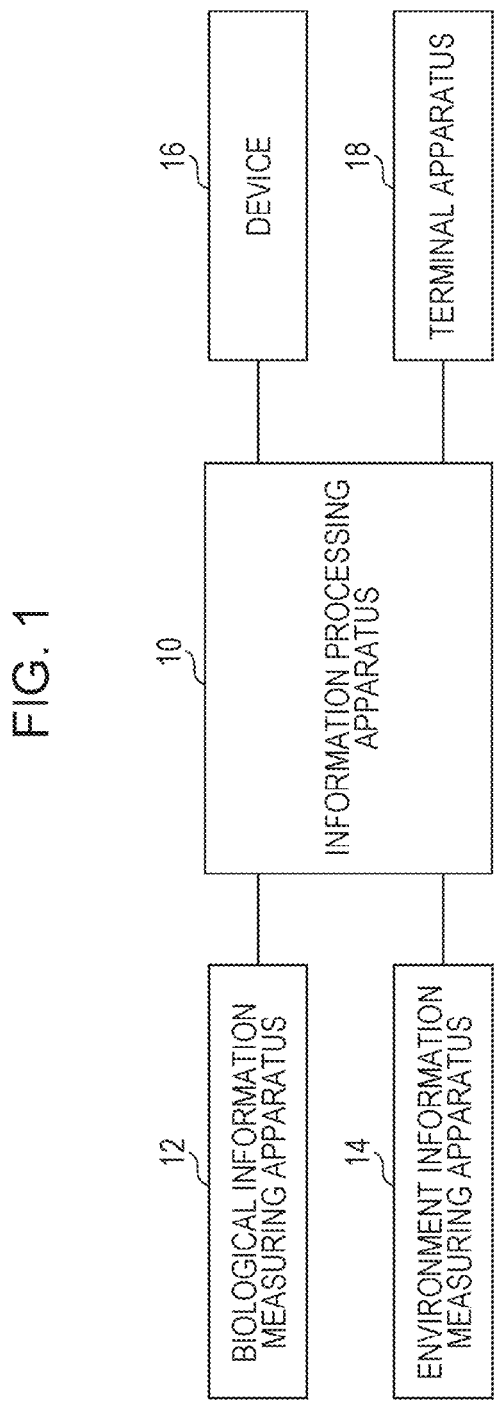
FIG. 1 is a block diagram illustrating the configuration of an information processing system according to an exemplary embodiment.

An information processing system according to an exemplary embodiment will be described with reference to FIG. 1. FIG. 1 illustrates an example of the configuration of the information processing system according to the present exemplary embodiment.

The information processing system according to the present exemplary embodiment includes an information processing apparatus 10, at least one biological information measuring apparatus 12, at least one environment information measuring apparatus 14, at least one device 16, and at least one terminal apparatus 18. The number of apparatuses illustrated in FIG. 1 is just an example, and the number of apparatuses used is not limited to that illustrated in FIG. 1. The information processing system may also include apparatuses (e.g., an external apparatus such as a server) other than those illustrated in FIG. 1. When the device 16 is not used, the device 16 need not be included in the information processing system. When the terminal apparatus 18 is not used, the terminal apparatus 18 need not be included in the information processing system.

The apparatuses included in the information processing system are each configured to communicate with the other apparatuses. The communication may be wired communication employing cable or wireless communication. That is, the apparatuses may be physically connected to one another by cable and communicate information with one another or communicate information with one another through wireless communication. Short-distance wireless communication or Wi-Fi (registered trademark), for example, is used for the wireless communication. Wireless communication based on another standard may be used, instead. Bluetooth (registered trademark), radio-frequency identification (RFID), or near-field communication (NFC), for example, may be used as the short distance wireless communication. The apparatuses may communicate with one another through a communication path such as a local-area network (LAN) or the Internet.

The information processing apparatus 10 is, for example, a personal computer (PC), a tablet PC, a smartphone, a mobile phone, or another apparatus (e.g., a server, a robot, etc.). The information processing apparatus 10 may be a terminal apparatus carriable by a person (e.g., a tablet PC, a smartphone, a mobile phone, etc.), an apparatus set on a table or the like for use, a mobile apparatus (e.g., a self-propelled apparatus), an apparatus that performs operations, or an apparatus capable of making conversations with persons. For example, the information processing apparatus 10 may be a smart speaker having a communication function and including a microphone and a speaker or a robot that makes conversations with persons and that performs operations. The information processing apparatus 10 may be an apparatus provided with artificial intelligence (AI).

The biological information measuring apparatus 12 is configured to measure biological information regarding living things. The living things may be persons, animals other than persons, or plants.

For example, the biological information measuring apparatuses 12 include various sensors and electrodes and measures biological information regarding a living thing. When plural biological information measuring apparatuses 12 are used, the biological information measuring apparatuses 12 may measure biological information of different types. Some or all of the biological information measuring apparatuses 12 may measure biological information of the same type. The biological information measuring apparatus 12 may measure biological information of a single type or plural types.

Biological information may include various pieces of information exhibited by a living thing. The biological information is, for example, information indicating brain activity (e.g., brain waves, cerebral blood flow, brain magnetic field signals, etc.), information indicating pulse rate, myoelectric information such as a myoelectric waveform, information regarding saliva (e.g., information indicating saliva volume), information indicating a pulse wave, information indicating blood pressure, information indicating blood flow, information indicating pulse, information indicating heart rate, information indicating an electrocardiographic waveform, information indicating eye movement, information indicating body temperature, information indicating the amount of sweat, information indicating a line of sight, sound information, information indicating movement of a person, or information obtained from a body fluid (e.g., blood). Alternatively, information identified from a biomarker may be used as biological information. Alternatively, the biological information may be information based on a potential detected from a living thing. For example, the biological information may be brain waves that are a result of measurement of minute currents caused by brain activity, an electrocardiogram that is a result of measurement of minute currents caused by heartbeats, an electromyogram that is a result of measurement of minute currents caused by muscle activity, or a skin potential that is a result of measurement of minute currents caused in the skin. These are just examples of the biological information, and other types of biological information may be used, instead.

Emotion information, mental information, or psychological information may also be obtained as state information regarding a person by analyzing biological information. For example, information indicating a person's emotion, information indicating a person's mental state, or information indicating a person's psychological state may be obtained by analyzing biological information regarding the person. Information indicating a state of an animal other than a person or a plant may be obtained by analyzing biological information regarding the animal or the plant. As the state information regarding a person, there is a state in which the person is feeling one of three major desires, namely appetite, sleep desire, and sexual desire, and a kind of consciousness characterized by feeling. More specifically, however, the state information regarding a person is information regarding relief, anxiety, gratitude, astonishment, excitement, sexual arousal, curiosity, sexual curiosity, calmness, impatience (irritability), wonder (embarrassment), happiness, luck, relaxation, tension, honor, responsibility, respect, familiarity (friendliness), longing (aspiration), desire (motivation), fear, courage, comfort, pleasure (in terms of good deeds and virtues), regret, satisfaction, dissatisfaction, remorse, disgust, shame, contempt, jealousy, guilt, intent to kill, schadenfreude, saudade, anticipation, superiority, inferiority, grudge, resentment, suffering, sadness, heartbreak, inspiration, anger, distress (agony, anguish, painfulness), resignation (giving up), despair, hope, hatred (love and hate), love, or emptiness. In addition, there are itchiness, pain, urge to urinate, urge to defecate, hunger, satiety, and the like. In addition, there is information regarding a person's thought or intention as information to be communicated between persons, such as approval, agreement, disagreement, rejection, hesitation, or confusion. Because such information can be abundantly obtained from brain wave information regarding a person, the information regarding a person's brain waves may be conveniently used.

The brain waves are generally categorized as follows. The delta (δ) wave has a frequency range of between 1 to 4 Hz, and corresponds to the state of deep sleep without dreams, a non-REM sleep, decreases as the sleep becomes shallower, and corresponds to an unconscious state. The theta (θ) wave has a frequency range of between 4 to 8 Hz, and corresponds to a resting state, dozing-off state, a light fitful sleep, an intuitive state, a creative state, a state of accessing to memory, and insight. The low alpha (α) wave has a frequency range of between 8 to 10 Hz, and corresponds to a relaxed state (resting and conscious but introverted state), appears when closing eyes, and decreases when opening eyes. The high alpha (α) wave has a frequency range of between 10 to 12 Hz, and corresponds to a relaxed state (concentrated and extroverted state), appears when closing eyes, and decreases when opening eyes. The SMR (sensorimotor rhythm) has a frequency range of between 12 to 15 Hz, and corresponds to an in-the-zone state, a balanced state between relaxed and concentrated, appears before movement, and appears before thinking. The low beta (β) wave has a frequency range of between 15 to 20 Hz, and corresponds to thoughts and when solving problems. The high beta (β) wave has a frequency range of between 20 to 30 Hz, and corresponds to an alert state, a nervous state, a stressed state, and a worrying state. The low gamma (γ) wave has a frequency range of between 31 to 40 Hz, and corresponds to memory formation, a higher mental activity, a higher cognitive activity, a happy state. The middle gamma (γ) wave has a frequency range of between 41 to 50 Hz and corresponds to visual information processing. The biological information measuring apparatus 12 may measure part of all of the brain waves discussed above.

The biological information measuring apparatus 12 may be an apparatus (e.g., a wearable device) that is worn by a living thing which is a subject and that measures biological information or may be an apparatus that measures biological information without being worn by a living thing.

A wearable device is, for example, a hearable worn on an animal's ears, a device worn on an animal's head, a device (e.g., a wristwatch-type device such as a smart watch) worn on an animal's wrist, arm, or finger (hereinafter referred to as a "wrist or the like"), a device worn on an animal's neck, a devices worn on an animal's body (e.g., chest, abdomen, etc.), a device worn on a lower limb (e.g., a person's thigh, lower leg, knee, foot, ankle, etc.), a glasses-type device, or a contact lens-type device. The biological information measuring apparatus 12 may worn on a part other than these, instead. In addition, the biological information measuring apparatus 12 may be worn on more than one part.

The hearable may be, for example, earphones, a hearing aid, an earring-type device, a clip-type device, or a device with a band or a cable to be wound around the ears. The device worn on the head may be, for example, a headset with a band or a cable to be wound around the head. The device worn on the wrist may be, for example, a device with a band or a cable to be wound around the wrist. Devices worn on other parts may also come with bands or cables. Hearables, which usually have natural appearances and can perform measurement, may be used especially when brain wave information is measured. Hearables are suitable as devices for measuring brain waves because the hearables have highly versatile shapes like common earphones. Whereas hearables have natural appearances that do not seem to be measuring brain waves at first glance, people can easily tell that medical electroencephalographs, which usually attach electrodes to the head, are measuring brain waves. This causes hesitation in wearing medical electroencephalographs in daily life. In addition, because hearables can use means that can input sound to a person's ears and/or receive voice information from the person's mouth, a result of interpretation of the voice information can be checked with sound and errors in the interpretation can be corrected while detecting brain wave information. Furthermore, because BMIs and brain-computer interfaces (BCIs), which employ brain waves, are often used when devices are operated or persons communicate with each other, the devices need to be operated accurately and information to be communicated needs to be correctly recognized. Because BMIs and BCIs that employ hearables are worn on the ears, it is possible to improve accuracy using the above-mentioned sound input means, or voice information or biological information other than brain waves that has been intentionally caused by a person (e.g., it is possible to check whether electromyographic information generated by intentionally moving the jaw three times, eye potential information generated by intentionally moving the eyes strongly, or the like can be correctly recognized and use such information to, for example, determine whether to perform an operation or communicate with another person).

The biological information measuring apparatus 12 may be an apparatus of a contact type that measures biological information regarding a living thing while coming into contact with the living thing or may be an apparatus of a noncontact type that measures biological information regarding a living thing without coming into contact with the living thing. Alternatively, the biological information measuring apparatus 12 may have functions of both a contact type and a noncontact type. That is, the biological information measuring apparatus 12 may measure biological information regarding a living thing while coming into contact with the living thing and without coming into contact with the living thing. The biological information measured through a contact with the living thing and the biological information measured without a contact with a living thing may be of the same type or of different types.

The biological information measuring apparatus 12 includes electrodes for measuring biological information and sensors other than the electrodes. The electrodes may come into contact with a living thing and detect a potential, which is an example of the biological information or may detect a potential without coming into contact with the living thing. The sensors other than the electrodes may measure biological information while coming into contact with the living thing or without coming into contact with the living thing. For example, the electrodes come into contact with an animal and detect potential indicating brain waves of the animal. The sensors, on the other hand, may measure biological information indicating body temperature of the animal without coming into contact with the animal. This is just an example, and other types of biological information may be measured, instead.

For example, the biological information measuring apparatus 12 includes one or more electrodes. Plural electrodes are attached to a living thing, for example, and detect a potential. The detected potential includes a biopotential, which is an example of the biological information regarding a living thing, and the biological potential is extracted from the detected potential by processing the detected potential. The detected potential might include noise that does not derive from the biopotential, for example, and biological potentials from which the noise has been removed can be obtained by performing processing such as noise cancellation. The noise is, for example, a potential caused by movement of the living thing, a potential from outside the living thing, a potential deriving from a global environment, a potential indicating biological information regarding living things other than a measurement target, or the like. The noise may also include potentials generated by devices such as PCs and smartphones. Different electrodes may be used to detect a potential in accordance with potential detection sensitivity, a measurement condition of noise, or the like. In addition, when potentials deriving from various biopotentials are collectively measured, the potentials deriving from the various biological potentials may be estimated and separated from one another by dividing the measured potential in accordance with frequencies corresponding to the biological potentials or dividing measurement time into periods where all the potentials have been collectively measured and periods where only some of the potentials have been measured. In the case of the above-described hearable, for example, information indicating brain activity, information indicating pulse rate, myoelectric information deriving from movement of muscles and the like, information deriving from blood flow such as pulse wave and heart rate, and the like might be collectively measured, but these pieces of information often have different frequencies or absolute values of outputs. These pieces of information, therefore, can be separately estimated through a frequency analysis of a measured signal or on the basis of levels of output values. Brain waves, for example, can be divided into bands of alpha, beta, theta, delta, and gamma waves. In another method, a hearable may perform measurement and a commercially available electroencephalograph, a commercially available electromyograph, and a commercially available measuring device relating to blood flow may measure individual measurement signals plural times under the same condition. Pieces of biological information from which measurement signal information collectively measured by the hearable derives may then be determined by analyzing the measurement signal information through a frequency analysis based on a Fourier transform or a wavelet transform (WT), and the measurement signal information may be divided through statistical processing.

The biological information measuring apparatus 12 transmits the measured biological information to the information processing apparatus 10. The biological information measuring apparatus 12 may transmit biological information to the information processing apparatus 10 each time the biological information measuring apparatus 12 has measured biological information or store biological information and transmit the biological information to the information processing apparatus 10 at predetermined time intervals or timings specified by a person. Alternatively, the biological information measuring apparatus 12 may receive biological information measured by another biological information measuring apparatus 12 from the other biological information measuring apparatus 12 and transmit biological information measured thereby and the biological information measured by the other biological information measuring apparatus 12 to the information processing apparatus 10.

The biological information measuring apparatus 12 may analyze biological information measured thereby or another biological information measuring apparatus 12 and transmit information indicating a result of the analysis to the information processing apparatus 10. For example, the biological information measuring apparatus 12 may include a processor, and the processor may analyze biological information. The information processing apparatus 10 or another apparatus may conduct the analysis, instead.

The biological information measuring apparatus 12 may include a battery and be driven by power supplied from the battery or may receive power from another apparatus (e.g., the information processing apparatus 10) and be driven.

For example, the information processing apparatus 10 receives biological information from the biological information measuring apparatus 12, analyzes, stores, and outputs the biological information, and stores and outputs information indicating a result of the analysis of the biological information. The biological information measuring apparatus 12 or another apparatus may analyze the biological information, instead. The outputting of biological information is, for example, displaying of the biological information or outputting of the biological information as sound information. The outputting of information indicating a result of an analysis of biological information is, for example, displaying of the information indicating the result of the analysis or outputting of the result of the analysis as sound information. The information processing apparatus 10 may transmit the biological information and the information indicating the result of the analysis to another apparatus, instead.

The information processing apparatus 10 may include the at least one biological information measuring apparatus 12. That is, the at least one biological information measuring apparatus 12 may be incorporated into the information processing apparatus 10 to form a single apparatus. The information processing apparatus 10 including the at least one biological information measuring apparatus 12 may be worn by a living thing and measure biological information. That is, the information processing apparatus 10 may be a wearable device. For example, the information processing apparatus 10 may be an apparatus worn on a person's head (e.g., forehead etc.), a hearable worn on a person's ears (e.g., earphones, headphones, etc.), an apparatus worn on a person's arm, hand, wrist, or finger (e.g., a wristwatch-type device such as a smart watch), an apparatus worn on a person's neck, an apparatus worn on a person's body (e.g., abdomen, chest, etc.), or an apparatus worn on one of a person's lower limbs (e.g., thigh, lower leg, knee, foot, ankle, etc.). The information processing apparatus 10 may be a health appliance or the like worn on a person's arm, hand, body, or lower limb. The information processing apparatus 10 may be worn on a part other than these parts, instead.

The information processing apparatus 10 and the biological information measuring apparatus 12 may be separate apparatuses. For example, the information processing apparatus 10 may be an apparatus such as a robot, a smart speaker, or a server, and the biological information measuring apparatus 12 may be a wearable device worn by a living thing.

The environment information measuring apparatus 14 is configured to measure environment information regarding a surrounding environment of a living thing and the environment information measuring apparatus 14. The environment information measuring apparatus 14 is, for example, a camera that is an image capture device, a microphone that collects sounds, a temperature sensor that measures temperature, a humidity sensor that measures humidity, an odor sensor that measures odor, an illuminance sensor that measures brightness, an infrared sensor, a pressure sensor such as an air pressure sensor, a position sensor that detects movement of a target, a human detection sensor, or the like. At least one of these sensors may be included in the information processing system as the environment information measuring apparatus 14.

For example, a camera captures images of a surrounding environment of the information processing apparatus 10 and other places to generate image data indicating the surrounding environment and image data indicating the other places. The image data may be moving image data or still image data. The image data obtained by the camera is an example of environment information regarding an environment included in an image capture range of the camera. Image data indicating a living thing generated by capturing an image of the living thing using the camera may be used as biological information regarding the living thing. For example, movement of the living thing (e.g., a person), a figure of the living thing, or the like detected from the image data is an example of biological information regarding the living thing. In this sense, the camera is an example of the biological information measuring apparatus 12 that measures biological information regarding a living thing.

Sounds around a microphone (e.g., a person's voice and other sounds) are input to the microphone, and the microphone generates sound data. The sound data indicating the sounds input to the microphone is an example of environment information regarding a surrounding environment of the microphone. The sound data indicating a person's voice input to the microphone may be used as biological information regarding the person. In this sense, the microphone is an example of the biological information measuring apparatus 12 that measures biological information regarding a person. Sound data indicating cries of an animal other than a person may be used as biological information regarding the animal.

Data measured by a temperature sensor, a humidity sensor, an odor sensor, an illuminance sensor, an infrared sensor, a pressure sensor, a position sensor, a human detection sensor, or the like is an example of the environment information. Data measured by these sensors from a living thing may be used as biological information regarding the living thing. In this sensor, these sensors are examples of the biological information measuring apparatus 12 that measures biological information regarding a living thing.

The environment information may be information indicating the size of a room in which a living thing exists, information indicating the size of a room in which the device 16 is provided, information indicating the number of windows provided for a room, or the like. The environment information is not limited to information measured by the environment information measuring apparatus 14 and may be predetermined information or premeasured information, instead.

The at least one environment information measuring apparatus 14 may be included in the information processing apparatus 10.

The device 16 is an example of an operation target. The device 16 is, for example, a PC, a tablet PC, a smartphone, a mobile phone, a robot (e.g., a humanoid robot, an animal robot, a cleaning robot, etc.), a projector, a display device such as a liquid crystal display, a recording device, a playback device, an image capture device such as a camera, a refrigerator, a rice cooker, a microwave oven, a coffee maker, a vacuum cleaner, a washing machine, an air conditioner, a lighting device, a clock, a surveillance camera, an automobile, a motorcycle, an airplane (e.g., an unmanned aerial vehicle such as a drone), a game machine, a gas range, an electronic toilet seat, a ventilation fan, a call bell, an entrance monitor, an elevator, a door, a window, or one of various sensing devices (e.g., a temperature sensor, a humidity sensor, a voltage sensor, a current sensor, etc.). A concept of the device 16 may include devices in general. For example, the concept of the device 16 according to the present exemplary embodiment may include information devices, video devices, audio devices, and other devices.

The device 16 includes a communication unit, which is a communication interface, a memory storing information, and a processor that controls the operation thereof. The device 16 may include user interfaces (UIs) such as a display and an operation unit. The device 16 may transmit device identification information for identifying the device 16 to the information processing apparatus 10. The device identification information is, for example, an identifier (ID), a name, a model number, or an address (e.g., a media access control (MAC) address, an Internet protocol (IP) address, etc.) of the device 16.

In the present exemplary embodiment, an operation target is operated on the basis of biological information regarding at least one living thing (e.g., at least one person). For example, the information processing apparatus 10 obtains biological information regarding a living thing from the biological information measuring apparatus 12 and operates an operation target on the basis of the obtained biological information. For example, the information processing apparatus 10 obtains biological information regarding a living thing from the biological information measuring apparatus 12, identifies an operation to be performed on the operation target on the basis of the obtained biological information, and operates the operation target in accordance with the identified operation. A process for identifying an operation may be performed by the biological information measuring apparatus 12 or another apparatus (e.g., a server, the device 16, the terminal apparatus 18, etc.), instead. An apparatus (e.g., a server, the terminal apparatus 18, etc.) other than the information processing apparatus 10 may operate the operation target, instead. For example, the information processing apparatus 10 may identify an operation on the basis of biological information, and an apparatus other than the information processing apparatus 10 may operate the operation target in accordance with the operation identified by the information processing apparatus 10.

The operation target may be hardware or software, or a combination of hardware and software.

Hardware to be operated is not particularly limited, and may be, for example, the device 16 or an apparatus other than the device 16 (e.g., the information processing apparatus 10, the biological information measuring apparatus 12, the environment information measuring apparatus 14, a server, etc.). Plural pieces of hardware may be determined as operation targets, instead.

Software to be operated is not particularly limited, and may be, for example, an application program, an operating system (OS), or the like. The software to be operated may be software installed on the information processing apparatus 10, the device 16, the terminal apparatus 18, or another apparatus (e.g., the biological information measuring apparatus 12, the environment information measuring apparatus 14, a server, etc.) or software provided through a communication path such as the Internet. Plural pieces of software may be determined as operation targets, instead. When plural pieces of software are to be operated, the pieces of software may be installed on the same piece of hardware or different pieces of hardware.

Figure 2:
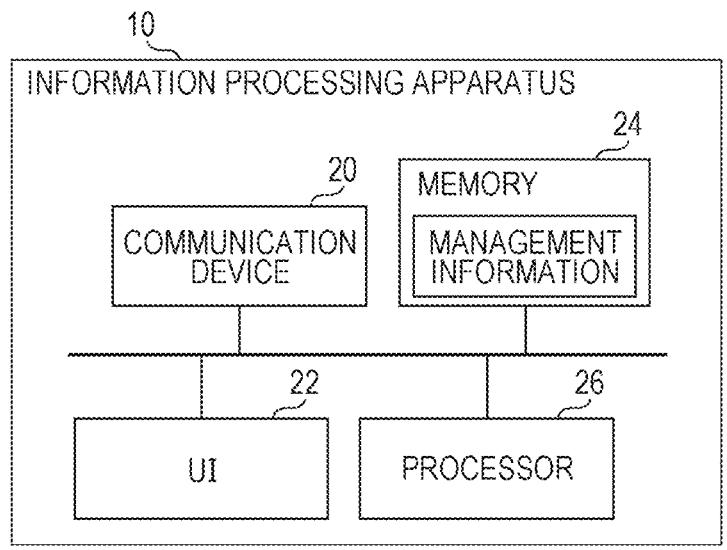
FIG. 2 is a block diagram illustrating the hardware configuration of an information processing apparatus.

The configuration of the information processing apparatus 10 will be described in detail hereinafter with reference to FIG. 2. FIG. 2 illustrates an example of the hardware configuration of the information processing apparatus 10.

The information processing apparatus 10 includes, for example, a communication device 20, a UI 22, a memory 24, and a processor 26. The information processing apparatus 10 may also include other components.

The communication device 20 is a communication interface including a communication chip or a communication circuit and has a function of transmitting information to other apparatuses and a function of receiving information transmitted from other apparatuses. The communication device 20 may have a wireless communication function or a wired communication function. The communication device 20 may communicate with the other apparatuses through, for example, short-distance wireless communication or a communication path such as a LAN or the Internet.

The UI 22 includes at least a display or an operation device. The display is liquid crystal display, an electroluminescent (EL) display, or the like. The operation device is a keyboard, input keys, an operation panel, or the like. The UI 22 may be a touch panel or the like including both a display and an operation device. The UI 22 may also include a microphone and a speaker. The information processing apparatus 10 need not include the UI 22.

The memory 24 is a device for achieving one or more storage areas storing various pieces of information. The memory 24 is, for example, a hard disk drive, one of various memories (e.g., a random-access memory (RAM), a dynamic random-access memory (DRAM), a read-only memory (ROM), etc.), another storage device (e.g., an optical disc etc.), or any selective combination of these. At least one memory 24 is included in the information processing apparatus 10.

The memory 24 stores management information. The management information is information for identifying, on the basis of biological information, an operation to be performed on an operation target.

The processor 26 is configured to control the operation of the other components of the information processing apparatus 10. The processor 26 may include a memory.

For example, predetermined reference biological information and operation information indicating operations to be performed on operation targets are registered in the management information in advance while being associated with each other. The reference biological information may be biological information estimated to be caused in an animal (e.g., a person or another animal) that is performing an operation associated with the reference biological information, biological information estimated to be caused in an animal that is requesting or desires execution of the operation, or biological information estimated to be caused in a plant. In other words, the reference biological information is biological information indicating an operation to be performed on an operation target. The operation information indicating an operation may include information indicating an operation target to be operated in accordance with the operation.

The reference biological information and the operation information may be registered in the management information for each living thing while being associated with each other. For example, the reference biological information and the operation information may be registered in the management information for each type of living thing while being associated with each other. For example, management information for persons, management information for animals other than persons, and management information for plants may be created and stored in the memory 24. In the management information for persons, reference biological information estimated to be measured in the persons and operation information are registered while being associated with each other. Reference biological information and operation information may be registered in the management information for each person (e.g., for each user) while being associated with each other. In the management information for animals other than persons, reference biological information estimated to be measured in the animals and operation information are registered while being associated with each other. Management information may be created for each type of animal other than persons. In the management information for plants, reference biological information estimated to be measured in plants and operation information are registered while being associated with each other. Management information may be created for each type of plant.

The operation information may be information indicating an operation to be performed on a power supply of the device 16, information indicating an operation to be performed for a function level of the device 16, or information indicating both an operation to be performed on the power supply of the device 16 and an operation to be performed for the function level.

The operation to be performed on the power supply of the device 16 is an operation for turning on or off the device 16. The operation information regarding the operation to be performed on the power supply is information indicating an operation for turning on or off the device 16. Biological information associated with the operation information regarding the operation to be performed on the power supply is biological information corresponding to turning on or off of the device 16. Operation information regarding an operation to be performed on the power supply of the device 16 and reference biological information may be registered in management information for each type of living thing or for each living thing while being associated with each other.

The operation to be performed for the function level of the device 16 is an operation for setting the function level of the device 16. The operation information regarding the operation to be performed for the function level is information indicating an operation for setting the function level of the device 16. Biological information associated with the operation information regarding the operation to be performed for the function level is biological information corresponding to the function level of the device 16. Operation information regarding an operation to be performed for the function level of the device 16 and reference biological information may be registered in management information for each type of living thing or for each living thing while being associated with each other.

The function level is, for example, a level relating to performance or output of the device 16. Specific examples of the function level include setting temperature, wind volume, wind direction, and presence or absence of a dehumidification function of an air conditioner, luminance of a display device or a lighting device, sound volume of a speaker, traveling speed of a self-propelled apparatus (e.g., a robot, a self-propelled vacuum cleaner, etc.), setting values of a device such as an image capture device, a recording device, a playback device, setting values of an apparatus such as a refrigerator, a rice cooker, a microwave oven, and setting values of one of various sensing devices. These are just examples, and another setting value or the like may be used as the function level, instead.

The management information may be stored in an apparatus other than the information processing apparatus 10 instead of, or as well as, the information processing apparatus 10.

The processor 26 is configured to obtain biological information regarding a living thing and operate an operation target on the basis of the biological information.

When the biological information measuring apparatus 12 measures biological information in a living thing, for example, the biological information measuring apparatus 12 transmits the biological information to the information processing apparatus 10. The processor 26 receives the biological information and identifies an operation to be performed on an operation target on the basis of the biological information. The processor 26 operates the operation target in accordance with the identified operation. The processor 26 may identify the operation target and the operation to be performed on the operation target on the basis of the biological information regarding the living thing, instead. In another example, the operation target may be determined in advance. For example, a person may specify the operation target. In this case, the processor 26 identifies an operation to be performed on the specified operation target on the basis of the biological information regarding the living thing.

If the operation target is the device 16, the processor 26 transmits control information including operation information indicating an identified operation to the device 16 to operate the device 16. The device 16 to be operated operates in accordance with the control information. The same holds when hardware other than the device 16 is the operation target.

If the operation target is software, the processor 26 operates the software in accordance with the identified operation. For example, the processor 26 activates the software or performs processing using the software. If the software is installed on the information processing apparatus 10, the processor 26 operates the software installed on the information processing apparatus 10. If the software is installed on an apparatus other than the information processing apparatus 10, the processor 26 transmits control information including operation information indicating the operation to the apparatus on which the software is installed to operate the software.

For example, the processor 26 compares the biological information measured in the living thing and the reference biological information registered in the management information and searches for a piece of reference biological information whose difference from the biological information is within an allowable range. The processor 26 identifies an operation to be performed on an operation target associated with the found piece of reference biological information. The operation target and the operation to be performed on the operation target are thus identified. The allowable range is determined in advance. The user may change the allowable range. The allowable range may be defined for each type of living thing or for each living thing.

If plural pieces of reference biological information whose differences from the biological information measured in the living thing are within the allowable range are found, the processor 26 may identify, among the plural pieces of reference biological information, a piece of reference biological information whose difference from the biological information is the smallest and then identify an operation associated with the identified piece of reference biological information or may identify operations associated with the plural pieces of reference biological information.

The reference biological information may be information indicating a characteristic component of biological information. In this case, the processor 26 may extract a characteristic component from the biological information measured in the living thing and search for a piece of reference biological information including a component whose difference from the extracted component is within an allowable range. When brain waves are used as biological information, for example, the processor 26 may extract a characteristic component from brain waves of an animal and estimate an operation indicated by the brain waves by analyzing the characteristic component.

The reference biological information may be used as a threshold, instead. When the reference biological information is a waveform, for example, the amplitude of a peak in the waveform is used as a threshold. In this case, the processor 26 searches for a piece of reference biological information that has a waveform approximate or similar to a waveform indicated by the biological information measured in the living thing and with which the measured biological information exceeds a threshold and identifies an operation associated with the found piece of reference biological information. That is, if the waveform indicated by the measured biological information is approximate or similar to a waveform indicated by a certain piece of reference biological information and the amplitude of a peak in a waveform indicated by the measured biological information is larger than or equal to a threshold, which is the amplitude of a peak in the waveform indicated by the piece of reference biological information, the processor 26 identifies an operation associated with the piece of reference biological information.

When an operation target is operated using information indicating brain activity of an animal, the biological information measuring apparatus 12 that measures the brain activity and the information processing apparatus 10 may together construct a BMI. In general, "BMI" is a general term for devices and the like that serve as interfaces between the brain and a computer or the like through detection of brain waves, stimulation of the brain, or the like. When the brain is connected to a computer, such devices are called "BCIs". In the present exemplary embodiment, usage examples where devices are operated or persons communicate with each other (communication of information regarding a person's thought or intention or state information etc.) using biological information including brain waves will be described. These usage examples will be regarded as part of BMIs hereinafter. An invasive method or a non-invasive method may be employed for a BMI. In this case, the processor 26 operates an operation target on the basis of brain activity (e.g., brain waves etc.). In order to operate an operation target, the processor 26 may extract a characteristic component from brain waves and operate the operation target on the basis of the extracted characteristic component. In order to extract a characteristic component from brain waves, a fast Fourier transform (FFT), a WT, time-frequency distribution (TFD), an eigenvector method (EM), an autoregressive model (ARM), or the like may be used. As a method for connecting brain waves and an operation to be performed on an operation target with each other using a feature vector obtained by extracting a feature, or as a method for connecting a communication target and information to be communicated with each other in communication between persons, for example, an independent component analysis (ICA), k-means clustering, a support vector machine (SVM), a convolutional neural network, or the like may be used.

Alternatively, the processor 26 may receive identification information regarding an operation target transmitted from the operation target and identify the operation target. For example, the processor 26 transmits a request to obtain identification information to an operation target and then obtains the identification information transmitted from the operation target in response to the request. In another case, hardware connected to the information processing apparatus 10 and capable of communicating with the information processing apparatus 10, for example, may transmit identification information regarding the hardware or identification information regarding software installed thereon to the information processing apparatus 10. The processor 26 receives the identification information transmitted in this manner.

The processing performed by the processor 26 may be performed by an apparatus other than the information processing apparatus 10 (e.g., the biological information measuring apparatus 12, the environment information measuring apparatus 14, the device 16, the terminal apparatus 18, or the like), instead. In addition, the information processing apparatus 10 may perform a part of the processing, and an apparatus other than the information processing apparatus 10 may perform another part of the processing. For example, an apparatus other than the information processing apparatus 10 may conduct an analysis of biological information (e.g., the process for identifying an operation), and the information processing apparatus 10 may operate the operation target.

Figure 3:
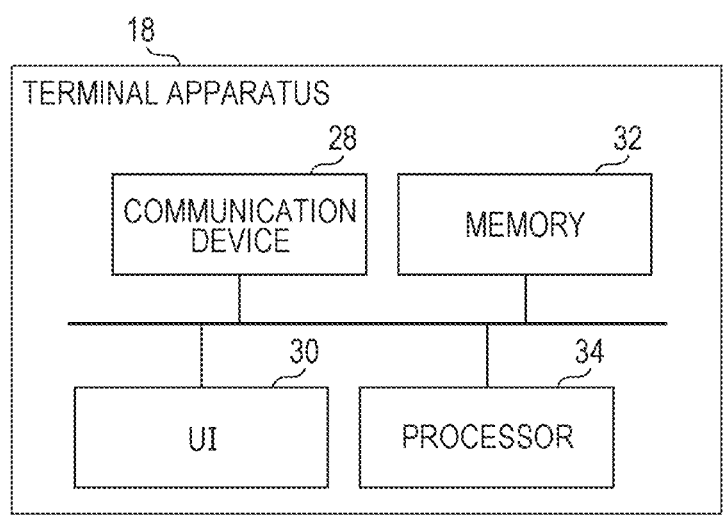
FIG. 3 is a block diagram illustrating the hardware configuration of a terminal apparatus.

The configuration of the terminal apparatus 18 will be described in detail hereinafter with reference to FIG. 3. FIG. 3 illustrates an example of the hardware configuration of the terminal apparatuses 18.

The terminal apparatuses 18 includes, for example, a communication device 28, a UI 30, a memory 32, and a processor 34.

The communication device 28 is a communication interface including a communication chip or a communication circuit and has a function of transmitting information to other apparatuses and a function of receiving information transmitted from other apparatuses. The communication device 28 may have a wireless communication function or a wired communication function. The communication device 28 may communicate with the other apparatuses through, for example, short-distance wireless communication or a communication path such as a LAN or the Internet.

The UI 30 includes at least a display or an operation device. The display is liquid crystal display, an EL display, or the like. The operation device is a keyboard, input keys, an operation panel, or the like. The UI 30 may be a touch panel or the like including both a display and an operation device. The UI 30 may also include a microphone and a speaker.

The memory 32 is a device for achieving one or more storage areas storing various pieces of information. The memory 32 is, for example, a hard disk drive, one of various memories (e.g., a RAM, a DRAM, a ROM, etc.), another storage device (e.g., an optical disc etc.), or any selective combination of these. At least one memory 32 is included in the terminal apparatus 18.

The processor 34 is configured to control the other components of the terminal apparatus 18. The processor 34 may include a memory.

Specific examples of the management information will be described hereinafter.

FIG. 4 illustrates an example of a management table, which is an example of the management information. Data regarding the management table is stored in the memory 24. The data regarding the management table need not be stored in the memory 24 and may be stored in an apparatus other than the information processing apparatus 10 (e.g., a server), instead.

In the management table, IDs, reference brain waves, and operation information indicating operations to be performed on an operation target are associated with one another in advance. The IDs are information for managing information registered in the management table.

The reference brain waves are an example of the reference biological information. The reference brain waves are brain waves estimated to be measured in a person. Although brain waves are used as an example of the reference biological information, biological information other than brain waves may be used as the reference biological information, instead.

The reference brain waves are defined, for example, through statistical processing. The reference brain waves are brain waves estimated to be caused in a person who is performing an operation associated with the reference brain waves or brain waves estimated to be caused in a person who is requesting execution of the operation.

The reference brain waves may be brain waves in a certain frequency band or include brain waves from different frequency bands.

In the example illustrated in FIG. 4, the operation target is the device 16, which is an example of the hardware. The operation target may be hardware other than the device 16 or software, instead.

The operation information includes device identification information for identifying the device 16 to be operated and information indicating an operation to be performed on the device 16. The operation may be, for example, an operation for turning on or off the device 16, an operation for setting a function level of the device 16, or a combination of an operation for turning on or off the device 16 and an operation for setting a function level.

For example, reference brain waves whose ID is "1" are brain waves indicating an operation for starting a cooling function of an air conditioner. Reference brain waves whose ID is "2" are brain waves indicating an operation for stopping the cooling function of the air conditioner.

If brain waves whose difference from the reference brain waves whose ID is "1" is within an allowable range are measured in a person, for example, the processor 26 identifies the operation for starting the cooling function of the air conditioner associated with the reference brain waves. The processor 26 then transmits control information including information indicating the operation for starting the cooling function of the air conditioner to the air conditioner. The air conditioner operates in accordance with the control information. As a result, the cooling function of the air conditioner starts.

Alternatively, the processor 26 may calculate a degree of similarity between brain waves measured in a person and reference brain waves and determine whether the degree of similarity is higher than or equal to a threshold. The threshold is a value corresponding to the allowable range. If the degree of similarity between brain waves measured in a person and reference brain waves is higher than or equal to the threshold, the processor 26 determines that the brain waves measured in the person and the reference brain waves are similar to each other. That is, the processor 26 determines that a difference between the brain waves measured in the person and the reference brain waves is within the allowable range. If brain waves whose degree of similarity to the reference brain waves whose ID is "1" are measured in a person, the processor 26 identifies the operation for starting the cooling function of the air conditioner.

Although the reference brain waves, which are an example of biological information, are registered in the management table in the example illustrated in FIG. 4, emotion information, mental information, psychological information, or the like obtained by analyzing biological information may be registered in the management table instead of the reference brain waves. For example, information indicating a sensation such as hotness or coldness, a mental state, or a psychological state may be registered in the management table as the reference information instead of the reference brain waves. The processor 26 identifies a person's emotion, mental state, or psychological state by analyzing brain waves measured in the person, identifies reference information indicating the identified emotion, mental state, or psychological state, and then identifies, in the management table, an operation associated with the identified reference information.

Figure 38:
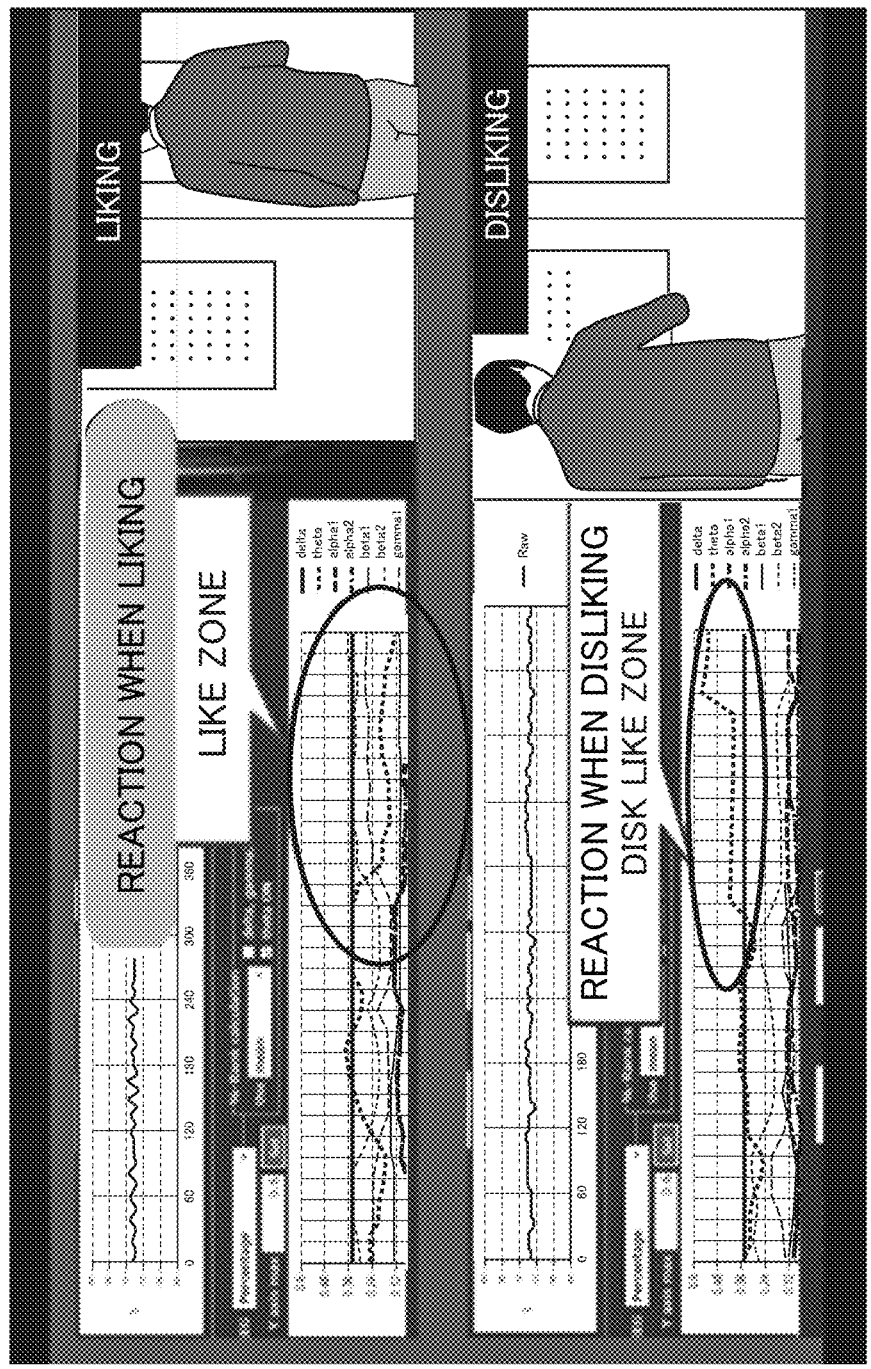
FIG. 38 illustrates brain wave data of a person in a state of liking or disliking.

For example, the difference in the brain waves between the state of liking and disliking is detected based on the difference in the corresponding brain wave data, as illustrated in FIG. 38. In FIG. 38, when a person is writing what they like, the brain waves stay within a specific region (e.g. "like-zone"), while when a person is writing what they do not like, some of the brain waves enter a different region (e.g. "dis-like zone").

Figure 39:
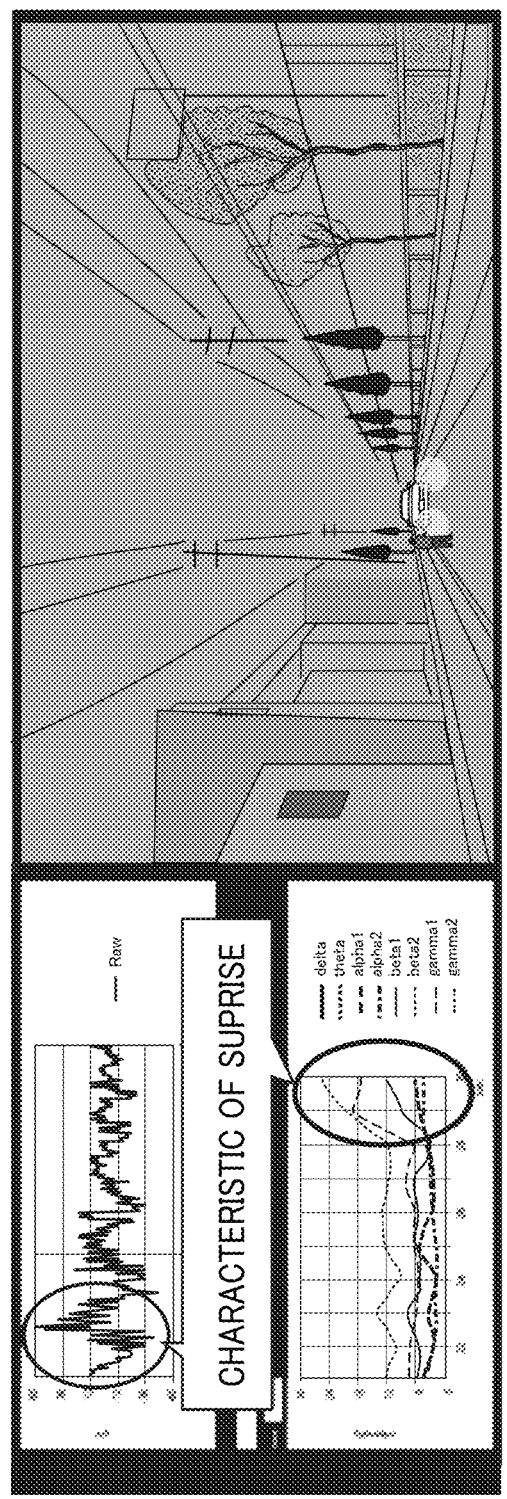
FIG. 39 illustrates brain wave data of a person in a state of surprise.

As another example, as illustrated in FIG. 39, a mental state of a surprise can be detected. For instance, a user may encounter a close-call situation during driving. In such a situation, the brake may be automatically applied and evasive action may be automatically taken based on the driving situation detected by sensors or cameras and the detected brain-state of the user.

A specific example will be described. Reference information indicating a sensation such as hotness, a mental state, or a psychological state is registered in the management table while being associated with operation information indicating the operation for starting the cooling function of the air conditioner. The processor 26 analyzes biological information (e.g., brain waves) measured in a person and identifies the person's emotion, mental state, or psychological state. If the person's emotion indicates a sensation such as hotness, for example, the processor 26 identifies the operation for starting the cooling function of the air conditioner, which is associated with reference information indicating hotness.

The processor 26 may thus identify an operation on the basis of biological information or on the basis of one of various pieces of information (e.g., emotion information, mental information, psychological information, etc.) obtained from the biological information. The same holds in the following examples.

Reference biological information and operation information may be registered in the management table for each living thing while being associated with each other. Biological information measured in individual persons, for example, may be registered in the management table as reference biological information regarding the persons. As for animals and living things other than persons, biological information measured in individual animals and living things may be registered in the management table as reference biological information regarding the animals and the living things.

FIG. 5 illustrates an example of a management table in which specific reference biological information regarding individual persons is registered. In the management table illustrated in FIG. 5, IDs, reference brain waves, which are an example of the reference biological information, operation information, and user information are associated with one another. The user information is information for identifying users, who are the persons (e.g., usernames, user IDs, etc.)

Reference brain waves associated with user information are brain waves measured in a user indicated by the user information when the user was performing an operation associated with the reference brain waves or brain waves measured in the user when the user was requesting the operation. Reference brain waves measured in each user are registered in the management table in advance.

For example, when user A manually starts the cooling function of the air conditioner, the biological information measuring apparatus 12 measures brain waves of user A. The measured brain waves are registered to the management table as reference brain waves indicating an operation performed by user A to start the cooling function of the air conditioner. In this case, the measured reference brain waves of user A, operation information indicating the operation for starting the cooling function of the air conditioner, and user information for identifying user A are registered in the management table while being associated with one another. The information processing apparatus 10 may perform the registration, or another apparatus may perform the registration. In the example illustrated in FIG. 5, these pieces of information are registered as information whose ID is "1". The same holds for other operations and users.

Alternatively, such registration may be performed plural times, and an average of measured brain waves may be registered as reference brain waves. For example, a process in which user A manually starts the cooling function of the air conditioner and the biological information measuring apparatus 12 measures brain waves caused in user A may be performed plural times, and an average of the measured brain waves may be registered to the management table as reference brain waves of user A.

If brain waves whose difference from the reference brain waves whose ID is "1" is within an allowable range are measured in user A with user A having logged in to the information processing apparatus 10, for example, the processor 26 transmits control information including the operation information whose ID is "1" to the air conditioner to start the cooling function of the air conditioner. More specifically, if the biological information measuring apparatus 12 measures brain waves after user A logs in to the information processing apparatus 10, the processor 26 searches for reference brain waves that are registered in the management table and that are associated with the user information for identifying the login user A. Because reference brain waves whose ID is "1" and reference brain waves whose ID is "3" are registered in the management table as reference brain waves of user A in the example illustrated in FIG. 5, the processor 26 finds these reference brain waves. If a difference between the measured brain waves and the reference brain waves whose ID is "1" is within an allowable range, the processor 26 transmits control information including the operation information whose ID is "1" to the air conditioner to start the cooling function of the air conditioner. If a difference between the measured brain waves and the reference brain waves whose ID is "3" is within an allowable range, the processor 26 transmits control information including operation information whose ID is "3" to the air conditioner to start the cooling function of the air conditioner.

In another example, if brain waves whose difference from the reference brain waves whose ID is "1" is within the allowable range are measured in user A with information indicating that a user who is operating the device 16 is user A set to the information processing apparatus 10, the processor 26 may transmit control information including the operation information whose ID is "1" to the air conditioner to start the cooling function of the air conditioner. More specifically, if the biological information measuring apparatus 12 measures brain waves with the information indicating that the user who is operating the device 16 is user A set to the information processing apparatus 10, the processor 26 searches for reference brain waves that are registered in the management table and that are associated with the user information for identifying user A, who is the user who is operating the device 16. If a difference between the measured brain waves and the reference brain waves whose ID is "1" is within the allowable range, the processor 26 transmits control information including the operation information whose ID is "1" to the air conditioner to start the cooling function of the air conditioner. The user who is operating the device 16 may be set to the information processing apparatus 10, for example, by a user.

As for users other than user A, information is registered to the management table in the same manner as for user A. For example, information associated with an ID "2" is information regarding an operation at a time when user B has started the cooling function of the air conditioner. Information associated with the ID "3" is information regarding an operation at a time when user A has stopped the cooling function of the air conditioner.

Although operation information indicating operations for starting and stopping the function of the device 16 is registered in the management tables illustrated in FIGS. 4 and 5, operation information indicating a function level of the device 16 may be registered in the management table, instead.

FIG. 6 illustrates another example of the management table. In a management table illustrated in FIG. 6, reference biological information and operation information are registered for each user while being associated with each other. In the example illustrated in FIG. 6, brain waves and body temperature are used as the reference biological information. In the management table, therefore, IDs, reference brain waves, which are an example of the reference biological information, reference body temperature, which is another example of the reference biological information, operation information, and user information are associated with one another.

If brain waves whose difference from reference brain waves whose ID is "1" is within an allowable range are measured in user A and a body temperature higher than or equal to a threshold is measured in user A, for example, the processor 26 identifies an operation indicated by operation information whose ID is "1" as an operation to be performed on the device 16. The processor 26 then transmits control information including the operation information whose ID is "1" to the air conditioner to start the cooling function of the air conditioner.

Although the reference body temperature, the reference brain waves, and the operation information are associated with one another for each person in the example illustrated in FIG. 6, the reference body temperature, the reference brain waves, and the operation information need not be associated with one another for each person.

FIG. 7 illustrates another example of the management table. In a management table illustrated in FIG. 7, reference brain waves, reference environment information, and operation information are registered for each user while being associated with one another. Although reference brain waves are used as an example of the reference biological information, another piece of biological information may be uses as the reference biological information, instead.

The reference environment information indicates an environment in which the reference brain waves associated therewith are estimated to be measured. Although room temperature is used as the reference environment information, another piece of environment information may be used as the reference environment information, instead.

If brain waves whose difference from reference brain waves whose ID is "1" is within an allowable range are measured in user A and a room temperature at a time when the brain waves have been measured is higher than or equal to a threshold, for example, the processor 26 identifies an operation indicated by operation information whose ID is "1" as an operation to be performed on the device 16. The operation to be performed on the device 16 is thus identified on the basis of brain waves measured in a user and a room temperature at a time when the brain waves have been measured.

Although the reference biological information, the reference environment information, and the operation information are associated with one another for each person in the example illustrated in FIG. 7, the reference biological information, the reference environment information, and the operation information need not be associated with one another for each person. Examples will be described hereinafter.

First Example

A first example will be described hereinafter. In the first example, biological information measured in plural living things in an actual place is used. An example will be described hereinafter in which the device 16 is operated on the basis of biological information measured in plural persons gathering in a room.

Figure 8:
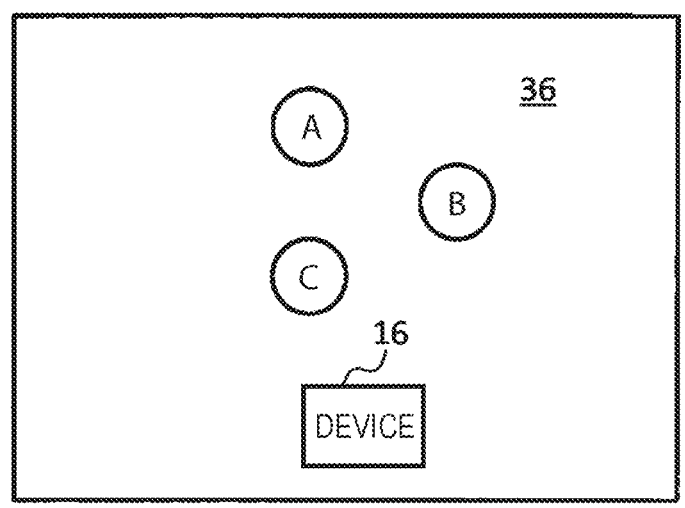
FIG. 8 is a diagram schematically illustrating persons and a device in a certain place.

FIG. 8 schematically illustrates a room 36. There are users A, B, and C, who are the persons, in the room 36. The device 16 is provided in the room 36. The number of users and the number of devices 16 are examples, and plural devices 16 may be provided in the room 36, instead.

Plural biological information measuring apparatuses 12 measure biological information regarding the users. For example, users A, B, and C wear biological information measuring apparatuses 12 that are wearable devices, and the biological information measuring apparatuses 12 measure biological information regarding users A, B, and C. Biological information measuring apparatuses 12 that are not worn by the users may measure biological information regarding the users in addition to, or instead of, the biological information measuring apparatuses 12 worn by the users. One or more types of biological information may be measured in the users. It is assumed here, for example, that brain waves are measured in users A, B, and C. Biological information other than brain waves may be measured, instead.

For example, the biological information measuring apparatuses 12 worn by the users in the room 36 transmit the biological information (e.g., brain wave signals) regarding the users to the information processing apparatus 10. In the example illustrated in FIG. 8, the biological information measuring apparatuses 12 worn by users A, B, and C transmit biological information (e.g., brain wave signals) regarding users A, B, and C, respectively, to the information processing apparatus 10.

The processor 26 of the information processing apparatus 10 operate the device 16 on the basis of brain waves of users A, B, and C. For example, the processor 26 calculates an average of the brain waves measured in users A, B, and C and identifies an operation to be performed on the device 16 on the basis of the average. For example, the processor 26 refers to the management table illustrated in FIG. 4, identifies reference brain waves whose difference from the average is within an allowable range, and then identifies an operation associated with the identified reference brain waves. The processor 26 then operates the device 16 in accordance with the identified operation. For example, the processor 26 calculates an average of amplitudes of the brain waves, identifies reference brain waves whose difference from brain waves whose amplitude is the average is within an allowable range, and then identifies an operation.

In another example, if the operation to be performed on the device 16 is setting of a function level, the processor 26 may separately identify function levels of the device 16 on the basis of the brain waves of users A, B, and C. The processor 26 then calculates an average of the function levels and operates the device 16 in accordance with the average. If the device 16 is an air conditioner having a cooling function, and if an operation identified on the basis of the brain waves of user A is to change setting temperature of the cooling function of the air conditioner to 26C, an operation identified on the basis of the brain waves of user B is to change the setting temperature of the cooling function of the air conditioner to 27C, and an operation identified on the basis of the brain waves of user C is to change the setting temperature of the cooling function of the air conditioner to 28C, for example, the processor 26 calculates an average of the temperatures to be set as the setting temperature. The processor 26 then sets the setting temperature of the cooling function of the air conditioner to the average.

If the operation to be performed on the device 16 is turning on or off, the processor 26 may separately identify turning on or off on the basis of the brain waves of users A, B, and C. The processor 26 then determine whether to turn on or off the device 16 by a majority vote between users A, B, and C and turns on or off the device 16 in accordance with a result of the determination.

Operation Based on Distances Between Device 16 and Users

The processor 26 of the information processing apparatus 10 may identify the operation to be performed on the device 16 on the basis of biological information (e.g., a brain wave signal) regarding a user whose distance from the device 16 to be operated is smaller than or equal to a threshold and then operate the device 16 in accordance with the operation. Positions of the device 16 and the users are identified using a global positioning system (GPS) or another communication technique, for example, and positional information regarding the device 16 and the users is transmitted to the information processing apparatus 10. If the users carry biological information measuring apparatuses 12 or terminal apparatuses 18, for example, positions of the biological information measuring apparatuses 12 or the terminal apparatuses 18 are identified using a GPS or the like, and positional information indicating the positions is transmitted to the information processing apparatus 10 as positional information indicating the positions of the users.

If distances between users A and B and the device 16 are smaller than or equal to the threshold and a distance between user C and the device 16 exceeds the threshold, for example, the processor 26 of the information processing apparatus 10 calculates an average of brain waves of users A and B, identifies the operation to be performed on the device 16 on the basis of the average, and operates the device 16 in accordance with the identified operation. Even if a brain wave signal of user C is transmitted to the information processing apparatus 10, the processor 26 identifies the operation to be performed on the device 16 without using brain waves of user C. In doing so, the device 16 is operated on the basis of biological information regarding users whose distances from the device 16 are smaller than or equal to the threshold.

Operation Based on Distances Between Information Processing Apparatus 10 and Users The processor 26 of the information processing apparatus 10 may identify the operation to be performed on the device 16 on the basis of biological information regarding a user whose distance from the information processing apparatus 10 is smaller than or equal to a threshold and operate the device 16 in accordance with the operation, instead. If the information processing apparatus 10 is a smart speaker or the like and provided in the room 36, for example, the processor 26 may operate the device 16 on the basis of biological information regarding a user whose distance from the information processing apparatus 10 is smaller than or equal to the threshold.

Weighting

The processor 26 of the information processing apparatus 10 may weigh the brain waves of the users, calculate an average of the weighted brain waves, and identify the operation to be performed on the device 16 on the basis of the average.

For example, a weighting coefficient is set for each user, and information indicating the weighting coefficient for each user is stored in the memory 24 of the information processing apparatus 10. For example, each user may determine the weighting coefficient for himself/herself, or a selected one of users A, B, and C may determine the weighting coefficients for all the users. The information indicating the weighting coefficient for each user may be, for example, transmitted from the terminal apparatuses 18 owned by the users to the information processing apparatus 10 or input to the information processing apparatus 10 using the UI 22 of the information processing apparatus 10.

The weighting coefficient for each user may be determined on the basis of an attribute of the user. The attribute is, for example, age, gender, height, weight, or the like. A weighting coefficient is determined in advance for each attribute, and information indicating the weighting coefficient for each attribute is stored in the memory 24 of the information processing apparatus 10 in advance. For example, information indicating attributes of the users is transmitted to the information processing apparatus 10 from the terminal apparatuses 18 owned by the users, and the processor 26 of the information processing apparatus 10 determines the weighting coefficients for the users on the basis of the information indicating the attributes of the users.

Alternatively, the weighting coefficients may be determined on the basis of the distances between the device 16 and the users. For example, the weighting coefficient may increase as the distance between the device 16 and the user becomes smaller, and decrease as the distance between the device 16 and the user becomes larger. A correlation between the weighting coefficient and the distance may be reversed, instead. The distances are calculated on the basis of the positional information regarding the device 16 and the users.

When Biological Information has Changed

When the brain waves of users A, B, and C have changed, the processor 26 of the information processing apparatus 10 changes the operation to be performed on the device 16 in accordance with the change. For example, the processor 26 calculates an average of the brain waves of users A, B, and C at predetermined time intervals, identifies an operation at the time intervals on the basis of the average, and operates the device 16 at the time intervals in accordance with the identified operation. In this case, too, the above-described weighting may be performed. In the first example, the plural living things whose biological information is to be measured may be a combination of at least two of a person, an animal other than a person, and a plant, instead. For example, the device 16 may be operated on the basis of biological information regarding a person and a living thing. The same holds in the following examples.

Process to be Performed when Living Thing has Moved

Figure 9:
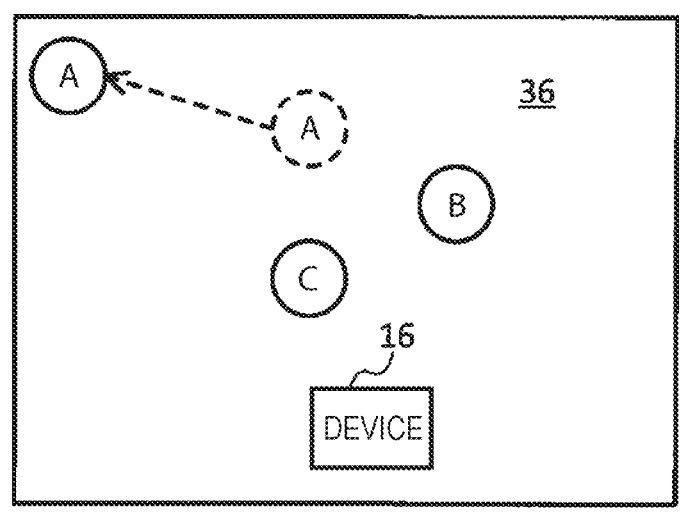
FIG. 9 is a diagram schematically illustrating the persons and the device in the certain place.

A process to be performed when a living thing has moved will be described with reference to FIG. 9. FIG. 9 schematically illustrates the room 36. As in the example illustrated in FIG. 8, there are users A, B, and C, who are the persons, in the room 36. The device 16 is also provided in the room 36.

If user A has moved as indicated by an arrow in FIG. 9, the distance between user A and the device 16 exceeds the threshold whereas the distances between users B and C and the device 16 are smaller than or equal to the threshold, for example, the processor 26 of the information processing apparatus 10 identifies an operation on the basis of the brain waves of users B and C and operates the device 16 in accordance with the identified operation. As described above, the processor 26 may identify an operation on the basis of an average of the brain waves of users B and C and operate the device 16 in accordance with the identified operation, identify function levels on the basis of the brain waves of users B and C and operate the device 16 in accordance with an average of the identified function levels, or determine turning on or off on the basis of the brain waves of users B and C and turn on or off the device 16 in accordance with a result of the determination.

The processor 26 may perform the above-described weighting. If user A before the movement is a user who affects a determination of an operation to be performed on the device 16 in this case (e.g., if the weighting coefficient of user A is larger than those of the other users), the operation might change as a result of the movement of user A.

In the case of measurement of biological information regarding animals and living things other than persons, too, the operation to be performed on the device 16 might change if an animal moves or a position of a living thing changes.

Second Example

A second example will be described hereinafter. In the second example, biological information measured in plural living things located at different places is used. An example will be described hereinafter in which the device 16 is operated on the basis of biological information measured in persons located at different places (e.g., places in different rooms). A scene where the second example is applied, for example, is a scene where plural persons have a conversation or a meeting online (e.g., a remote conference, a web conference, etc.).

It is assumed, for example, that users A, B, C, and D, which are persons, are attending an online meeting. User A is using a terminal apparatus 18A, user B is using a terminal apparatus 18B, user C is using a terminal apparatus 18C, and user D is using a terminal apparatus 18D. The terminal apparatuses 18A to 18D have the same configuration as that of the terminal apparatus 18.

For example, the terminal apparatuses 18A to 18D can receive a service for having an online conversation or meeting from a server that provides the service and communicate information (e.g., images, sounds, text, etc.) with one another. A known service, for example, is used as the service.

Figure 10:
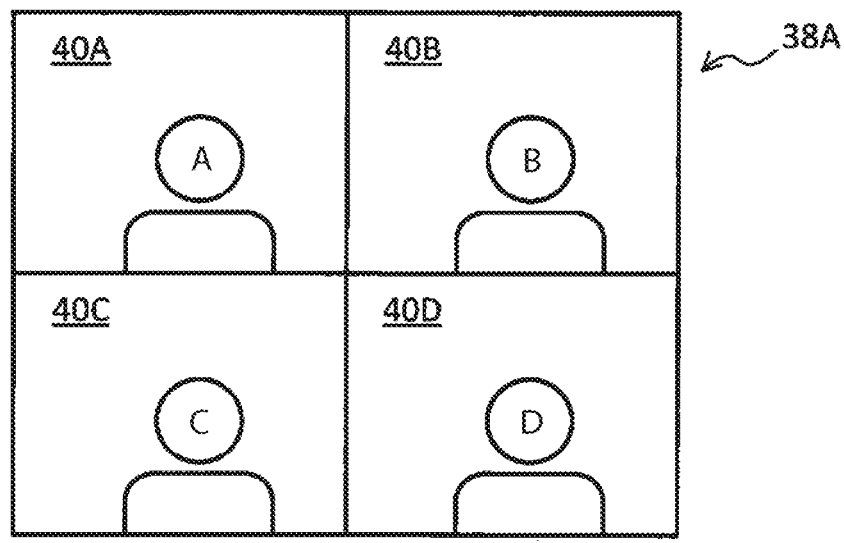
FIG. 10 is a diagram illustrating a screen.

The second example will be described in detail hereinafter with reference to FIG. 10. FIG. 10 illustrates a screen 38A. The screen 38A is displayed on the display of the UI 30 of the terminal apparatus 18A used by user A.

Images of users A to D, who are attending the online meeting, are displayed on the screen 38A. For example, the screen 38A includes areas 40A, 40B, 40C, and 40D. The images of users A to D are displayed on the areas 40A to 40D, respectively. Screens having the same configuration as that of the screen 38A are also displayed on the displays of the terminal apparatus 18B to 18D, respectively.

For example, a camera provided for the terminal apparatus 18A used by user A or a camera that is not provided for the terminal apparatus 18A captures an image of user A, and the processor 34 of the terminal apparatus 18A displays the captured image in the area 40A. The terminal apparatus 18A transmits data regarding the image of user A to the terminal apparatuses 18B to 18D, and displays of the terminal apparatuses 18B to 18D display the image of user A. The same holds for images of users B to D.

As in the first example, the biological information measuring apparatuses 12 measure biological information regarding the users. It is assumed here, for example, that brain waves are measured in users A to D as in the first example. Biological information other than brain waves may be measured, instead. The biological information measuring apparatuses 12 used by the users transmit biological information (e.g., brain wave signals) regarding users A to D, respectively, to the information processing apparatus 10.

The processor 26 of the information processing apparatus 10 operates the device 16 on the basis of the brain waves of users A to D. The terminal apparatuses 18A to 18D may be the devices 16 to be operated, or a device other than the terminal apparatuses 18A to 18D may be the device 16 to be operated.

The terminal apparatuses 18 may each have the function of the information processing apparatus 10, and the processor 34 of each of the terminal apparatuses 18 may operate the device 16 to be operated. For example, each of the terminal apparatuses 18 receives biological information regarding each of the users from the corresponding biological information measuring apparatus 12 through a communication path and operates the device 16.

For example, the processor 34 of each of the terminal apparatuses 18 controls sound volume of a speaker provided for the terminal apparatus 18 on the basis of brain waves of the corresponding user. If it is determined as a result of an analysis of brain waves of user B that user B is excited, for example, the processor 34 of each of the terminal apparatuses 18 controls the sound volume of the speaker provided for the terminal apparatus 18 such that sound volume of user B becomes lower. For example, the processor 34 of the terminal apparatus 18A controls the sound volume of the speaker provided for the terminal apparatus 18A such that the sound volume of user B becomes lower. The same holds for the other terminal apparatuses 18. When a speaker that is not provided for the terminal apparatuses 18 is used, the processor 34 controls sound volume of the speaker.

Users who are going to attend an online meeting may be authenticated. Only authenticated users may attend an online meeting. For example, a recognition technique such as face recognition, voice recognition, retina recognition, or otoacoustic emission recognition may be used. The information processing apparatus 10 or an authentication server may perform the recognition.

In the second example, too, the processor 26 of the information processing apparatus 10 may operate the device 16 on the basis of brain waves of users (e.g., on the basis of an average of the brain waves). The device 16 to be operated may be a device used by at least one of users A to D, or another device. In this case, weighting may be performed.

Process to be Performed when Living Thing has Moved

Figure 11:
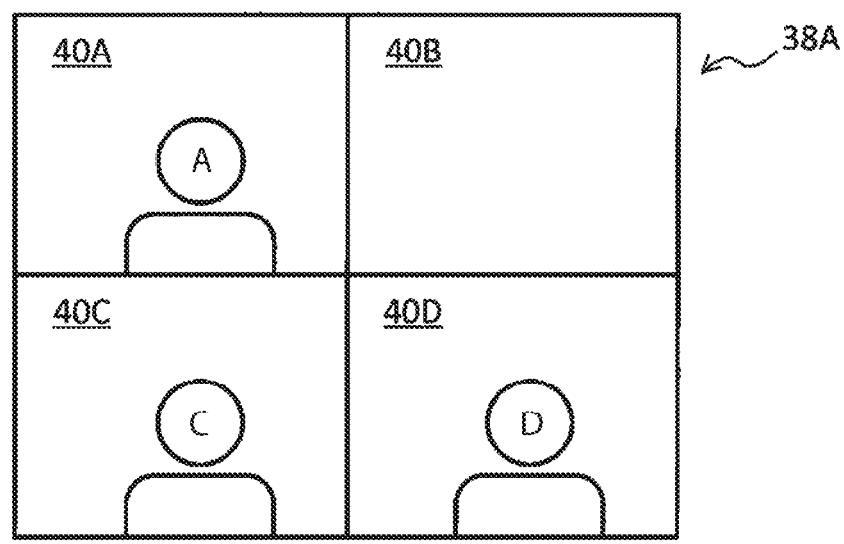
FIG. 11 is a diagram illustrating the screen.

A process to be performed when a living thing has moved will be described hereinafter with reference to FIG. 11. FIG. 11 illustrates the screen 38A.

If user B who has been attending an online meeting leaves or the image of user B is no longer displayed in the area 40B, for example, the processor 26 of the information processing apparatus 10 operates the device 16 on the basis of the brain waves of users A, C, and D.

Third Example

Figure 12:
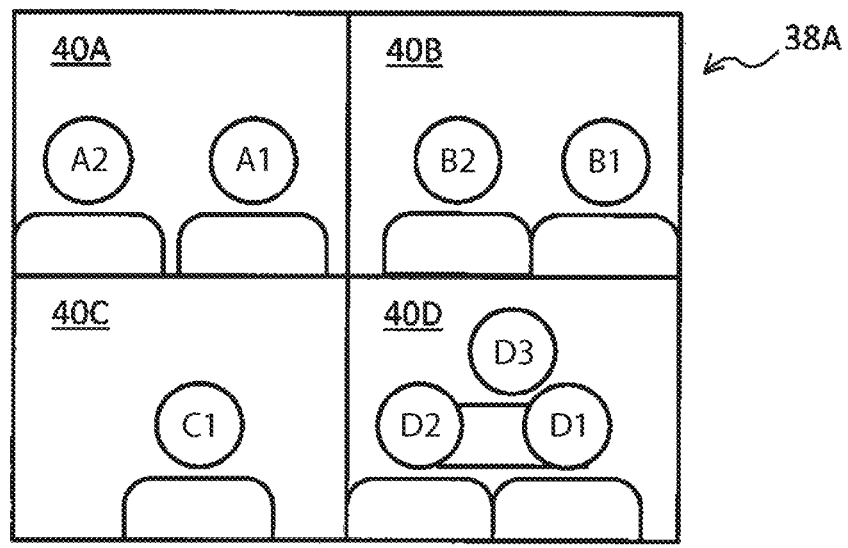
FIG. 12 is a diagram illustrating the screen.

A third example will be described hereinafter with reference to FIG. 12. The third example is a combination of the first and second examples. FIG. 12 illustrates the screen 38A.

It is assumed, for example, that users A1 and A2 are attending an online meeting using the terminal apparatus 18A, users B1 and B2 are attending the online meeting using the terminal apparatus 18B, user C1 is attending the online meeting using the terminal apparatus 18C, and users D1, D2, and D3 are attending the online meeting using the terminal apparatus 18D. For example, users A1 and A2 belong to group A, users B1 and B2 belong to group B, user C1 belongs to group C, and users D1, D2, and D3 belong to group D. Information regarding the groups (e.g., identification information regarding the groups, identification information regarding the users belonging to the groups, etc.) is stored in the information processing apparatus 10, a server, or the like.

Images of users A1 and A2 are displayed in the area 40A, images of users B1 and B2 are displayed in the area 40B, an image of user C1 is displayed in the area 40C, and images of users D1, D2, and D3 are displayed in the area 40D.

As in the first example, the biological information measuring apparatuses 12 measure biological information regarding the users. Biological information regarding one or more users attending an online meeting need not be measured. It is assumed here, for example, that brain waves are measured in the users as in the first example. Biological information other than brain waves may be measured, instead. The biological information measuring apparatuses 12 used by the users transmit biological information (e.g., brain wave signals) regarding the users to the information processing apparatus 10.

As in the second example, the processor 26 of the information processing apparatus 10 operates the device 16 on the basis of the brain waves of the users. The device 16 to be operated may be the terminal apparatuses 18A to 18D or a device other than the terminal apparatuses 18A to 18D, instead. Each of the terminal apparatuses 18A to 18D may have the function of the information processing apparatus 10, and the processor 34 of each of the terminal apparatuses 18A to 18D may operate the device 16 to be operated.

As in the second example, for example, the processor 34 of each of the terminal apparatuses 18 controls the sound volume of the speaker provided for the terminal apparatus 18. If it is determined as a result of an analysis of the brain waves of user B that user B is excited, for example, the processor 34 of each of the terminal apparatuses 18 controls the sound volume of the speaker provided for the terminal apparatus 18 such that the sound volume of user B becomes lower.

In another example, the processor 34 of each of the terminal apparatuses 18 may calculate an average of brain waves of one or more users belonging to a group and determine a state of the group on the basis of the average. If it is determined as a result of an analysis of an average of brain waves of users B1 and B2 belonging to group B that users B1 and B2 are excited, for example, the processor 34 of each of the terminal apparatuses 18 controls the sound volume of the speaker provided for the terminal apparatus 18 such that sound volume of users B1 and B2 becomes lower.

In the third example, too, the processor 26 of the information processing apparatus 10 may operate the device 16 on the basis of brain waves of users (e.g., on the basis of an average of the brain waves). The processor 26 may operate the device 16 on the basis of brain waves of one or more users belonging to a group (e.g., on the basis of an average of the brain waves of the one or more users belonging to the group), instead.

Process to be Performed when Living Thing has Moved

Figure 13:
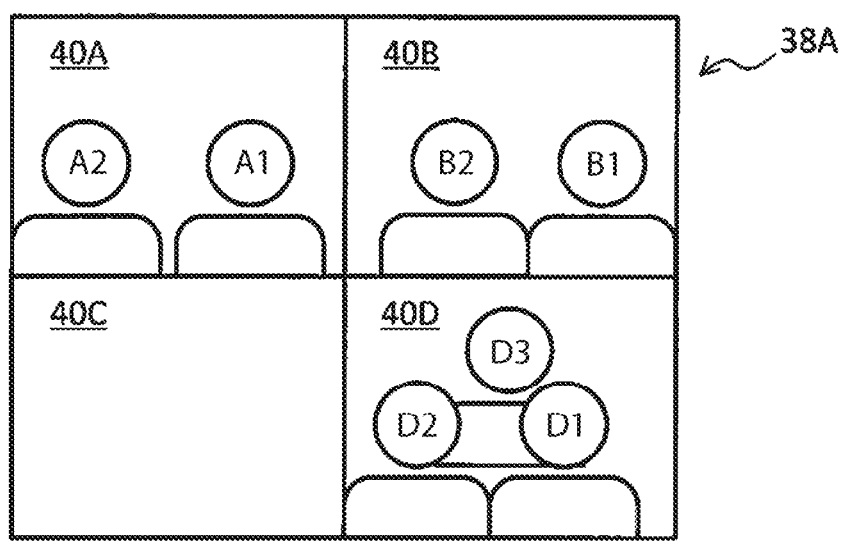
FIG. 13 is a diagram illustrating the screen.

A process to be performed when a living thing has moved will be described hereinafter with reference to FIG. 13. FIG. 13 illustrates the screen 38A.

If user C1 who has been attending an online meeting leaves or an image of user C1 is no longer displayed in the area 40C, for example, the processor 26 of the information processing apparatus 10 operates the device 16 on the basis of brain waves of the users belonging groups A, B, and D.

Fourth Example

A fourth example will be described hereinafter. In the fourth example, a process for encouraging a person to move is performed.

For example, the processor 26 of the information processing apparatus 10 obtains emotion information, mental information, or psychological information regarding a person by analyzing biological information regarding the person. When plural types of biological information are measured, the processor 26 may obtain emotion information, mental information, or psychological information regarding a person by analyzing some or all of the plural types of biological information. The processor 26 may weigh the types of biological information on the basis of order of priority of the types of biological information and obtain emotion information, mental information, or psychological information regarding the person on the basis of a result of the weighting, instead. Alternatively, a reference level may be set for each of the types of biological information, and the processor 26 may determine, for types of biological information whose reference levels are the same, that emotions, mental states, or psychological states have the same tendency.

The processor 26 encourages the person to go to an optimal place on the basis of a result of an analysis of biological information. If determining on the basis of the result of the analysis of the biological information that the person is feeling uncomfortable, for example, the processor 26 encourages the person to go to a place where the person is likely to feel comfortable. The place where the person is likely to feel comfortable is an example of the optimal place.

The processor 26 identifies an optimal place (e.g., a place where a person is likely to feel comfortable) on the basis of biological information measured by the biological information measuring apparatus 12 and environment information measured by the environment information measuring apparatuses 14.

A specific example will be described. If determining on the basis of biological information regarding a person that the person is feeling hot, the processor 26 encourages the person to go to a cooler place. The cooler place is an example of the optimal place. For example, the processor 26 analyzes the amount of sweat and brain waves of a person. If the amount of sweat is larger than or equal to a threshold and the brain waves indicate discomfort, for example, the processor 26 determines that the person is feeling hot. For example, the environment information measuring apparatuses 14 measure environment information such as temperature, humidity, and wind volume in different places and transmit the environment information regarding the places to the information processing apparatus 10. The processor 26 identifies a place where the person is likely to feel cool on the basis of the environment information regarding the places. For example, the processor 26 identifies a place where temperature is lower than in a current location of the person and encourages the person to go to the identified place.

If determining on the basis of biological information regarding a person that the person is feeling cold, the processor 26 encourages the person to go to a warmer place. In this case, the warmer place is an example of the optimal place.

For example, the processor 26 encourages each person to go to optimal places. When there are users A, B, and C in the room 36 as illustrated in FIG. 8, for example, the processor 26 encourages users A, B, and C to go to their respective optimal places. The processor 26 may guide users whose biological information has the same tendency to the same place. If users A and B are feeling hot and user C is feeling cold, for example, the processor 26 guides users A and B to a cooler place and user C to a warmer place.

In another example, when a person is looking at an image or text displayed on a display, the processor 26 encourages a person to move toward the display if determining on the basis of biological information regarding the person that the person is feeling that the image or the text is hard to see.

In yet another example, when a speaker is outputting a sound, the processor 26 encourages a person to move toward the speaker if determining on the basis of biological information regarding the person that the person is feeling that the sound is too small.

Figure 14:
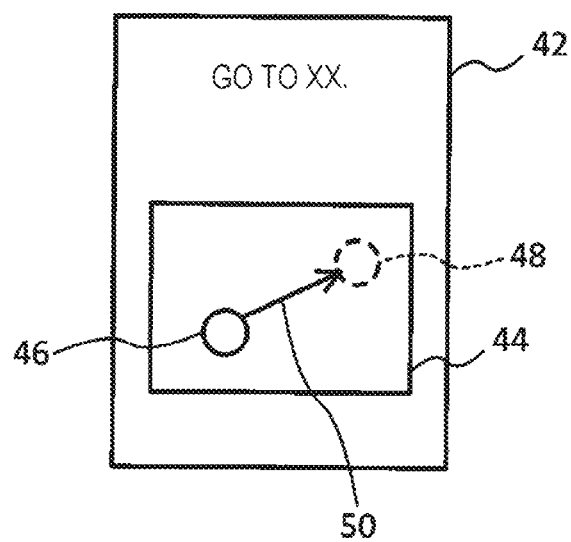
FIG. 14 is a diagram illustrating another screen.

For example, the processor 26 transmits information for encouraging movement (e.g., information indicating guidance or leading etc.) to the terminal apparatus 18 owned by the person. The processor 34 of the terminal apparatus 18 displays the information on the display of the UI 30. FIG. 14 illustrates an example of the information. A screen 42 is displayed on the display of the terminal apparatus 18. The screen 42 includes a message such as "Go to XX (comfortable place)" and a map 44 indicating the comfortable place. A mark 46 indicating a current position of the person, a mark 48 indicating the comfortable place, and an arrow 50 for guiding the person to the comfortable place, for example, are displayed on the map 44. The current position of the person and the comfortable place are identified using a technique such as a GPS. In the example illustrated in FIG. 8, information for encouraging movement is displayed on the displays of the terminal apparatuses 18 owned by users A, B, and C.

Figure 15:
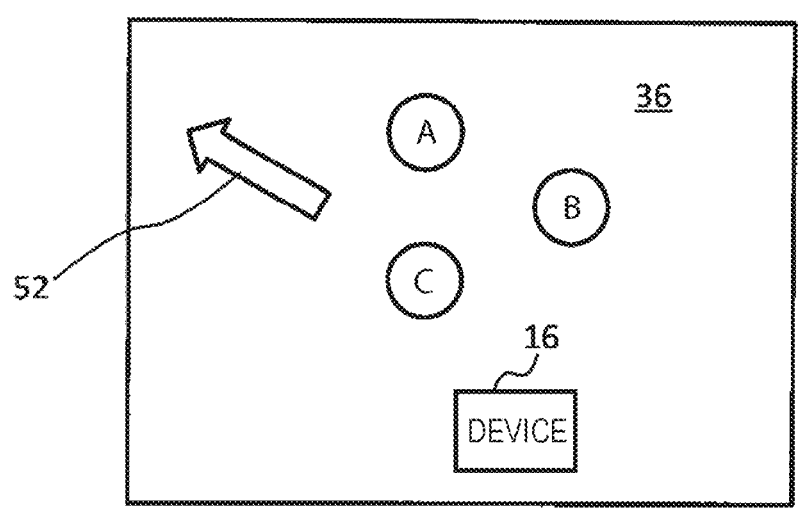
FIG. 15 is a diagram schematically illustrating the persons and the device in the certain place.

FIG. 15 illustrates another example of the information. FIG. 15 illustrates the room 36. For example, the processor 26 of the information processing apparatus 10 may, as indicated by an arrow 52, display guidance by radiating light onto a floor of the room 36. For example, the processor 26 displays the guidance by controlling a lighting device provided inside the room 36. When a person is on a road or the like, the processor 26 displays the guidance on a surface of the road. Alternatively, the processor 26 may display the guidance on a wall or guide a person by sound. The terminal apparatus 18 may output the sound, or another speaker may output the sound. Alternatively, the processor 26 may cause a display provided near a person to display the guidance.

The processor 26 may guide persons whose biological information indicates the same tendency to the same place and persons whose biological information indicates different tendencies to different places. For example, the processor 26 may guide persons who like each other to the same place and persons who dislike each other to different places.

Fifth Example

Figure 16:
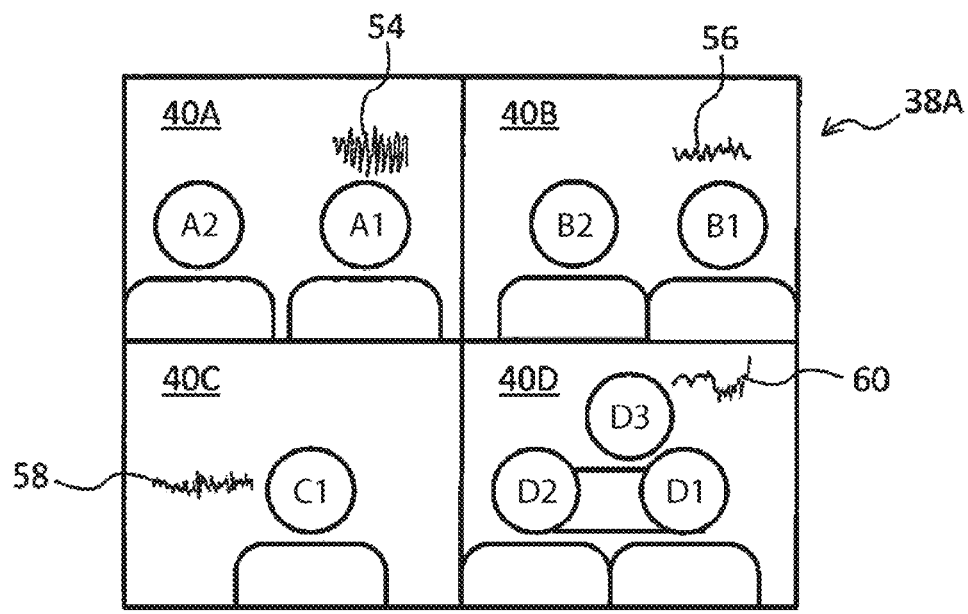
FIG. 16 is a diagram illustrating the screen.

A fifth example will be described hereinafter. In the fifth example, biological information regarding living things is displayed. The fifth example will be described in detail with reference to FIG. 16. FIG. 16 illustrates the screen 38A. It is assumed here, for example, that the users are holding an online meeting as in the third example.

For example, biological information regarding each of the users is transmitted to the terminal apparatus 18 owned by the user, and the processor 34 of the terminal apparatus 18 displays the biological information regarding the user on the display. FIG. 16 illustrates the screen 38A of the terminal apparatus 18A owned by user A, and the processor 34 of the terminal apparatus 18A displays the biological information regarding the users on the screen 38A. FIG. 16 illustrates brain waves, which are an example of the biological information. Waveforms of the brain waves, for example, are displayed.

In the example illustrated in FIG. 16, brain waves 54 of user A1, brain waves 56 of user B1, brain waves 58 of user C1, and brain waves 60 of user D3 are displayed. For example, the processor 34 of the terminal apparatus 18A displays the brain wave 54 of user A1 in the area 40A while associating the brain waves 54 with an image of user A1. The same holds for the brain waves of the other users.

The users can determine whether to display brain waves. The processor 34 of the terminal apparatus 18A displays or does not display brain waves of a user in accordance with an instruction made by user A of the terminal apparatus 18A or an instruction made by the user whose brain waves have been measured.

If user A of the terminal apparatus 18A determines that brain waves of users A1, B1, C1, and D3 are to be displayed, the processor 34 of the terminal apparatus 18A displays the brain waves of users A1, B1, C1, and D3 as illustrated in FIG. 16.

In another example, user A1 may determine whether to display the brain waves thereof. If user A1 determines that the brain waves thereof are to be displayed, the brain waves thereof are displayed. If user A1 determines that the brain waves thereof are not to be displayed, the brain waves thereof are not displayed. The same holds for the other users.

The processor 34 of the terminal apparatus 18 may display, in addition to a waveform of brain waves, information indicating an emotion, a mental state, or psychological state obtained by analyzing the brain waves. The brain waves 58, for example, indicate a state of arousal (excitement), and the processor 34 displays text indicating the arousal (excitement) in the area 40C along with the brain waves 58. The same holds for the other brain waves.

The processor 26 of the information processing apparatus 10 may convert sound data during the online meeting into text data and store the text data in the memory while associating the text data with biological information (e.g., brain waves) regarding the users. In addition, the processor 26 may store the sound data in the memory while associating the sound data with the biological information regarding the users. In addition, the processor 34 of the terminal apparatus 18 may obtain the text data and display text indicated by the text data. For example, sound data or text data associated with biological information may be searched for using the biological information as a search key.

The processor 34 of the terminal apparatus 18 may display brain waves indicating a predetermined emotion, mental state, psychological state, or intention information. If brain waves that are not suitable for a meeting (e.g., brain waves indicating sleepiness, sleep, etc.) are measured, for example, the processor 34 displays the brain waves while associating the brain waves with an image of a user in which the brain waves have been measured.

Figure 17:
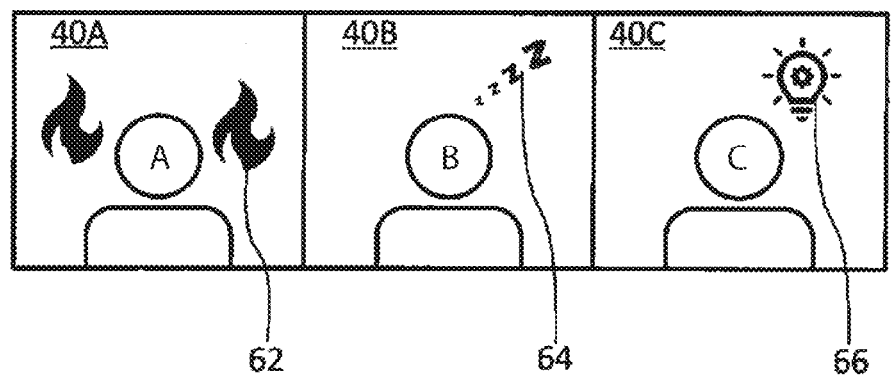
FIG. 17 is a diagram illustrating the screen.

Images indicating emotions, mental states, psychological states, or intention information may be displayed. FIG. 17 illustrates an example of the images. An image 62 indicating concentration, an image 64 indicating sleepiness, and an image 66 indicating relaxation, for example, are displayed. For example, the processor 34 of the terminal apparatus 18 displays the images in addition to, or instead of, brain waves while associating the image with the users.

The processor 34 of the terminal apparatus 18 may change the number of images, color, a highlighting method, a type of images, or the like in accordance with a degree of an emotion, a mental state, a psychological state, or intention information.

The processor 34 may display a score according to a degree of an emotion, a mental state, a psychological state, or intention information while associating the score with a user.

The processor 34 may process and display an image of a user (e.g., a face image of the user) or change a background image of the user in accordance with a degree of an emotion, a mental state, a psychological state, or intention information. If a user has a negative feeling, for example, the processor 34 displays the user's face in white or a pale color. If a user has a positive feeling, the processor 34 displays the user's face in a bright color. Alternatively, if a user has a negative feeling, the processor 34 may display a background image in a darker tone. If a user has a positive feeling, the processor 34 may display a background image in a lighter tone.

Sixth Example

Figure 18:
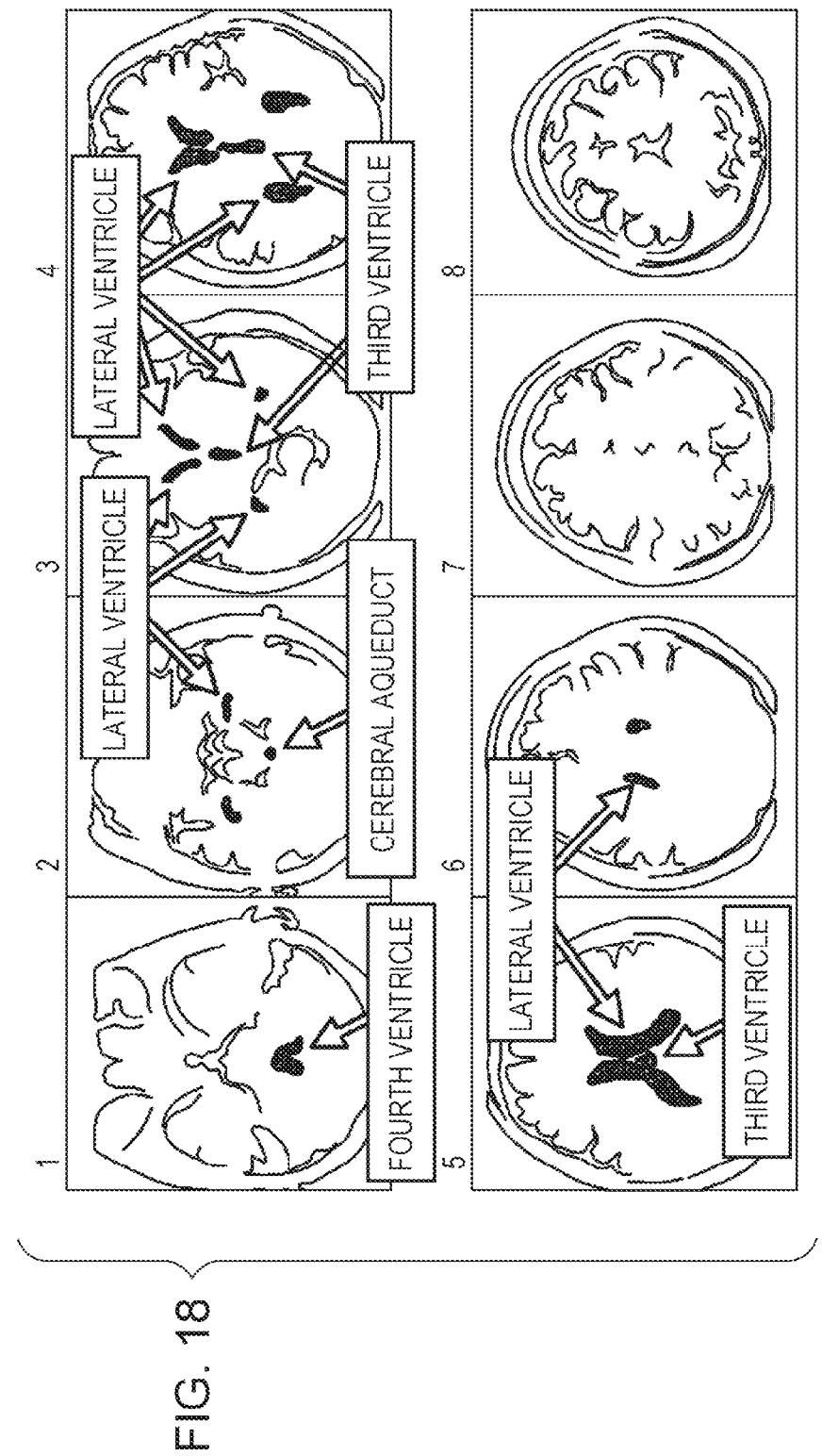
FIG. 18 is a diagram schematically illustrating tomographic images of a person's brain.

A sixth example will be described hereinafter with reference to FIG. 18. FIG. 18 schematically illustrates tomographic images of a person's brain.

For example, the biological information measuring apparatus 12 measures brain waves of a person, and the processor 26 of the information processing apparatus 10 identifies active parts of the person's brain on the basis of the measured brain waves. For example, the processor 26 measures brain waves with three or more electrodes attached to the person's head and identifies parts where the measured brain waves are caused. The processor 26 may display marks indicating the identified parts on tomographic images of the person's brain or apply a color to the identified parts.

The tomographic images may be ones captured by a computed tomography (CT) apparatus or a magnetic resonance imaging (MRI) apparatus or may be images schematically expressing the brain (e.g., prepared images).

Seventh Example

Figure 19:
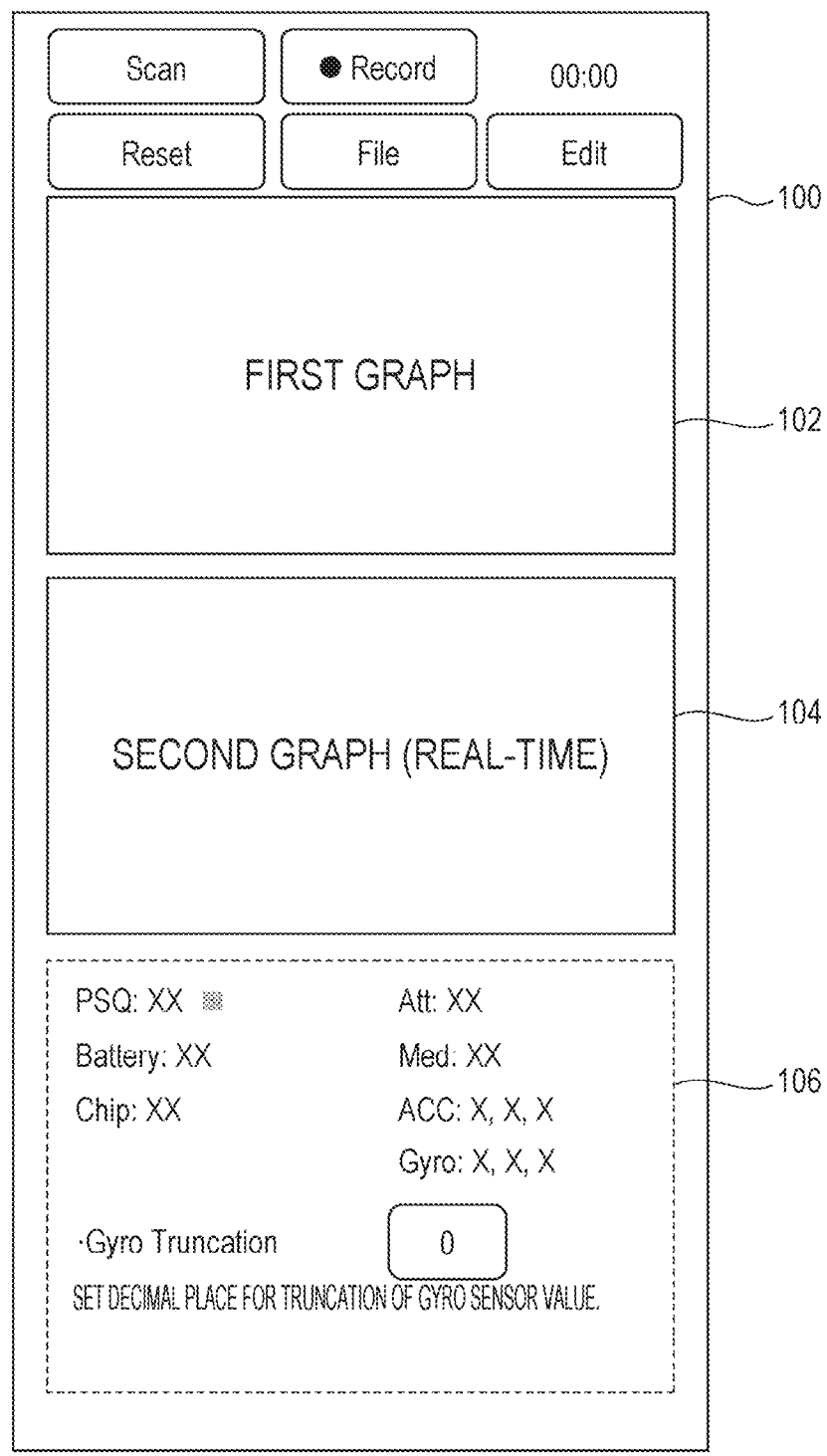
FIG. 19 is a diagram illustrating another screen.

A screen on which biological information is displayed will be described hereinafter. FIG. 19 illustrates an example of a home screen.

A home screen 100 is displayed, for example, on the display of the terminal apparatus 18. A "Scan" button, a "Record" button, a "Reset" button, a "File" button, and an "Edit" button are displayed on the home screen 100. The home screen 100 also includes display areas 102, 104, and 106. In the example illustrated in FIG. 19, the areas 102, 104, and 106 are arranged from top to bottom in this order, but this arrangement is just an example. The user may change the arrangement.

When the "Scan" button is pressed, a list of biological information measuring apparatuses 12 capable of communicating (e.g., can be paired using Bluetooth (registered trademark) low energy (BLE)) with the terminal apparatus 18. When the "Record" button is pressed, biological information measured by the biological information measuring apparatuses 12 is stored in the memory. For example, the biological information measuring apparatuses 12 and the terminal apparatus 18 communicate with each other, and the biological information measured by the biological information measuring apparatuses 12 is transmitted from the biological information measuring apparatuses 12 to the terminal apparatus 18 and stored in the memory 32 of the terminal apparatus 18. When the "Reset" button is pressed, calibration settings are reset. When the "File" button is pressed, a screen for managing files of biological information is displayed. When the "Edit" button is pressed, a setting screen (refer to FIG. 23) that will be described later is displayed.

Biological information measured by the biological information measuring apparatuses 12 is displayed in the area 102. Information obtained by processing the biological information is displayed in the area 104. Unprocessed biological information will be referred to as "raw data" hereinafter. For example, a graph of raw data (hereinafter referred to as a "first graph") is displayed in the area 102, and a graph of processed biological information (hereinafter referred to as a "second graph") is displayed in the area 104.

Setting values and the like of the graph displayed in the area 104 are displayed in the area 106.

A vertical axis (Y-axis) of the first graph represents potential (e.g., [V]) indicating biological information, and a horizontal axis (X-axis) represents time. The range of the vertical axis can be changed, for example, through pinching, zooming, or the like.

A vertical axis (Y-axis) of the second graph before switching represents potential (e.g., [V]) indicating biological information, and a horizontal axis (X-axis) represents time. The range of the vertical axis can be changed, for example, through pinching, zooming, or the like.

The information displayed in the areas 104 and 106 may be switched to other pieces of information. The information is switched, for example, when an operation for sliding the area 104 or 106 such as a flick. The information may be switched through another operation, instead.

Figure 20:
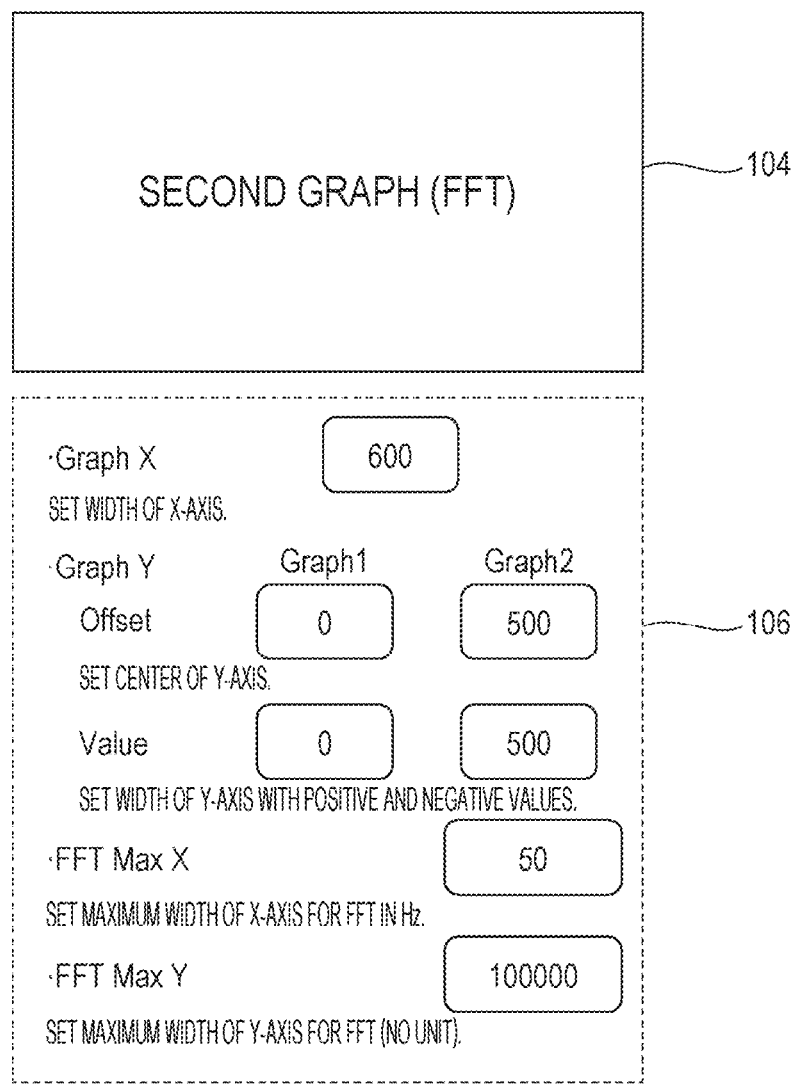
FIG. 20 is a diagram illustrating another screen.

FIG. 20 illustrates information displayed as a result of the switching.

The second graph before the switching is, for example, a graph (e.g., a real-time graph) generated by performing a process set in the setting screen, which will be described later, on raw data. Setting values and the like relating to the second graph are displayed in the area 106 before the switching. An index indicating that biological information (e.g., brain waves) has been obtained, an index indicating that a person in which biological information has been measured is concentrating, an index indicating that the person in which biological information has been measured is relaxed, values of a six-axis sensor (e.g., values indicating the amount of movement in X, Y, and Z-axis directions, values indicating the amount of rotation about X, Y, and Z-axes, etc.) mounted on the biological information measuring apparatus 12, for example, are displayed in the area 106. The values displayed in the area 106 are updated, for example, at predetermined time intervals (e.g., every second). An image having a color corresponding to each value may also be displayed.

The second graph after the switching is a graph (hereinafter referred to as an "FFT graph") generated by performing an FFT on raw data. Setting values relating to the first and second graphs and the FFT graph are displayed in the area 106 after the switching. An item "Graph X", an item "Graph Y", an item "FFT Max X", and an item "FFT Max Y", for example, are displayed in the area 106. The item "Graph X" is used to set a value common to the X-axes of the first graph and the FFT graph. The item "Graph Y" is used to set values of the Y-axes of the first and second graphs. An item "Graph1" is used to set a value of the Y-axis of the first graph, and an item "Graph2" is used to set a value of the Y-axis of the second graph. The item "FFT Max X" is used to set a maximum value of the X-axis of the FFT graph. The item "FFT Max Y" is used to set a maximum value of the Y-axis of the FFT graph.

Figure 21:
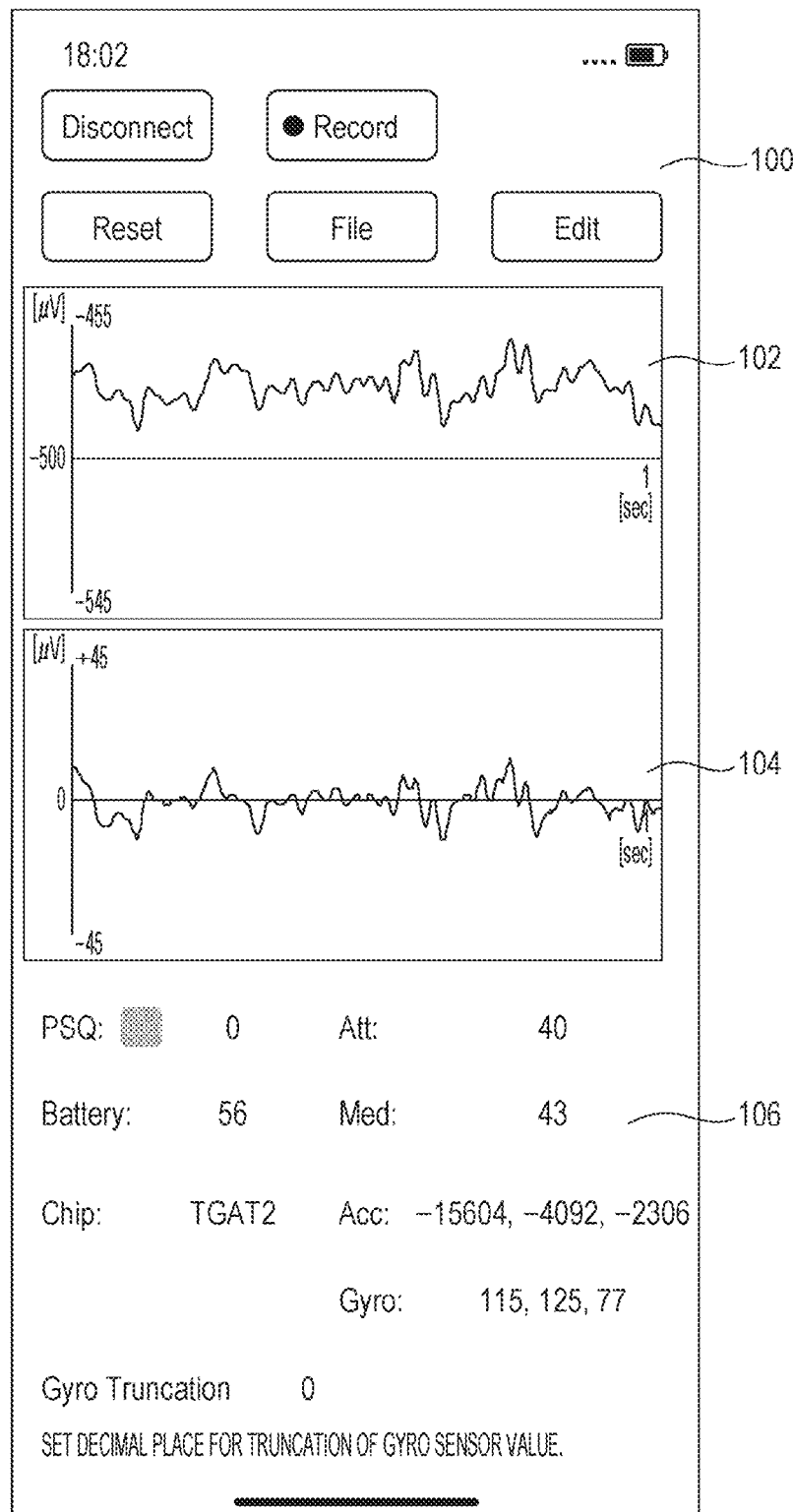
FIG. 21 is a diagram illustrating a specific example of graphs.
Figure 22:
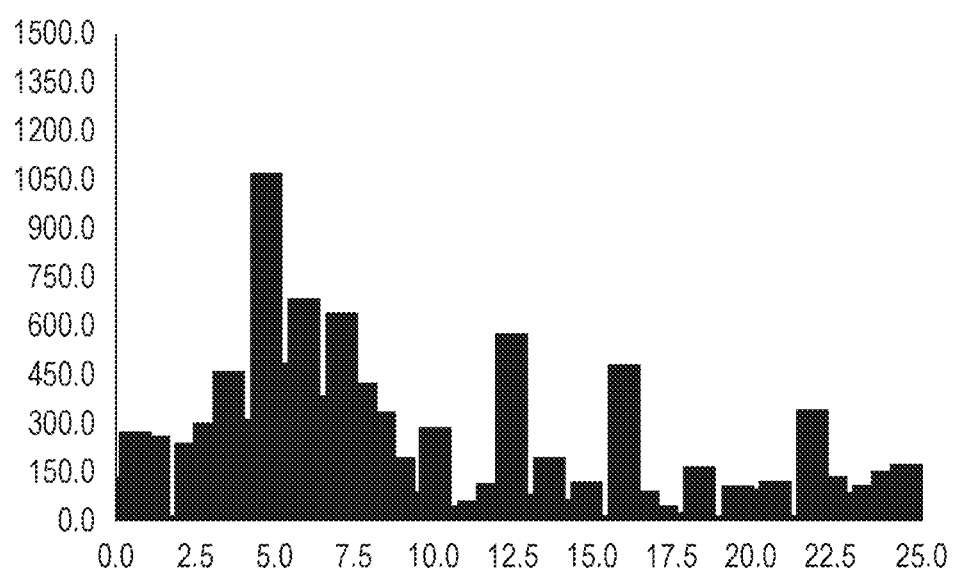
FIG. 22 is a diagram illustrating a specific example of a graph.

FIG. 21 illustrates a specific example of the first graph of raw data and the second graph before the switching. FIG. 22 illustrates a specific example of the second graph after the switching (the graph subjected an FFT).

Figure 23:
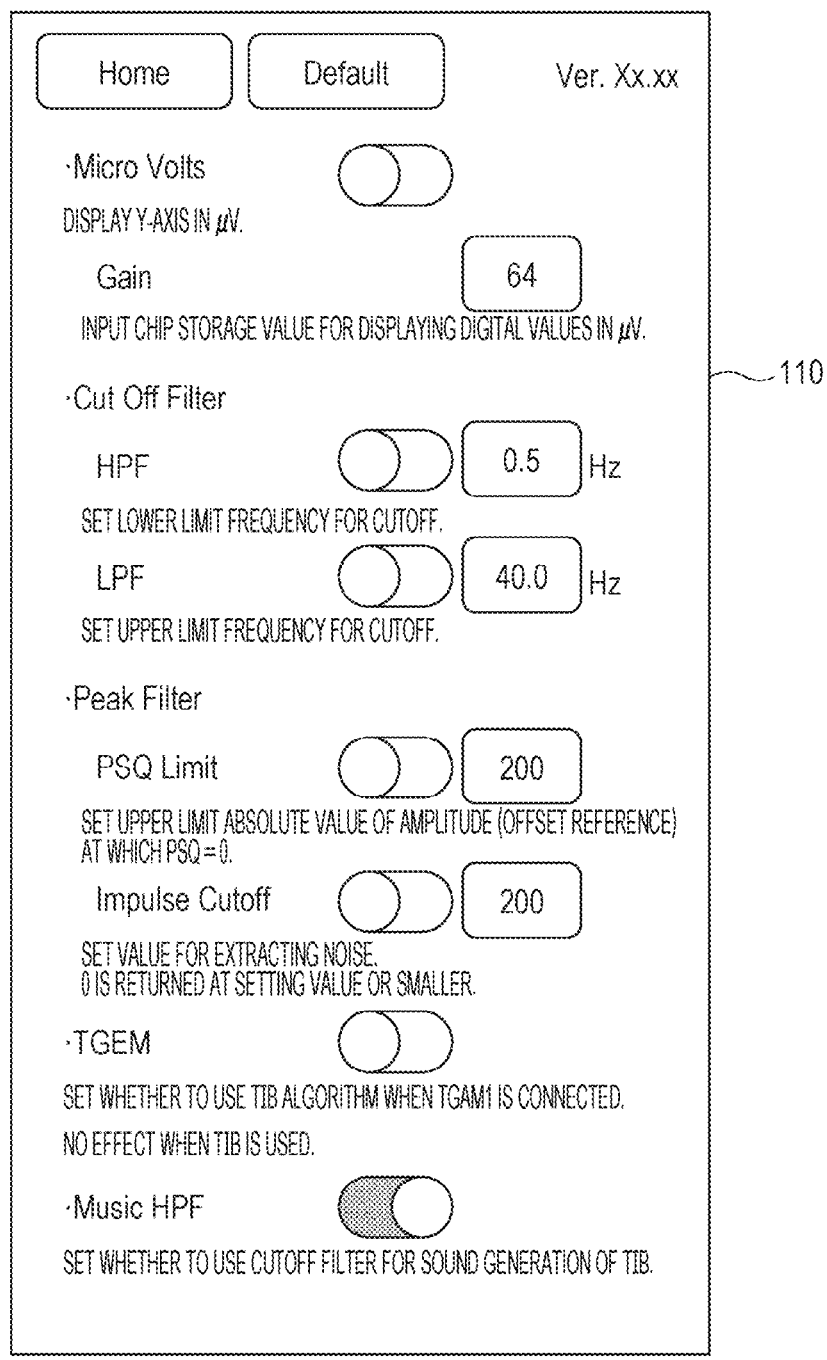
FIG. 23 is a diagram illustrating a setting screen.

FIG. 23 illustrates an example of the setting screen. When the "Edit" button is pressed on the home screen 100, a setting screen 110 illustrated in FIG. 23 is displayed.

An item "Micro Volts" is used to set "V" as a unit for the Y-axes of the first and second graphs.

An item "Cut Off Filter" is used to set setting values of filters (e.g., a high-pass filter (HPF) and a low-pass filter (LPF)) used for biological information. The biological information is filtered in accordance with these setting values.

For example, the first and second graphs are filtered. The filtering may be performed by the biological information measuring apparatus 12, the information processing apparatus 10, or the terminal apparatus 18. As a result of the filtering, information having certain frequencies can be extracted from the measured biological information. For example, only brain waves or myoelectric signals (e.g., signals based on movement of the eyes, the face, the jaws, and the like) can be extracted from biological information including the brain waves and the myoelectric signals. The device 16 may be operated on the basis of the extracted signals. For example, the processor 26 of the information processing apparatus 10 may separately extract the brain waves and the myoelectric signals and operate the same device 16 or different devices 16 on the basis of the brain waves and the myoelectric signals.

An item "Peak Filter" is used to set values relating to processing for a peak value of raw data. The item "Peak Filter" includes, for example, an item for setting an upper limit to the peak value of raw data in measurement of biological information (e.g., brain waves) and an item for setting a value for measuring impulse noise.

Eighth Example

An eighth example will be described hereinafter. In the eighth example, the processor 26 of the information processing apparatus 10 estimates, on the basis of biological information regarding a person, an emotion, a mental state, or a psychological state of another person having a certain relationship with the foregoing person. The processor 26 may estimate, on the basis of emotion information, mental information, or psychological information regarding a person, an emotion, a mental state, or a psychological state of another person, instead.

The certain relationship is, for example, a parent-child relationship or a blood relationship. For example, the processor 26 may estimate an emotion, a mental state, or a psychological state of a child on the basis of biological information, emotion information, mental information, or psychological information regarding a parent, an emotion, a mental state, or a psychological state of a parent on the basis of biological information, emotion information, mental information, or psychological information regarding a child, or an emotion, a mental state, or a psychological state of a person on the basis of biological information, emotion information, mental information, or psychological information regarding the person's sibling.

For example, the biological information measuring apparatuses 12 measure biological information regarding a parent and biological information regarding a child. If the biological information regarding the child is similar to that regarding the parent (e.g., if brain waves of the child have a waveform similar to a waveform of brain waves of the parent), the processor 26 of the information processing apparatus 10 estimates that an emotion, a mental state, or a psychological state of the child is the same as an emotion, a mental state, or a psychological state of the parent. If the biological information regarding the parent indicates that the parent is feeling good and the biological information regarding the child is similar to that regarding the parent, for example, the processor 26 estimates that the child is also feeling good. Such an estimation is performed, for example, when the child is a baby, an infant, or the like for whom it is difficult to control his/her emotion, mental state, or psychological state.

In another example, when the parent is a person for whom it is difficult to control his/her emotion, mental state, or psychological state (e.g., a dementia sufferer), the processor 26 may estimate an emotion, a mental state, or a psychological state of the parent on the basis of biological information, emotion information, mental information, or psychological information regarding the child.

In yet another example, the processor 26 may estimate emotions, mental states, or psychological states of persons whose lifestyles are similar to each other. Persons who have been living together for a long time, for example, often have similar lifestyles. In this case, the processor 26 estimates an emotion, a mental state, or a psychological state of a person on the basis of biological information, emotion information, mental information, or psychological information regarding another person who has a lifestyle similar to the foregoing person.

Ninth Example

A ninth example will be described hereinafter. In the ninth example, the processor 26 of the information processing apparatus 10 notifies a target, who is a person, of certain information that the target does not know. For example, the processor 26 transmits the certain information to a terminal apparatus 18 owned by the target.

The certain information of which the target is notified is, for example, visual information, environment information, atmosphere information regarding a certain place, or the like. Information that can be obtained only in the certain place, for example, is the information of which the target is to be notified. The certain place is specified, for example, by a manager of the information processing apparatus 10, the target, or the like. In addition, information regarding a danger caused in the certain place or information indicating a danger that can be caused in the certain place may be transmitted to the terminal apparatus 18 owned by the target in accordance with an instruction from the manager, the target, or the like.

The visual information is, for example, an image captured by a fixed camera provided in the certain place, an image captured by a camera worn by a person in the certain place, or the like. The visual information may include sound information measured by a microphone provided in the certain place or a microphone worn by a person in the certain place. The environment information is information (e.g., temperature, humidity, air quality, weather, etc.) measured by various sensors provided in the certain place or information measured by a sensor worn by a person in the certain place. The atmosphere information is, for example, information indicating that the certain place is comfortable or uncomfortable to a person, information indicating whether the certain place is a place where a person can concentrate, or the like. If a person in the certain place inputs atmosphere information regarding the certain place to a terminal apparatus 18 owned thereby, for example, the terminal apparatus 18 transmits the input information to the information processing apparatus 10.

If the target specifies a certain place and makes a request to obtain certain information regarding the certain place using the terminal apparatus 18, for example, the terminal apparatus 18 transmits information indicating the request to the information processing apparatus 10. The processor 26 of the information processing apparatus 10 transmits the certain information regarding the certain place to the terminal apparatus 18 in response to the request. The processor 34 of the terminal apparatus 18 displays the certain information on the display or outputs the certain information from the speaker as a sound.

The processor 26 of the information processing apparatus 10 may observe situations in various places and, if a situation in a certain place specified by the target satisfies a predetermined condition, transmit certain information regarding the certain place to the terminal apparatus 18 owned by the target. A situation in a place is, for example, a situation relating to an environment obtained by analyzing environment information (e.g., temperature, humidity, weather, etc.), a situation obtained from visual information (e.g., crowdedness of a town, a train, etc.), or a dangerous situation obtained from visual information, environment information, or the like. A situation in a place may be estimated or predicted from visual information, environment information, or the like.

If weather in a certain place specified by the target is, or is predicted to become, predetermined weather, for example, the processor 26 of the information processing apparatus 10 transmits information regarding the weather in the certain place to the terminal apparatus 18 owned by the target. If crowdedness of a certain place is, or is predicted to become, a predetermined level of crowdedness, the processor 26 of the information processing apparatus 10 transmits information regarding the crowdedness of the certain place to the terminal apparatus 18 owned by the target.

The processor 26 of the information processing apparatus 10 may select certain information to be transmitted to the terminal apparatus 18 owned by the target on the basis of a purpose of the target (e.g., to avoid dangers etc.). The purpose is specified, for example, by the target.

If an automobile is out of control and a person gives, using a terminal apparatus 18, an instruction to transmit information regarding the automobile to the information processing apparatus 10, for example, the terminal apparatus 18 transmits the information regarding the automobile (e.g., information including information indicating a danger) to the information processing apparatus 10. The information regarding the automobile includes positional information regarding the terminal apparatus 18. If a camera worn by the person captures an image of the automobile, the information regarding the automobile may include the captured image. Upon receiving the information regarding the automobile, the processor 26 of the information processing apparatus 10 obtains an image captured by a fixed camera provided near a position of the terminal apparatus 18 (e.g., an image captured at a higher position) from the fixed camera and transmits the image to the terminal apparatus 18 owned by the target. The image is displayed on the display of the terminal apparatus 18 owned by the target. The processor 26 may also transmit the information indicating the danger to the terminal apparatus 18 owned by the target. The information indicating the danger is displayed on the display of the terminal apparatus 18 owned by the target. When plural fixed cameras are provided, the processor 26 may transmit, to the terminal apparatus 18 owned by the target, an image that has been captured by one of the fixed cameras and that is the most effective in detecting the danger.

When transmitting the certain information to the terminal apparatus 18 owned by the target, the processor 26 may select information to be included in the certain information or process the certain information in accordance with an attribute (e.g., age, gender, a medical history, etc.) of the target. Since visual abilities can be different depending on age (e.g., due to cataract, glaucoma, etc.), for example, the processor 26 may adjust sharpness of an image included in the certain information or the like in accordance with age of the target. In addition, since awareness of danger can be different depending on gender and age, the processor 26 may select information to be included in the certain information in accordance with the gender and the age of the target. For example, the processor 26 may include only an image in the certain information, add text (e.g., text indicating a danger) to the certain information, or include both an image and text in the certain information in accordance with the gender and the age of the target.

Tenth Example

A tenth example will be described hereinafter.

For example, the biological information measuring apparatus 12 may measure biological information regarding a plant, and the device 16 may be operated on the basis of the measured biological information. The biological information to be measured is, for example, potential (e.g., potential including membrane potential etc.) or water content of the plant. Another piece of information may be measured as the biological information, instead.

In a case where biological information regarding a plant is being measured, for example, if the plant grows more rapidly by playing music near the plant than when music is not played, the processor 26 of the information processing apparatus 10 causes the device 16 to play music such that biological information (e.g., a potential) measured while music was being played continues to be measured. Alternatively, the processor 26 may control a method for giving water and fertilizers to the plant. For example, the processor 26 may give water and fertilizers to plant such that the biological information continues to be measured in the plant.

In addition, the processor 26 may detect changes in a state of the plant on the basis of the biological information measured in the plant and display information (e.g., an image, text, etc.) according to the changes on a display of an apparatus such as the terminal apparatus 18. The processor 26 may display the information according to the changes on the display while personifying the plant, instead.

The processor 26 may determine, on the basis of the biological information measured in the plant, whether the plant has a disease and display a result of the determination on a display of an apparatus such as the terminal apparatus 18.

Water content of a living thing changes over time, and biopotential reflects the changes. The biological information measuring apparatus 12 may measure the biopotential, and the processor 26 of the information processing apparatus 10 may detect an action or an abnormality of the living thing on the basis of the measured biopotential. If an abnormality is detected, for example, the processor 26 may transmit warning information indicating the abnormality to an apparatus such as the terminal apparatus 18. If biopotential of a person is measured and an abnormality is detected in the person on the basis of the biopotential, for example, warning information is transmitted to the terminal apparatus 18 owned by the person and displayed on the display of the terminal apparatus 18.

In general, water tends to be distributed evenly over the entirety of a person's body in the morning and gradually accumulates in a lower part of the person's body during the day as the person moves around. Biopotential reflects such changes in water content. The processor 26 of the information processing apparatus 10 may measure biopotentials at various positions on a person' body and measure time on the basis of changes in biopotential. For example, the changes in the biopotential may be used as a clock or a timer.

In addition, the processor 26 of the information processing apparatus 10 may measure biological information (e.g., brain waves etc.) regarding an animal other than a person and estimate a state (e.g., a disease) of the animal or an environment in which the animal exists.

The processor 26 of the information processing apparatus 10 may detect a type of living thing that is wearing the biological information measuring apparatus 12.

The size of a skull, for example, differs between a person and an animal other than a person. When the biological information measuring apparatus 12 includes a band which make the biological information measuring apparatus 12 wearable on the head and is worn on the head using the band, the processor 26 may detect the length of the band using a sensor or the like and detect a type of animal that is wearing the biological information measuring apparatus 12 on the basis of the length of the band. More specifically, since the size of the skull differs between a person and a dog, the length of the band accordingly differs. The processor 26 detects the length of the band and determines whether a living thing that is wearing the biological information measuring apparatus 12 is a person or a dog.

In another example, when the biological information measuring apparatus 12 is an apparatus worn on the ears of a living thing, the processor 26 may detect the length of hair on the ears on which the biological information measuring apparatus 12 is worn using a sensor or the like and detect a type of animal that is wearing the biological information measuring apparatus 12 on the basis of the length of the hair.

In yet another example, since body temperature differs between types of living things, the processor 26 may measure body temperature of a living thing that is wearing the biological information measuring apparatus 12 and identify a type of living thing on the basis of the body temperature.

In yet another example, since height and weight differ between types of living things and a resistance value accordingly differs, the processor 26 may identify a type of living thing that is wearing the biological information measuring apparatus 12 on the basis of the resistance value.

A type of living thing (e.g., a person, a dog, a plant, etc.) may be associated with biological information measured in a living thing. The biological information measuring apparatus 12 may make the association, or the information processing apparatus 10 may make the association. In doing so, a type of living thing in which certain biological information has been measured can be identified. When a type of living thing in which biological information has been measured is identified as described above, information indicating the identified type may be associated with the biological information.

Animals may communicate with each other using biological information such as brain waves. For example, persons, or a person and an animal other than a person (e.g., a dog), may communicate with each other using biological information. When a type of living thing in which biological information is identified as described above, the processor 26 may change, for example, a method for converting brain waves in the communication.

Eleventh Example

An eleventh example will be described hereinafter. In the eleventh example, a stimulus is given to a living thing, and the processor 26 of the information processing apparatus 10 associates stimulus information indicating the stimulus and biological information measured in the living thing with each other. The stimulus information and the biological information associated with each other are stored, for example, in the memory 24 of the information processing apparatus 10. Plural pieces of biological information may be associated with stimulus information, instead. Brain waves, pulse rate, blood pressure, complexion, and body temperature, for example, may be associated with stimulus information.

The stimulus is, for example, an image such as a still image or a moving image, an environment, a taste, or the like. An image indicating an emotion, an image or an environment that induces fear, or a healing image or environment, for example, is given as the stimulus. Such an image is, for example, a virtual image based on a virtual reality (VR) technique. An image showing an actual object may be used, instead. The stimulus may be an electrical stimulus given by an electrode provided for the biological information measuring apparatus 12, instead.

When a person is looking at an image, for example, the biological information measuring apparatus 12 measures biological information (e.g., brain waves) in the person and associates the image and the biological information with each other. The brain waves to be measured are brain waves emitted from the left brain, brain waves emitted from the right brain, or brain waves emitted from both the left and right brains.

The processor 26 may associate words (i.e., sound information) uttered by a person while a stimulus is being given to the person with stimulus information and biological information. The processor 26 may also associate information indicating a motion of the person with the stimulus information and the biological information.

A virtual image such as a VR image may be a background image captured in daily life of a person, and surrounding sounds may be played back when the VR image is displayed.

Alternatively, an image based on past experience of a person in whom biological information has been measured may be used as the VR image. The person may be inquired of the past experience in advance (e.g., a questionnaire).

If biological information measured in a person who is looking at a VR image greatly changes, the processor 26 may associate a corresponding piece of the biological information with the stimulus information as an effective biological information. If the amount of change in the biological information becomes larger than or equal to a threshold, for example, the processor 26 associates a corresponding piece of the biological information with the stimulus information as effective biological information.

Order in which the stimulus information is given to a person may be controlled. For example, visual information that a person dislikes may be given to the person, and then audio information, olfactory information, or sensation information that the person likes may be given to the person. The processor 26 may associate biological information measured at this time and a corresponding piece of the stimulus information with each other.

The processor 26 may change the stimulus information given to a person in accordance with changes in the measured biological information.

Figure 40:
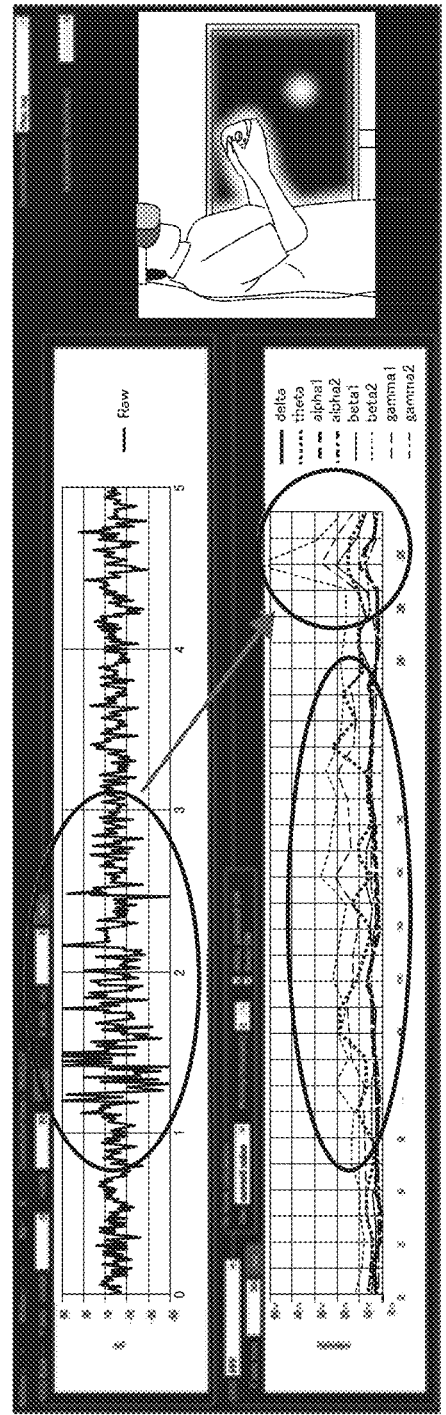
FIG. 40 illustrates brain wave data of a person who is viewing a VR image containing a monster-like creature.

For instance, FIG. 40 illustrates brain waves of a person who is viewing a VR image containing a monster-like creature. Change is observed in the brain waves between a mental state of nervousness before the monster-like creature appears, and a mental state of surprise when the monster-like creature appears, as shown in FIG. 40. Such change can be detected and the processor 26 may change the stimulus information accordingly.

The processor 26 may change speed at which the VR image is played back, a point of view for the VR image, coloring of the VR image, or image quality or a focal point of the VR image.

The stimulus information and the biological information associated with each other may be used for digital marketing (e.g., video production, attraction, a product such as a device, etc.) or digital healthcare (e.g., a service for evaluating a lifestyle on the basis of degrees of stress and refreshment recorded daily etc.).

Twelfth Example

The biological information measuring apparatus 12 may be shared by plural persons or the like. For example, person A may use the biological information measuring apparatus 12, and then person B may use the biological information measuring apparatus 12 that has been used by person A.

For example, if a living thing (e.g., a person) that is wearing a biological information measuring apparatus 12 of a contact type (i.e., an apparatus that measures biological information with an electrode or a sensor in contact with a living thing such as a person) is replaced by another living thing, the biological information measuring apparatus 12 may output information indicating the change or information for encouraging cleaning of the biological information measuring apparatus 12. The outputting of the information refers to, for example, displaying of the information on the display, issuing of the information from the speaker as a sound, or both.

When a microphone is provided for the biological information measuring apparatus 12, for example, the biological information measuring apparatus 12 recognizes a person who is using the biological information measuring apparatus 12 on the basis of the person's voice input from the microphone and determines whether a person who is using the biological information measuring apparatus 12 has been replaced by another person. A camera provided for the terminal apparatus 18 or the like may capture an image of a person who is using the biological information measuring apparatus 12, and the biological information measuring apparatus 12 may recognize the person on the basis of the captured image.

In another example, when the information processing apparatus 10, the biological information measuring apparatus 12, the terminal apparatus 18, a server, or the like manages an account of a person who is using the biological information measuring apparatus 12 and the account has been switched to another account, the biological information measuring apparatus 12 may determine that the person who is using the biological information measuring apparatus 12 has been replaced by another person.

By outputting information indicating that a person who is using the biological information measuring apparatus 12 has been replaced by another person, the person who is going to use the biological information measuring apparatus 12 recognizes that another person has been using the biological information measuring apparatus 12. As a result, the person who is going to use the biological information measuring apparatus 12 recognizes, for example, that the biological information measuring apparatus 12 needs to be cleaned. The same holds when information for encouraging cleaning of the biological information measuring apparatus 12 is output.

In addition, a sensor or the like that detects completion of cleaning of the biological information measuring apparatus 12, for example, may be used. When a sensor (e.g., a sensor that detects alcohol) that detects completion of alcohol cleaning of an electrode or a sensor for measuring biological information is used and the biological information measuring apparatus 12 is about to be used (e.g., the biological information measuring apparatus 12 is turned on) without the electrode or the sensor cleaned with alcohol, for example, the biological information measuring apparatus 12 outputs information indicating that the biological information measuring apparatus 12 has not been cleaned. Alternatively, the biological information measuring apparatus 12 may remain turned off. When the biological information measuring apparatus 12 is about to be used with the electrode or the sensor cleaned with alcohol, the biological information measuring apparatus 12 may or may not output information indicating that the biological information measuring apparatus 12 has been cleaned.

Thirteenth Example

Figure 24:
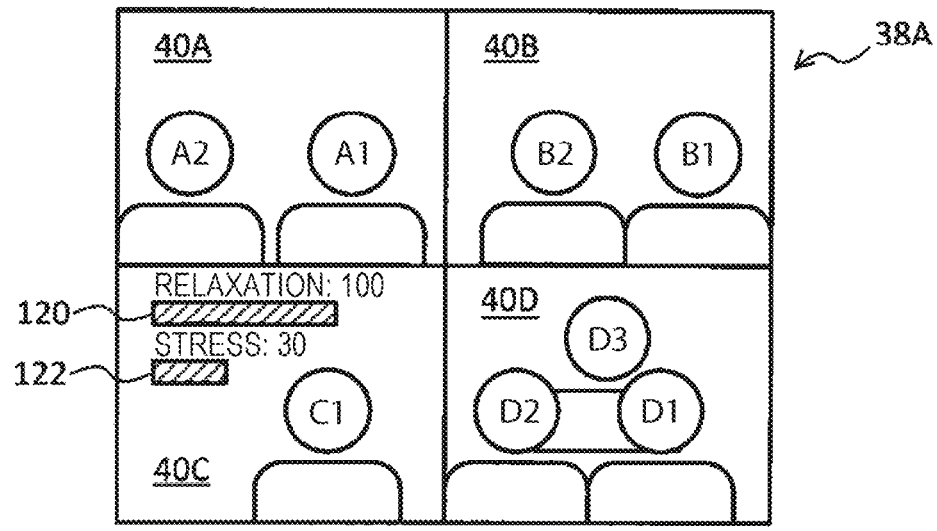
FIG. 24 is a diagram illustrating the screen.

A thirteenth example will be described hereinafter with reference to FIG. 24. FIG. 24 illustrates the screen 38A. The screen 38A is the same as that in the third example (refer to FIG. 12).

In the thirteenth example, information (e.g., an image of a bar, a value, etc.) indicating an emotion, an intention, a mental state, a psychological state, or the like is displayed. The processor 26 estimates the emotion, the intention, the mental state, or the psychological state on the basis of biological information regarding a user. For example, a bar or a value indicating a degree of concentration, relaxation, or stress is displayed. Bars or values may be displayed for all users, or a bar or a value may be displayed only for a user specified by a manager or the like.

Figure 41:
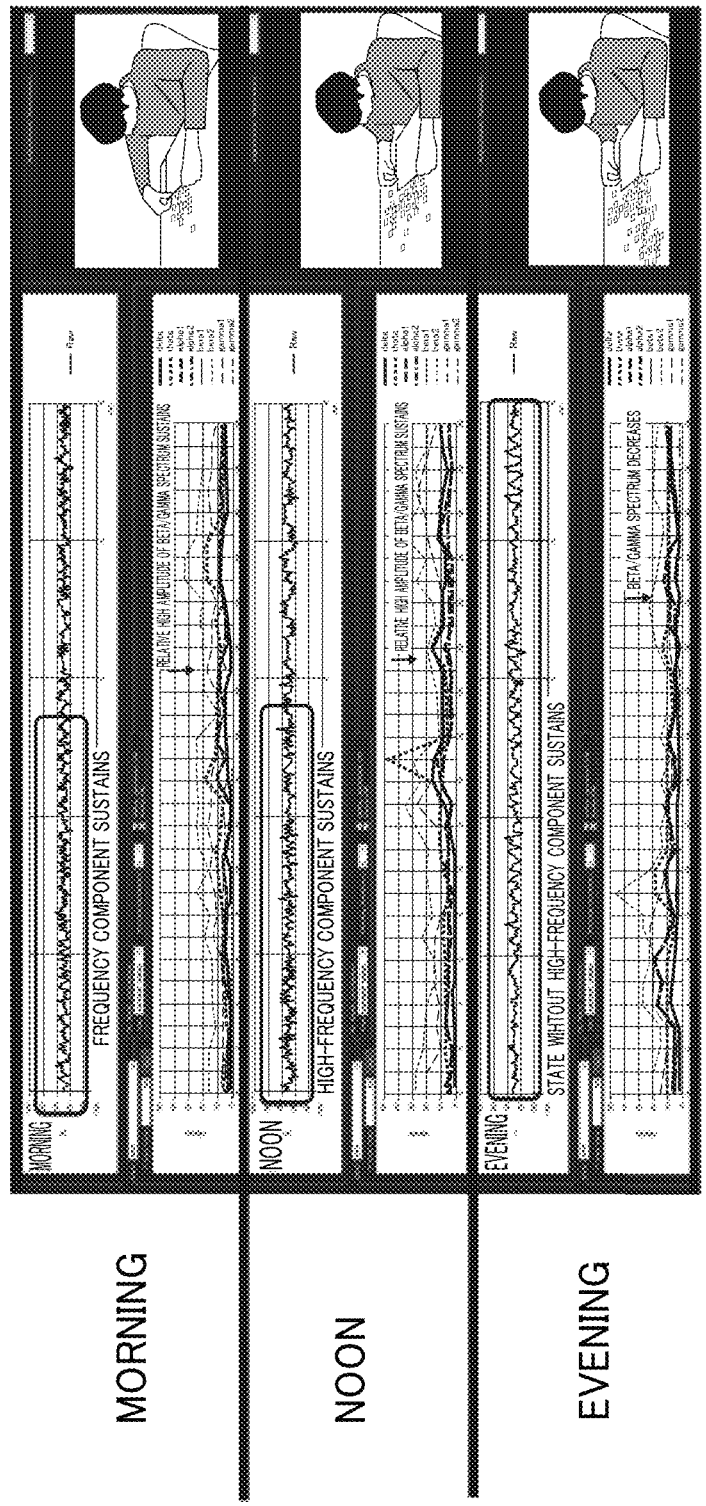
FIG. 41 illustrates brain wave data of a person performing a mental task (completing a white puzzle)

As an example, brain waves of a person performing a mental task (completing a white puzzle) in the morning, at noon, and in the evening, are illustrated in FIG. 41. It is found that the length of time for which the beta waves and the gamma waves are present shortens towards the evening, characterizing the extent of fatigue due to concentration.

Figure 42:
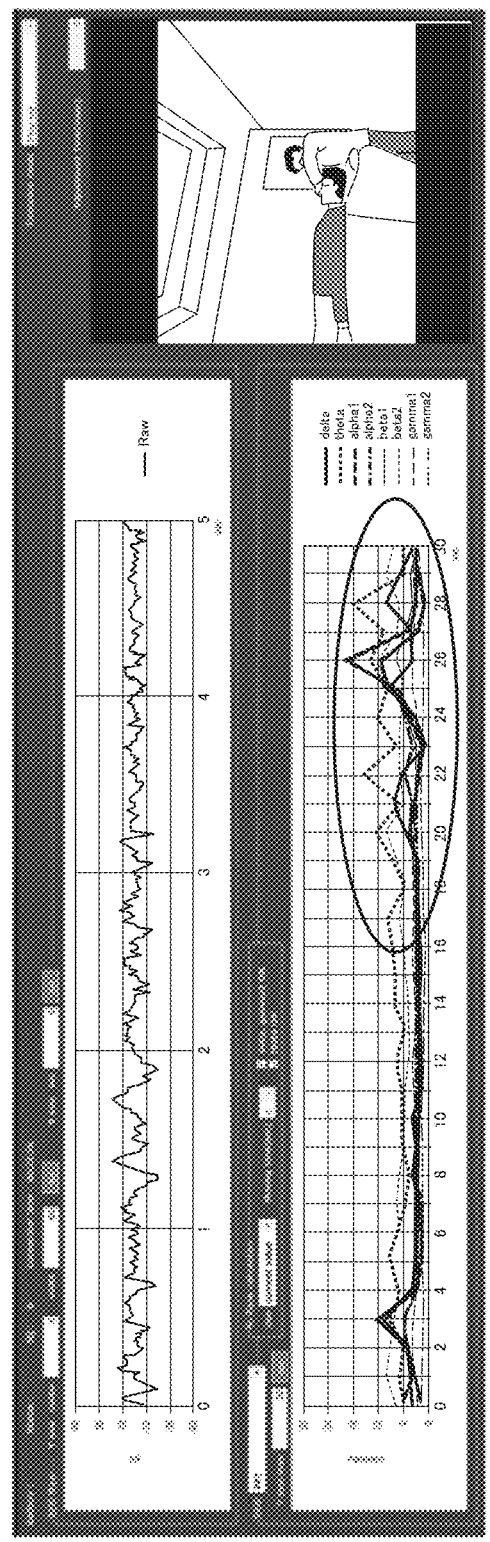
FIG. 42 illustrates brain wave data of a person receiving a head massage.

As another example, brain waves of a person experiencing a head massage is illustrated in FIG. 42. It is found that rising in theta wave range is observed, and then rising in the alpha range occurs as the person dozes off and becomes unconscious, characterizing degrees of relaxation effects.

Figure 43:
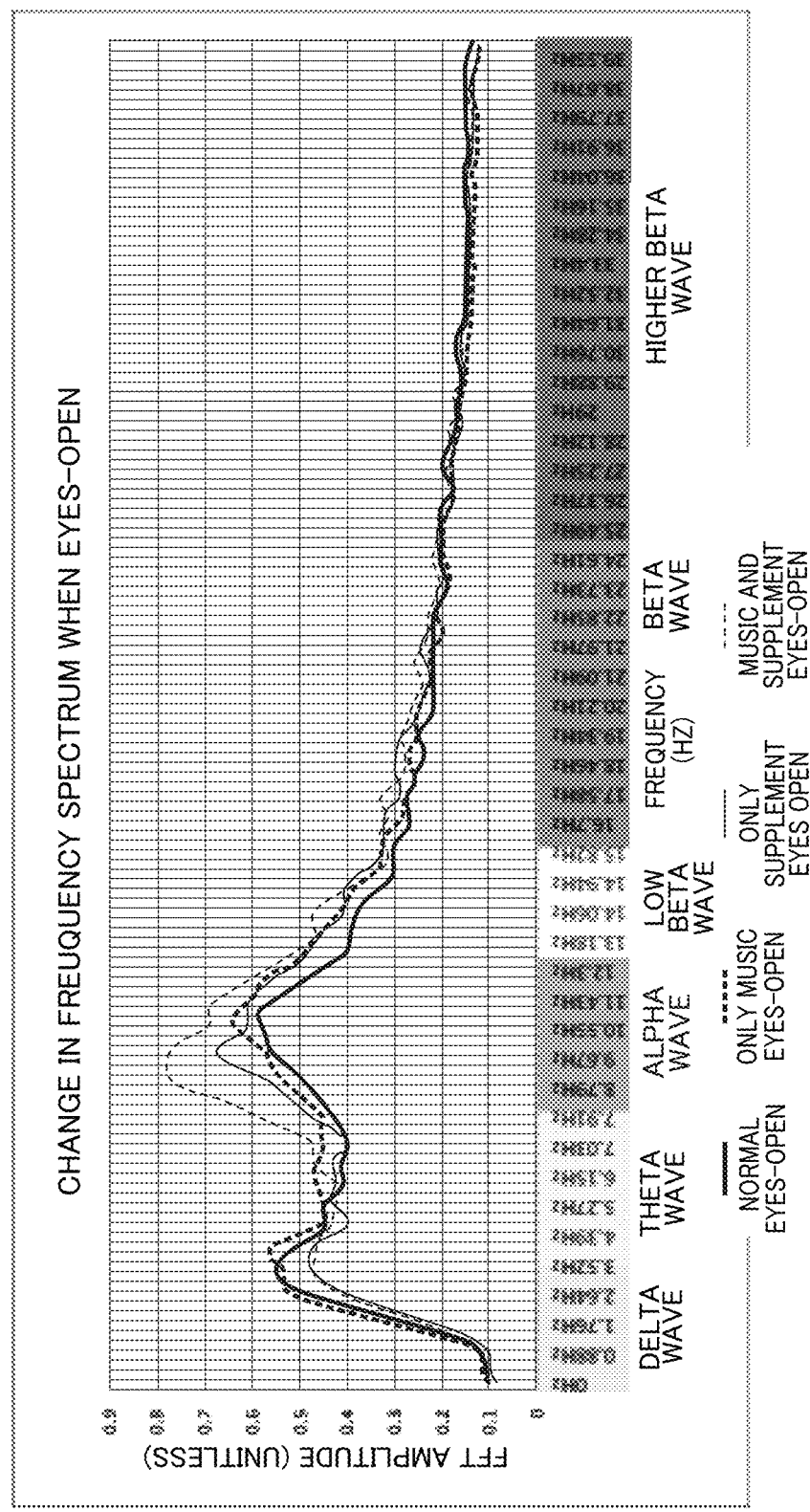
FIG. 43 illustrates brain wave data of a person listening to music or taking a supplement.

As another example, brain waves of a person listening to a music or taking a supplement is illustrated in FIG. 43. The brain waves are measured for four minutes with eyes open for each case of (a) base case with eyes open, (b) only listening to music with eyes open, (c) only taking supplements with eyes open, and (d) both listening to music and taking supplements. The music used is of the type having 963 Hz. The supplement is based on measurement taken at three minutes after taking of five drops (25 mg) of CBD. Fast-Fourier Transform is performed per second for the frequency ranges of each of the brain wave ranges. It is found that with (b), (c) or (d), the FFT intensity in the alpha wave band increased, with the most increase being observed in case (d) with increase of 43% compared to the base case (a) in 9.67 Hz range.

Figure 44:
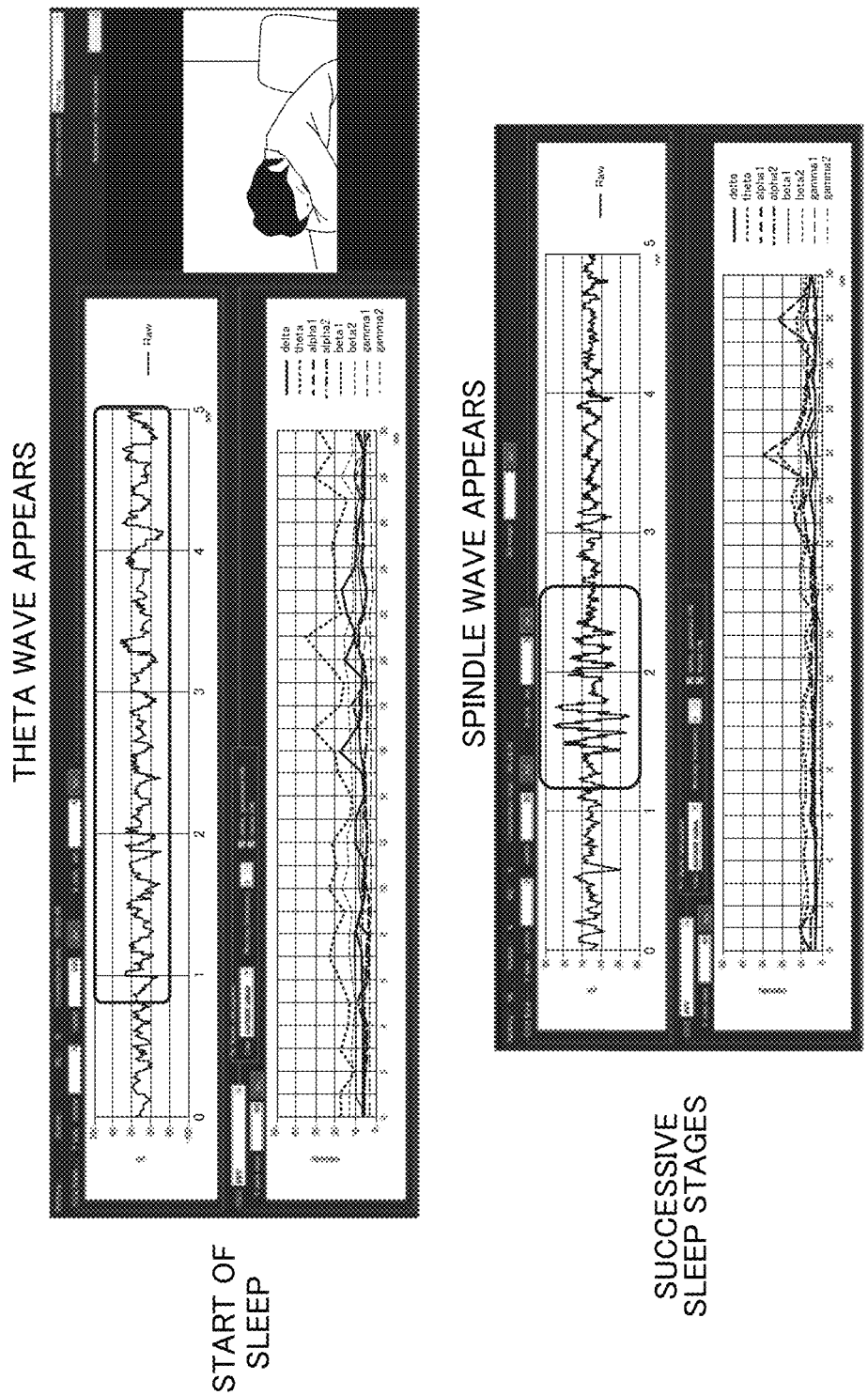
FIG. 44 illustrates brain wave data of a person undergoing beginning of sleep and successive sleep states.

As another example, difference in brain waves between beginning of sleep and as successive sleep states occur is illustrated in FIG. 44. When the sleep begins, theta waves begin to appear. As the sleep stage advances, spindle waves begin to appear. In this way, it is possible to characterize the depth of sleep and estimate the time that has passed after the onset of sleep.

Figure 45:
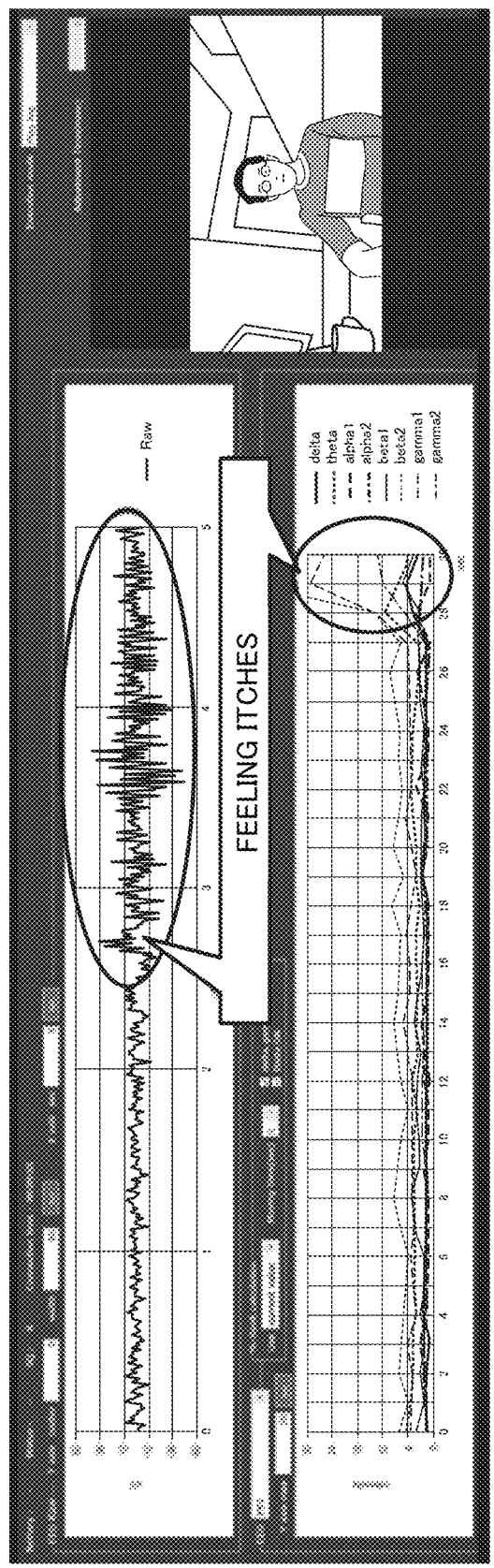
FIG. 45 illustrates change in brain waves when the user experiences itches.

As another example, the user's physiological events, such as desire for excretion or feeling of itches can be detected. FIG. 45 illustrates change in brain waves when the user experiences itches.

Characteristics of the brain waves such as the above may be converted to a bar or a value and displayed to the user. In this way, the internal state of the user may be visualized.

In an example illustrated in FIG. 24, bars and values indicating a mental state of user C1 are displayed. A bar 120 is an image indicating a degree of relaxation of user C1. A bar 122 is an image indicating a degree of stress of user C1. The degree of relaxation is "100", and the degree of stress is "30". The processor 26 calculates these values on the basis of biological information regarding user C1.

The processor 26 may identify an event that has contributed to a state of the user (e.g., an emotion, an intention, a mental state, a psychological state, etc.) and calculate a degree of contribution of the event to the state of the user. For example, the processor 26 identifies an event that has contributed to stress or recovery from the stress and display information indicating a degree of contribution on the screen 38A. In doing so, the user easily understands what kind of event and how much the event has affected the state of the user. For example, the processor 26 detects occurrence of an event using various sensors and estimates a change in the state of the user at the time of the event and states of the user before and after the occurrence of the event on the basis of biological information regarding the user. The processor 26 estimates a degree of contribution of the event to the state of the user, for example, on the basis of the change in the state of the user.

The processor 26 may store, in the memory 24, history information indicating histories of occurrence of events, biological information regarding the user before and after the occurrence of the events, changes in the biological information regarding the user, states of the user before and after the occurrence of the events, changes in the state of the user. The processor 26 may reproduce a past event on the basis of the histories indicated by the history information. For example, the processor 26 may record an event that has occurred around a time point at which the user has gotten relaxed and reproduce the same situation. For example, a target value of relaxation is specified, and the processor 26 reproduces a situation where the target value can be achieved. The processor 26 may reproduce the situation by combining together playback of music, display of an image or the like, an instruction to take an action, and the like. The processor 26 may record the histories while obtaining states of brain waves of the user, classifying the states of the brain waves, and associating the states of the brain waves with working and non-working hours (e.g., times other than time of sleeping). The processor 26 may also insert values and bars indicating states of relaxation and the like into an image of a meeting using a virtual camera.

Fourteenth Example

Figure 25:
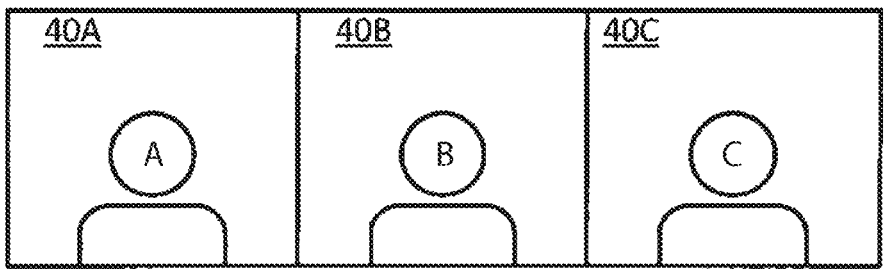
FIG. 25 is a diagram illustrating the screen.

A fourteenth example will be described hereinafter with reference to FIGS. 25 and 26. FIG. 25 illustrates, as with FIG. 17, the images of users A, B, and C. Information (e.g., brain waves etc.) indicating states of the users is also displayed while being associated with the users. It is assumed here, for example, that users A, B, and C are attending the same online meeting.

If all the users attending the online meeting, or a predetermined number or more of users, are in the same state (e.g., the same emotion, intention, mental state, or psychological state), for example, the processor 26 may display frames of images of the users in the same state in a certain color (e.g., red) or give a certain effect. The states of the users are estimated on the basis of biological information regarding the users.

Figure 26:
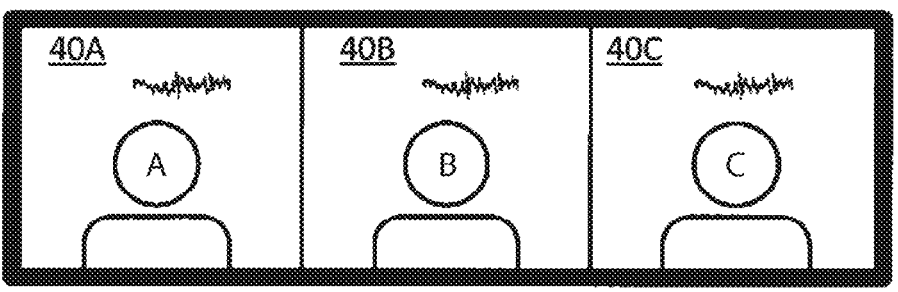
FIG. 26 is a diagram illustrating the screen.

When users A, B, and C are in the same state (e.g., an aroused state), for example, the processor 26 displays a frame surrounding the images of users A, B, and C in a certain color and gives a certain effect (e.g., a thicker frame) as illustrated in FIG. 26. In doing so, it can be indicated that users A, B, and C are in the same state. If all users attending an online meeting are in the aroused state, for example, such a color and an effect are given to show that the online meeting is in an enthusiastic mode.

As in the fourteenth example, information for collectively expressing states of plural users attending a meeting may be displayed, instead.

Fifteenth Example

A fifteenth example will be described hereinafter.

Data transmitted from the biological information measuring apparatus 12 to another apparatus (e.g., the information processing apparatus 10) may be data generated by performing processing such as an FFT, instead of raw data of biological information. In doing so, information that is included in raw data but that is not included in data generated by performing processing such as an FFT is prevented from leaking.

Alternatively, the biological information measuring apparatus 12 may encrypt information indicating a measured item of biological information (e.g., information indicating a channel or a part) and transmit the encrypted information to another apparatus (e.g., the information processing apparatus 10). In doing so, it becomes difficult to identify the item indicated by the transmitted biological information, thereby improving security of the biological information.

When measured biological information or information obtained from the measured biological information is lent or sold to a user, the processor 26 may restrict use of the biological information or the information. The restriction may be achieved, for example, by deleting the information when a certain period of time elapses or making the user return the information to a provider of the information. A place where use of the information is performed, purposes of use of the information, or the like may also be defined.

Sixteenth Example

A sixteenth example will be described hereinafter.

In the sixteenth example, an artificial intelligence (AI) assistant that outputs sounds is used. The AI assistant performs processing or operates devices, for example, in accordance with biological information regarding a user or an instruction from the user. The AI assistant may be incorporated into a terminal apparatus owned by the user or an apparatus other than the terminal apparatus, such as the information processing apparatus 10 or a server.

For example, the processor 26 may change the volume of the sounds output from the AI assistant or speed at which the AI assistant speaks in accordance with biological information regarding the user.

More specifically, if the biological information regarding the user indicates the user's desire to feel relaxed, the processor 26 changes a sound output from the AI assistant to a sound that the user likes (e.g., a higher tone, a lower tone, speed of speech, etc.) or voice of a family member of the user.

If the biological information regarding the user indicates that the user is in a hurry, the processor 26 causes the AI assistant to speak faster or output sounds more promptly.

When the user studies using the sounds output from the AI assistant, the processor 26 may control the AI assistant such that the AI assistant outputs the sounds at a speed or with a volume effective for the user in the study. An effect of the study by the user is estimated on the basis of biological information regarding the user. For example, the processor 26 changes the speed or the volume of the sound output from the AI assistant on the basis of the biological information regarding the user.

If the user is attending an online meeting, a telephone conference, or the like, the processor 26 may estimate a state of a person with whom the user is talking on the basis of biological information regarding the person and change, on the basis of a result of the estimation, a sound uttered by the user to the person such that the sound uttered by the user becomes easier to understand for the person. If the user is angry and uttering a sound that might scare the person, for example, the processor 26 may make the sound gentler or express the user's intention with a figure, a sentence, or the like without transmitting the sound to the person. Such a process may be performed by the AI assistant.

In an online meeting or the like, a user (e.g., a first user) might be wearing a biological information measuring apparatus 12 but another user (e.g., a second user) with whom the first user is talking might not be wearing a biological information measuring apparatus 12. In this case, biological information regarding the first user is obtained, and biological information regarding the second user is not obtained. In this case, too, the biological information regarding the first user might change due to a change in a facial expression of the second user or a sound uttered by the second user, for example, if the first user can recognize the facial expression of the second user on a screen. If the biological information regarding the first user changes in this manner, the processor 26 determines that the biological information regarding the first user has changed because of the second user. The processor 26 may estimate a state (e.g., an emotion, a mental state, a psychological state, etc.) of the second user on the basis of the determination. If the second user have a painful look, for example, the first user who is looking at the second user's face might feel sorry. The processor 26 therefore estimates the state of the second user on the basis of the biological information regarding the first user. The AI assistant may inform the first user of how to deal with the second user in such a state.

When voice is given to a character in an animation or a drama or a movie is dubbed, a user who is authorized to determine a voice to be used may listen to voices of some voice actors, and the processor 26 may determine a voice actor to be employed on the basis of biological information regarding the user. If biological information indicating satisfaction is obtained from the user, for example, the processor 26 determines a voice actor who has uttered a corresponding sound as the voice actor to be employed. If biological information indicating a sense of incongruity or discomfort is obtained from the user, the processor 26 may introduce another voice actor to the user.

Seventeenth Example

A seventeenth example will be described hereinafter.

The present exemplary embodiment may be applied to a content service such as a video game. For example, the video game may be provided for a user through a terminal apparatus owned by the user or through another device (e.g., a gaming device). The video game may be an online game or provided by executing a program installed on the terminal apparatus or the gaming device. A storage medium storing a program for the video game may be used, and the video game may be provided by executing the program using the terminal apparatus or the gaming device.

For example, the biological information measuring apparatus 12 measures biological information regarding the user while the user is playing the video game. The processor 26 may change stories, scenes, sounds, images in the video game in accordance with emotions of the user obtained from the biological information.

If biological information indicating a level of fear higher than or equal to a predetermined threshold is measured in a user who has trouble in playing scary video games or experiencing other scary things, for example, the processor 26 omits violent scenes, reduces sound volume, simplifies dramatic effects, or makes expressions easier to understand.

If biological information indicating a level of fear higher than or equal to the predetermined threshold is not measured in a user who likes scarier scenes, on the other hand, the processor 26 may change how the video game is presented such that more violent scenes and scarier scenes are included.

Tastes of a user are set before the video game starts. The processor 26 may change how the video game is presented in accordance with health problems and age of the user as well as biological information. The processor 26 may also change how the video game is presented for educational reasons.

The processor 26 may determine a state of a user at predetermined time intervals on the basis of biological information regarding the user. As a result, scenes can be changed in real-time, and the video game proceeds without causing discomfort or a sense of incongruity in the user. Scenes that are unchangeable for the sake of stories of the video game may also be set.

If it is determined that the user is feeling that the video game is too difficult or too easy, the processor 26 may change a level of difficulty of the video game in accordance with the feeling. For example, the processor 26 may change an action level of AI that controls enemies of the user or the number of enemies. When a mystery game is being played, the processor 26 may change the number of clues for unpuzzling a mystery. Alternatively, the processor 26 may change setting values of a character controlled by the user, such as attack power and defense power.

The processor 26 may notify the user of a change in the level of difficulty based on the biological information. In doing so, the user recognizes, for example, the level of difficulty of the video game he/she has cleared. In this case, how long the user has played the video game, changes in the user's emotion during the play, the level of difficulty of the video game, and the like may be displayed using figures such as graphs.

If a state that the user desires to achieve is achieved while the user is playing the video game, information indicating the state may be stored in the memory 24 of the information processing apparatus 10 as history information. The processor 26 may change scenes or the level of difficulty of the video game such that the state that the user desires to achieve is achieved. If the user sets, to the information processing apparatus 10, information indicating that the user desires to be freed from stress and refresh, for example, the processor 26 may change the scenes or the level of difficulty of the video game such that the user achieves the state. For example, the processor 26 may change a scene in the video game to one including a blue sky and a plain. In another example, the processor 26 may make an enemy weaker so that a character controlled by the user can easily defeat the enemy.

Eighteenth Example

An eighteenth example will be described hereinafter.

In the eighteenth example, the biological information measuring apparatus 12 is a hearable and worn on the user's ears. The hearable may have a sound assistance function. The sound assistance function is a function of assisting the user on the basis of biological information regarding the user. The sound assistance function may be achieved by AI.

A process in the eighteenth example will be described hereinafter.

First, the hearable, which is an example of the biological information measuring apparatus 12, measures biological information (e.g., an electrocardiographic waveform, brain waves, a myoelectric waveform, skin potential, etc.) at the user's ears (e.g., ear canals) and also measures the user's voice. The hearable stores the biological information and sound information in chronological order while associating the biological information and the sound information with each other. These pieces of information may be stored in the hearable, a terminal apparatus owned by the user, or the information processing apparatus 10. It is assumed here, for example, that these pieces of information are stored in the information processing apparatus 10.

The processor 26 of the information processing apparatus 10 determines whether a fluctuation has occurred in the biological information regarding the user. When the biological information is brain waves, for example, a fluctuation may be an abnormal epileptic wave, and when the biological information is an electrocardiographic waveform, a fluctuation may be a waveform indicating an abnormality in myocardia, such as arrhythmia.

If detecting a fluctuation in the biological information regarding the user, the processor 26 records a time at which the fluctuation has occurred, a place where the user is located at the time, and information indicating a state of the user (hereinafter collectively referred to as "context information"). The processor 26 may remove noise and determine whether the fluctuation derives from a mental or physical stimulus response.

If the fluctuation (i.e., a change in a mental or physical stimulus response) indicates a dangerous condition, the processor 26 controls a sound function of the hearable. The dangerous condition is, for example, a case where a symptom of a heart disease has occurred (e.g., when arrhythmia has been detected from pulse, which is the biological information), a case where the user has fallen down (e.g., when a fall of the user has been detected on the basis of a myoelectric waveform, which is the biological information, or data from an acceleration sensor), a case where the user has swallowed something (e.g., when an irregular waveform is included in a myoelectric waveform, which is the biological information, and it has been detected on the basis of the irregular waveform that the user might have swallowed something), or the like.

The processor 26 transmits the context information, the biological information, and the sound information to an apparatus (e.g., a PC etc.) provided in a predetermined place (e.g., a hospital etc.). At this time, the processor 26 transmits, to the apparatus, the context information, the biological information, and the sound information measured around the time (e.g., in a predetermined period of time) at which the fluctuation has occurred The processor 26 may control sounds output from the hearable on the basis of the context information, the biological information, and the sound information. For example, the processor 26 controls playback speed of content, which is played back by the hearable. More specifically, the processor 26 changes speed at which a moving image for learning is played back or speed at which an electronic book is read aloud. Alternatively, the processor 26 may stop the playback of the content. Alternatively, the processor 26 may play back content (e.g., a subject, a comic book, a song, etc.) that suits the user's tastes. Alternatively, the processor 26 may execute an automatic call function. The automatic call function herein refers to a function of automatically calling a predetermined emergency contact number or sending a message to or a predetermined emergency address (e.g., a family member, a regular doctor, etc.). Calls may be made or messages may be sent to plural persons at once or gradually. The processor 26 may change a person to be contacted in accordance with seriousness of a condition of the user. The user may also be notified of his/her own condition.

The sound assistance function may be switched for each hearable or user account. A function of determining whether to execute the sound assistance function on the basis of biological information may also be provided. The sound assistance function of the hearable may be executed without using biological information. Scene where the sound assistance function based on biological information is executed may be limited to scenes where initial symptoms of a disease are examined or a reading function for a content service or the like. A function of setting such a limitation may also be provided.

The processor 26 may cause an AI that achieves the sound assistance function to learn the context information, the biological information, and the sound information.

For example, the processor 26 may accumulate sound information while the user is talking in a relaxed state and cause the AI to learn the sound information. For example, the AI may create a voice assistant sound optimized for biological reactions using a technique of sound synthesis or sound adjustment and read the voice assistant sound aloud.

In another example, the processor 26 may accumulate sound information while the user is talking in a stressed state and cause the AI to learn the sound information. For example, the AI may create a voice assistant sound optimized for recovery of calmness using a technique of sound synthesis or sound adjustment and read the voice assistant sound aloud.

In yet another example, the processor 26 may accumulate sound information while the user is tense and cause the AI to learn when, where, and how the user has become tense. For example, the AI may create a voice assistant sound optimized for recovery of calmness using a technique of sound synthesis or sound adjustment and read the voice assistant sound aloud.

In yet another example, the processor 26 may convert the user's voice into text, accumulate data regarding the text in chronological order along with information indicating the user's emotion, and cause the AI to learn the data and the information. The data and the information may be stored in a memory, instead. The emotion may be selected by the user, instead. The processor 26 may change the size or color of the text or the like in accordance with the user's voice. The AI may create a voice assistant sound optimized for recovery of calmness using a technique of sound synthesis or sound adjustment and read the voice assistant sound aloud.

For example, the processor 26 stores sound information regarding the user obtained from a terminal apparatus (e.g., a smartphone, a PC, etc.) owned by the user, information regarding icons, letters, pictures, and the like input by the user, and biological information measured in the user while associating these pieces of information with one another. The processor 26 converts the biological information regarding the user into emotion index data indicating an emotion, stress, concentration, relaxation, burden, understanding, proficiency, interest, or the like.

Electrodermal activity, for example, may be used as a parameter indicating a mental activity state. A skin potential level (SPL), which is a direct current component of skin potential activity (SPA), may be used, instead. The SPL usually shows a large negative value when the user is highly aroused (i.e., excited) and a large positive value when the user is sleepy or relaxed. Skin potential response (SPR), which is an alternating current component of the SPA, may be used, instead. The SPR frequently occurs due to stimuli based on changes in an external environment, such as a pain, a touch, a sound, and an image, deep breathing, body movement, a thought, and the like.

The processor 26 displays information indicating the state of the user obtained from an interface such as a camera or a keyboard, a degree of the state indicated by the emotion index data (e.g., an emotion, stress, concentration, relaxation, burden, understanding, proficiency, interest, etc.), and a type of state. For example, the processor 26 changes display color, a type of font of letters, and the size of letters in accordance with the degree of the state and the type of state. For example, the processor 26 may change a speech style (e.g., pleasure, anger, sadness, fear, kindness, etc.) or a tone of voice (e.g., emphasis, speed, pitch, intonation, volume, etc.) in accordance with a stimulus response (e.g., relaxation, stress, tension, etc.) in a reading function achieved by known software. The processor 26 may change the volume or speed of voice of the reading function in accordance with the degree of the user's emotion.

The above examples may be applied, for example, to an electronic book, movie content (e.g., includes content delivered on the Internet), an electronic learning material, a tool for an online meeting, or the like.

In yet another example, when a document or a material is created using a function of changing the size or color of letters and figures in accordance with biological information regarding the user, the document or the material can lack consistency if the function is used all the time. The processor 26, therefore, need not change the size or color of letters and figures in accordance with the biological information in certain areas of the document or the material. In other words, the processor 26 may change, in accordance with the biological information regarding the user, the size or color of letters and figures in areas where such changes are permitted.

If words written in the document or the material are read aloud using the reading function, the processor 26 may change the volume and speed of the reading in accordance with the biological information regarding the user. The speed of the reading may be limited to a certain range so that the reading does not become too fast or too slow.

Time taken to complete a process for determining an emotion, a mental state, or a psychological state on the basis of biological information and time taken to complete measurement of an emotion, a mental state, or a psychological state can vary depending on a type of emotion, mental state, or psychological state. Time intervals of measurement of a degree of concentration or relaxation, for example, are 1 second, time intervals of measurement of a degree of interest, understanding, proficiency, an activity load, an emotion, or creativity are 1 to 5 seconds, and time intervals of measurement of comfort or discomfort are 5 or 10 seconds. These time intervals are just examples, and may change depending on the performance of the biological information measuring apparatus 12 or the like.

When the time intervals vary as described above, the processor 26 need not determine all of predetermined emotions, mental states, and psychological states and may determine only some predetermined emotions, mental states, and psychological states or limit time periods or scenes in which the determination is made. When the user is studying, for example, the processor 26 may determine only an effect of the study on the basis of the biological information regarding the user and need not determine other emotions. If the user is in a certain state (e.g., if the user has a certain disease such as an underlying disease), however, the processor 26 may determine all of the predetermined emotions, mental states, and psychological states all the time.

If the user has taken off the hearable but is wearing another biological information measuring apparatus 12, the processor 26 may determine an emotion, a mental state, or a psychological state on the basis of biological information measured by the other biological information measuring apparatus 12. If the user was wearing a hearable and a smartwatch and has taken off the hearable, for example, an emotion, a mental state, or a psychological state of the user may be determined on the basis of biological information measured by the smartwatch.

Nineteenth Example

A nineteenth example will be described hereinafter. If biological information in a certain frequency band (e.g., brain waves in a certain frequency band) is measured in the above examples and biological information in a frequency band other than the certain frequency band is not measured, the processor 26 may estimate the biological information in the other frequency band. For example, the processor 26 estimates biological information that is of the same type as the measured biological information but that is in a frequency band other than a frequency band including the measured biological information.

If only a potential in a frequency band of alpha waves, which are an example of brain waves, is measured and a potential in a frequency band other than that of alpha waves is not measured, for example, the processor 26 estimates brain waves (e.g., brain waves other than alpha waves, such as beta waves) in the other frequency band that have not been actually measured and brain waves in the frequency band in which brain waves have not been clearly detected on the basis information measured by various sensors (e.g., a gyro sensor, an acceleration sensor, etc.), environment information (e.g., information indicating temperature, humidity, weather, a position, etc.), information regarding activity of the user (e.g., information indicating exercise, desk work, sleep, etc.), information indicating a disease of the user, and/or information indicating a history of measurement of the measured alpha waves (e.g., information indicating waveforms, periods, and amplitude of the alpha waves) at the time of the measurement. For example, the processor 26 estimates, on the basis of correlation between the above various pieces of information, brain waves in the frequency band that have not been measured. The processor 26 may output the estimated brain waves in the other frequency band to a terminal apparatus or the like. For example, the estimated brain waves in the other frequency band are displayed on a display of the terminal apparatus. At this time, the measured brain waves (e.g., alpha waves) in the frequency band and the estimated brain waves (e.g., beta waves) in the other frequency band may be displayed as graphs having the same scale (e.g., graphs whose horizontal axes represent time and vertical axes represent potential). The processor 26 may output the estimated brain waves in the other frequency band as candidates for brain waves in the frequency band. When alpha waves have not been measured and only beta waves have been measured, too, the alpha waves may be estimated.

When biological information in plural frequency bands have been measured, the processor 26 may estimate, on the basis of the biological information in the frequency bands, biological information in another frequency band that has not been measured. When alpha waves and beta waves have been measured and other brain waves have not been measured, for example, the processor 26 may estimate, on the basis of the measured alpha waves and beta waves, brain waves in a frequency band other than ones including the alpha waves and the beta waves.

When plural candidates have been estimated, the processor 26 may display the candidates on the display of the terminal apparatus or output a sound indicating that the candidates have been estimated. The processor 26 may change order in which the candidates are displayed or display scores on the basis of probabilities or possibilities of occurrence of the candidates.

When a hearable measures brain waves, for example, it might be difficult to detect biopotentials caused at positions on the head relatively far from the ears. In this case, brain waves in a frequency band that have not been measured can be estimated on the basis of brain waves in another frequency band that have been measured or another piece of information (e.g., environment information or information regarding the user).

Whether to enable or disable a function of estimating biological information in a frequency band that has not been measured may be set by the user. If the user enables the function using the terminal apparatus or the like, for example, the function is executed. If the user disables the function using the terminal apparatus or the like, the function is not executed. Because biological information that has not been measured (e.g., brain waves in a frequency band that have not been measured) might not be actually caused in the user's brain, the function can be disabled in such a case.

Twentieth Example

A twentieth example will be described hereinafter.

When brain waves or the like are used for communication between persons as a BMI, information to be communicated is identified, and means for communicating the information is provided.

For example, a communication target is extracted and information to be communicated is identified. A person who transmits the information then notifies a person who receives the information of the information. Only one communication target (a person who receives information) may be provided for a single person who transmits information, or plural communication targets (e.g., multiple communication targets) may be provided for a single person who transmits information. The information to be communicated is information regarding a thought or an intention of a person or state information and may be, for example, approval, agreement, disagreement, rejection, hesitation, confusion, etc. When information is provided for a person, the person transmits his/her thought about the information, namely whether he/she approves the information, to a person who receives the information. A method for transmitting information to a person is a method for giving a sensory stimulus, such as transmission of information by sound, transmission of information by light, or transmission of information by vibration. More specifically, in the case of a hearable, for example, measurement of biological information such as brain waves (measurement of information to be communicated) and transmission of information by sound can be achieved simultaneously using the ears, that is, the BMI can be achieved without preparing various devices. The sound may be language information, but may be musical tones, chimes, or the like, instead, insofar as what the musical tones, the chimes, or the like mean is determined in advance. Two successive sounds of a chime may mean approval, for example, or different levels or degrees of an intention may be transmitted by changing pitch. A low chime may mean a low level of approval, and a high chime may mean a high level of approval. With the advent of such a BMI, communication between persons can be achieved by various methods based on biological information such as brain waves, in addition to conventional methods based on language that employ sound or a graphical user interface (GUI).

Figure 27:
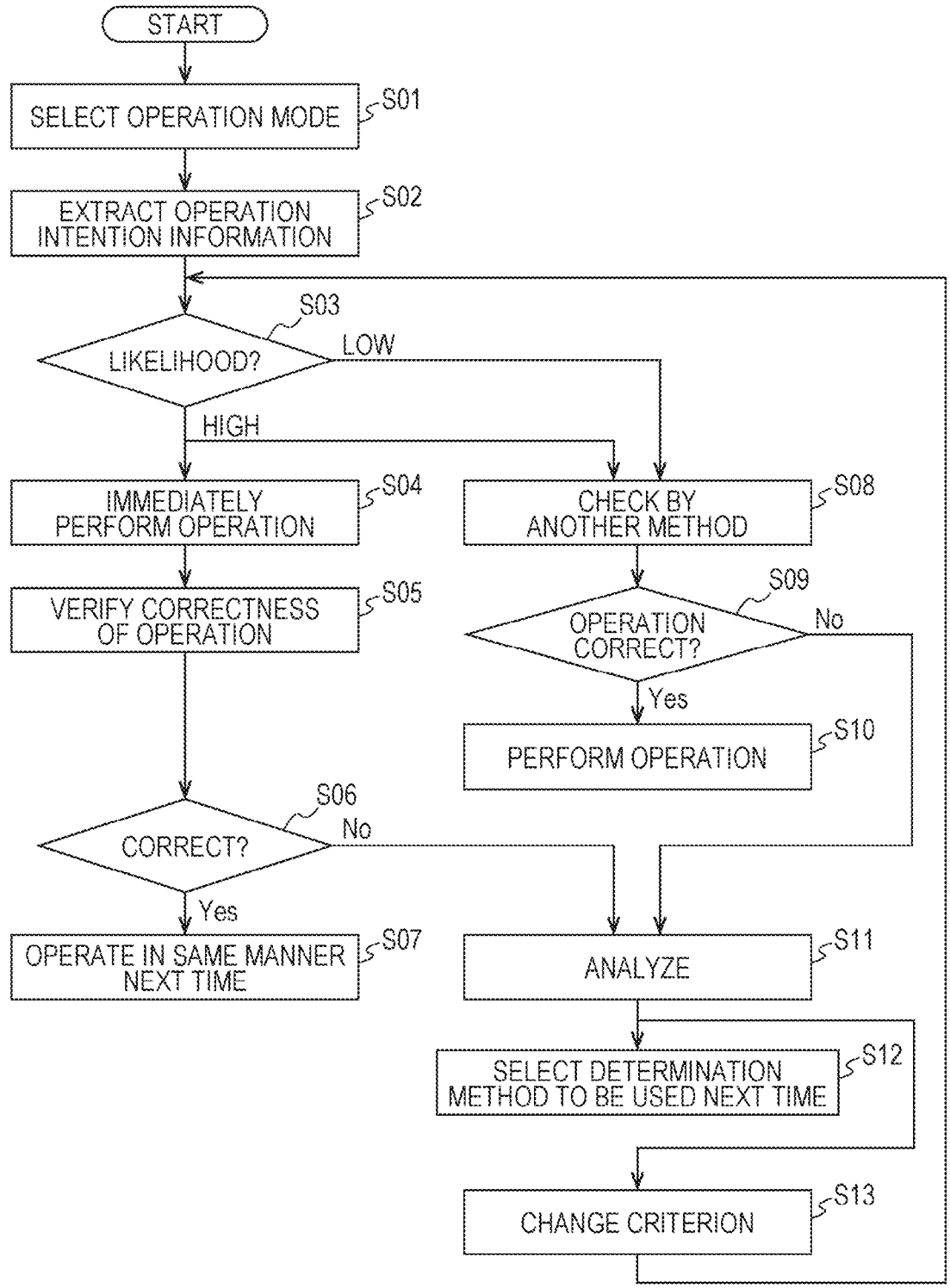
FIG. 27 is a flowchart illustrating a process in a twentieth example.
Figure 28:
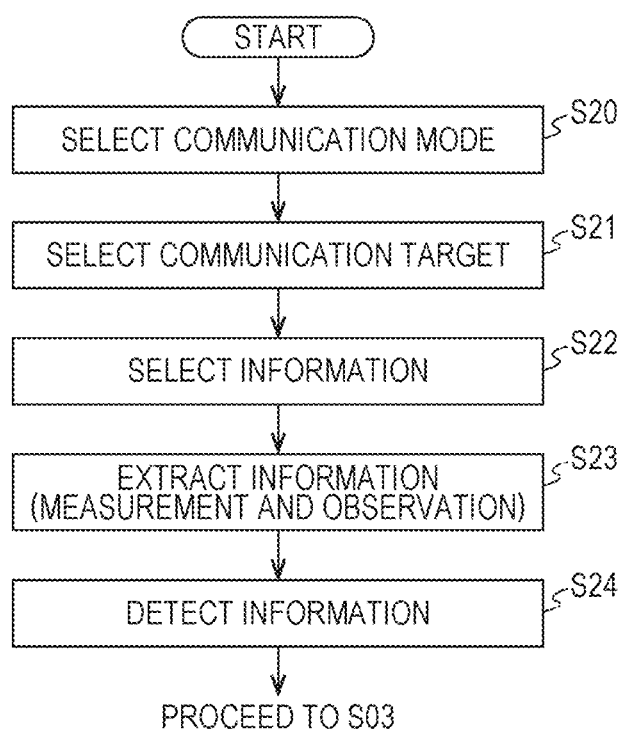
FIG. 28 is a flowchart illustrating another process in the twentieth example.

Specific examples of a process in the twentieth example will be described hereinafter with reference to FIGS. 27 and 28. FIGS. 27 and 28 are flowchart illustrating the specific examples of the process. FIG. 27 illustrates a process at a time when a device is operated. FIG. 28 illustrates a process at a time when persons communicate with each other.

As illustrated in FIG. 27, first, an operation mode is selected (S01), and operation intention information regarding a user is extracted and detected (S02). As a result, a device to be operated and an operation are extracted and associated with each other. A method for determining likelihood of an operation intention is presented to the user. If the likelihood of the operation intention is high (HIGH in S03), the operation is immediately performed on the device (S04). Correctness of the operation is then verified (S05). For example, the user performs the verification. If the operation is correct (YES in S06), the device will be operated in the same manner next time (S07). For example, the operation is set for the device, and the same operation will be performed next time. If the operation is not correct (NO in S06), the process proceeds to step S11. If the likelihood of the operation intention is low (LOW in S03), the operation intention is checked by another method (S08). If the likelihood of the operation intention is high, too, the operation intention may be checked by another method. Information indicating another method, for example, is displayed on a display or output from earphones of a hearable as a sound. As a result, the other method is presented to the user. If the checked operation intention is corrected (YES in S09), that is, if the checked operation intention matches an operation intention of the user, the device is operated (S10). If the checked operation intention is not correct (NO in S09), the process proceeds to step S11. In step S11, a reason why the operation intention is not correct is analyzed. For example, the user conducts the analysis. A next determination method (i.e., a method for determining an operation) is selected on the basis of a result of the analysis (S12). A criterion for determining an operation intention is changed (S13), and the processing in step S03 and the later steps reflects a new criterion. For example, a threshold registered in the management table is changed, and an operation intention is checked or the likelihood is determined, for example, on the basis of a new threshold. The user may perform the selection in the above process.

When persons communicate with each other, a communication mode is selected as illustrated in FIG. 28 (S20). The user sets an automatic selection mode or a manual selection mode, for example, and the communication mode is selected in accordance with the setting. Next, a communication target is selected (S21). In a mode in which the communication target is automatically selected, for example, an attendee of a meeting or the like is selected as the communication target. In a mode in which the user manually selects the communication target, for example, candidates for the communication targets are presented to the user using a sound output from the hearable or information displayed on a display, and the user selects the communication target. Next, the user selects information that may be transmitted to the communication target (S22). For example, the user selects the information that may be transmitted to the communication target among pieces of intention information and pieces of state information. In addition, the user may select information that the user does not desire to transmit to the communication target. Information indicating an emotion, for example, is selected as the information that the user does not desire to transmit to the communication target. Next, biological information is measured or observed, and intention information, state information, and the like are extracted on the basis of the biological information (S23). Next, information to be transmitted to the communication target is detected from the extracted intention information and state information and the like (S24). For example, a detection test is conducted in advance, and intention information, state information, or the like similar to information detected in the detection test (e.g., intention information, state information, or the like whose degree of similarity is higher than or equal to a threshold) is detected from the extracted intention information and state information and the like. Methods for detecting such information may be presented to the user. The detected intention information, state information, or the like is then transmitted to the communication target. For example, methods for transmitting such information may be presented to the user, and the user may select one of the methods. The methods include, for example, transmission by vibration (sound) and transmission by light. Information may be transmitted to the communication target using language, music, luminous signals, or the like. After the information is transmitted to the communication target, the user, who is a sender of the information, may be notified of completion of the transmission. The notification may be omitted, instead. After step S24 is performed, the processing in step S203 and the later steps illustrated in FIG. 27 may be performed.

The process in the twentieth example may be performed using a hearable. Because biological information is measured with the hearable worn on the user's ears, the user can be notified of various pieces of information while the biological information is being measured. Since the hearable is worn on the user's ears, the hearable has a natural appearance compared to an electroencephalogram worn on the head in order to measure brain waves or the like. The likelihood in the operation mode and the communication mode increases when a BCI based on the hearable is used.

In the above examples, a part or the entirety of the processes performed by the processor 26 of the information processing apparatus 10 may be performed by the processor 34 of the terminal apparatus 18 or the biological information measuring apparatus 12, instead. Alternatively, a part or the entirety of the processes may be performed by one or more apparatuses selected from the information processing apparatus 10, the terminal apparatus 18, and the biological information measuring apparatus 12.

Twenty-First Example

It is known that a person's state of mind (e.g. a decision) in regards to performing some task or solving a problem is reflected in the person's brain waves. For instance, when a person gives up performing some task, a theta wave increases, while when a person successfully solves a problem, an alpha wave increases (http://qlifepro.com/news/20211124/eeg-rhythm.html).

In the twenty-first example, the biological information measuring apparatus 12 measures the brain waves of the user, and the information processing apparatus 10 determines the situation that the user is in based on the measured brain waves and determine a type of intervention that may be needed by the user. Depending on the determination, an intervention device (e.g. the terminal apparatus 18) may perform the intervention by sending direct stimulation to the user (such as by electric stimulation or playing music) to affect the user's brain wave state so as to affect the user's state of mind, or to alert a third party (such as teachers, parents, user's superior) of the state of the user to provide appropriate help/intervention to the user.

More generally, the biological information measuring apparatus 12 acquires biological information of at least one user. Then, the information processing apparatus 10 determines a state of at least one user based on the biological information including at least brain waves of the at least one user, and historical information including at least one time series of context information indicating contexts under which measurements of the biological information at respective points time are made. Then, the state of the at least one user may be output to the at least one user.

The historical information may include at least one time series or action history of the user or time series of context information indicating contexts under which measurements of the biological information at respective points in time are made. For example, the context information may include: who makes the measurement, when the measurement is made, where the measurement is made, what is measured, why it is measured, how it is measured, what was the user doing before measurement is made, what was the user doing with other users before measurement is made, the environmental information such as the position, location, building, room, or temperature of the environment in which the user makes the measurement, scene or event that the user is participating in, or any of the other information indicating the context under which the measurement is made. Moreover, the historical information may be searchable (by the user or by other automatic processes such as AI) in terms of the type of contents it contains (e.g. searchable in terms of events or scene, for instance) and/or in terms of different time ranges. The historical information may be obtained by a camera, a microphone, or from information recorded on the internet.

The historical information may be classified according to plural different time series each having different interval of time between which the successive biological or context information are collected or different number of time points at which the biological or context information are collected, and at least one determination regarding the state of the at least one user is output based on analyzing the biological information and the historical information for each of the time series. For example, the state of the at least one user may be determined based on a combination of the biological information and the historical information collected at a first time series having time points that are apart by a first time interval (e.g., short time interval) and during a second time series having time points that are apart by a second time interval (e.g., long time interval).

Furthermore, a confidence for the determined state of the at least one user may be evaluated based on the similarity or sameness of the determined state for different time series. For instance, a higher confidence is assigned if the results from the short time interval and the long time interval are the same compared to if they are different. The determined state may be output to the user or be ignored based on the determined confidence.

Each time series may also be assigned a weight by the user depending on the context that the user is currently in and the determined states may be output to the user in the order of priority determined by the weights or a subset of the determined states may be output to the user depending on the weights.

In other words, whether to output which result from which time series may be determined based on the context information so that the result that best matches the user's expectation for a given situation determined by the context may be output. The determination that best matches the user's expectation may be set for various contexts by the user or may be learned using an AI based on past determination.

For example, the determined state from the short time interval may indicate abnormality, while the determined state from the long time interval may indicate normality. If the context indicates that the short time abnormality may be ignored, such as the case when the determined state is erroneous or is outlier information (e.g. when there is a contact failure of the device or when external but short and temporary stress is put on the user), it may be determined not to output the results to the user. In other words, in such cases, the results may be output to the user only when the determined results for the short time interval and the long time interval are the same. On the other hand, context may indicate that the short time abnormality may be important, such as when the user is sick and any short-time change in the user's state needs to be reported. In such a case, the result from the short time interval may be assigned higher weight and be output with higher priority.

Furthermore, the length of the time intervals or number of time points may change or set in accordance with the context (a scene or event) that the user is in when the measurements are made. This correspondence between the context to the length of the time intervals or the number of points may be set by the user or may be learned by an AI based on the past data.

Note, that some examples above are illustrated with respect to two time series with two time intervals (short or long), but the present embodiment is not limited, and is applicable to any number of time series.

Alternatively, a suggested intervention may be determined based on the state of the at least one user and/or the historical information, and the suggested intervention may be output to the at least one user.

Alternatively, the biological information measuring apparatus 12 may be in the form of an audible device (as discussed in below) including a sound input-output device, and the information processing apparatus 10 may output the suggested intervention to the at least one user via the sound input-output device, acquire a response of the at least one user to the suggested intervention, and store the response in the memory. The suggested intervention and the response of the at least one user may be stored as part of the historical information. In this way, determination of the suggested intervention may take into account past interventions, responses and their context when the user was in a similar or a same state or context, as well as the context that the user is currently in. The correspondence between the context to the suggested intervention may be set by the user or may be learned by an AI based on the past data.

Alternatively, before performing the suggested intervention, the information processing apparatus 10 may select a first mode in which the response is acquired from the at least one user, or a second mode in which the suggested intervention is automatically performed by artificial intelligence.

Alternatively, the intervention may be performed by an intervention device (e.g. a terminal apparatus 18) in a form or mode of communicating via at least one of light (by way of light color, light intensity, or light pulses), image, video, sound, voice, music, vibration, temperature change (hot or cold), impact (collision with an object, or throwing an object), stimulation (pinching or pulling), or smell/scent. An example in which the intervention is communicated by light is illustrated at https://www.youtube.com/watch?v=Vr8hSeAjY2I.

Other forms or modes of intervention may include an adjustment of air temperature (e.g. temperature setting on an air conditioner), an interaction with an AI (e.g. comforting, encouraging, helping or making an advice), or a comforting expression or gesture by a robot (e.g. a sound coming from a pet robot or behaviors/actions of the pet robot that are comforting).

Alternatively, the state of the at least one user may be output to at least one other user.

In the case of outputting to the at least one other user, the determination of the state of the at least one user may be performed by the information processing apparatus 10 of the at least one other user based on the biological information and the historical information of the at least one user or the at least one other user. Similarly, the suggested intervention may be performed by the intervention device shared by the at least one user and the at least one other user. Alternatively, the biological information of the at least one user may be transmitted to the at least one other user and the information processing apparatus 10 of the at least one other user may determine the intervention (or the intervention device) to be used.

When the at least one user and the at least one other user is in the same location, the same intervention device may be selected for performing the intervention. More specifically, the range of space within which the state of the at least one user is shared or the intervention device to be used can be determined based on location information of the at least one user and the at least one other user. Note that such sharing of the state of the at least one user can be determined by the type of relationship between the at least one user and the at least one other user (e.g. a relationship between a patient and a doctor, or a relationship between workers in a cooperative relationship).

The determination of the state of the at least one user or the determination of the intervention may be based on the past determination of the at least one user and the at least one other user, which adds variability to the determination done solely by relying on information of one user. Moreover, the biological information of the at least one other user may be found to be similar to or same as the biological information of the at least one user, in which case the at least one other user may be added as a candidate to whom the same intervention can be performed. In determining the intervention itself or selecting which intervention device to use, past interventions (or intervention devices) in terms of their effectiveness may be recorded in the historical information and a priority may be assigned such that the intervention (or intervention device) that had the highest effect (that has a higher priority) may be selected. Learning of which intervention (or intervention device) is effective based on past data can be done by an AI. In the case of there being a new candidate for intervention (or intervention device) or if there are plural candidates for intervention (or intervention device), the user may select from among the candidates. Alternatively, the at least one other user may select the candidate intervention (or intervention device) based on its past effectiveness on the at least one user. Alternatively, the at least one user may decide not to select the intervention (or intervention device) but permit the at least one other user to whom a permission has been given to select the intervention (or intervention device) on behalf of the at least one user, for there are cases in which selection of an intervention by others may be more effective than by oneself.

Twenty-Second Example

The information processing apparatus 10 may also be used to assist communication of at least one user.

In the twenty-second example, the biological information measuring apparatus 10 acquires biological information of at least one user. The information processing apparatus 10 determines a state of at least one user based on the biological information of the at least one user. Then, the information processing apparatus 10 assists communication of information of the at least one user based on the state of the at least one user.

Alternatively, when assisting communication of information from one user to other user, the information processing apparatus 10 may obtain confirmation from the one user to transmit the information to the other user.

Alternatively, when the one user rejects the information to be transmitted to the other user, the information may be stored in the memory associated with the one user.

Alternatively, when the one user rejects the information to be transmitted to the other user, a selection of at least one alternate action may be suggested to the one user. The alternate action may include at least one of retransmitting the information to the other user after a predetermined time period passes, transmitting the information to a different user, or abandoning transmission of the information.

Alternatively, when the one user confirms transmission of the information to the other user, the information processing apparatus 10 may store, as learned data, the information in association with the state of the one user in the memory, and use the learned data in subsequent determination of the information based on the state of the one user.

Alternatively, when the one user confirms transmission of the information to the other user, the information processing device may store data indicating whether or not the transmission to the other user was successful.

Alternatively, the information processing apparatus 10 may determine the state of the at least one user based on frequency spectrum of a bioelectrical potential measured from the at least one user.

Hearable

A hearable, which is an example of the biological information measuring apparatus 12 according to the present exemplary embodiment, will be described in detail with reference to FIGS. 29 to 37. Although earphones to be worn on a person's ears will be taken as an example of the hearable hereinafter, the hearable to be used need not be earphones.

For example, at least one electrode is used as a biopotential detection electrode (hereinafter referred to as a "sensor electrode") for detecting a potential including biopotential, and at least one electrode is used as an electrode for grounding (hereinafter referred to as a "ground electrode"). At least one electrode is used as an electrode (hereinafter referred to as a "reference electrode") for detecting a potential to be compared with the potential detected by the sensor electrode.

Figure 29:
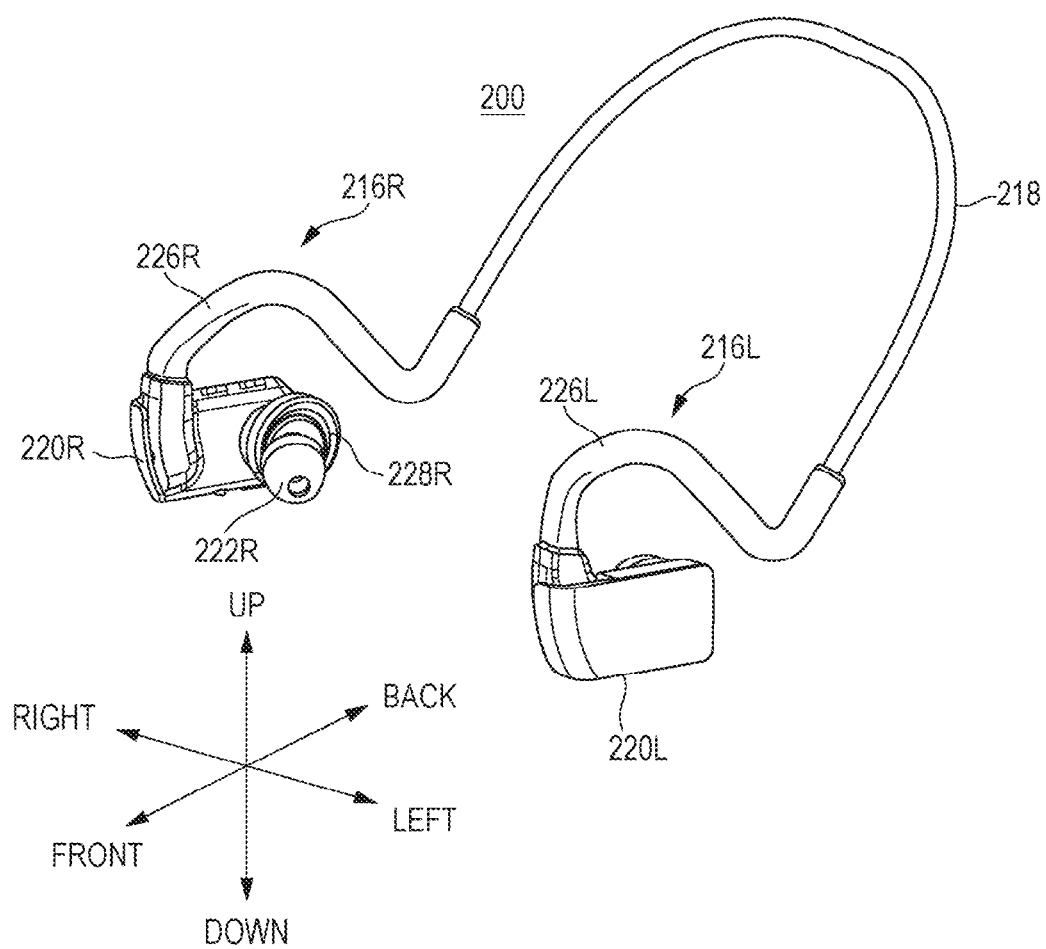
FIG. 29 is a perspective view of the entirety of a hearable.
Figure 30:
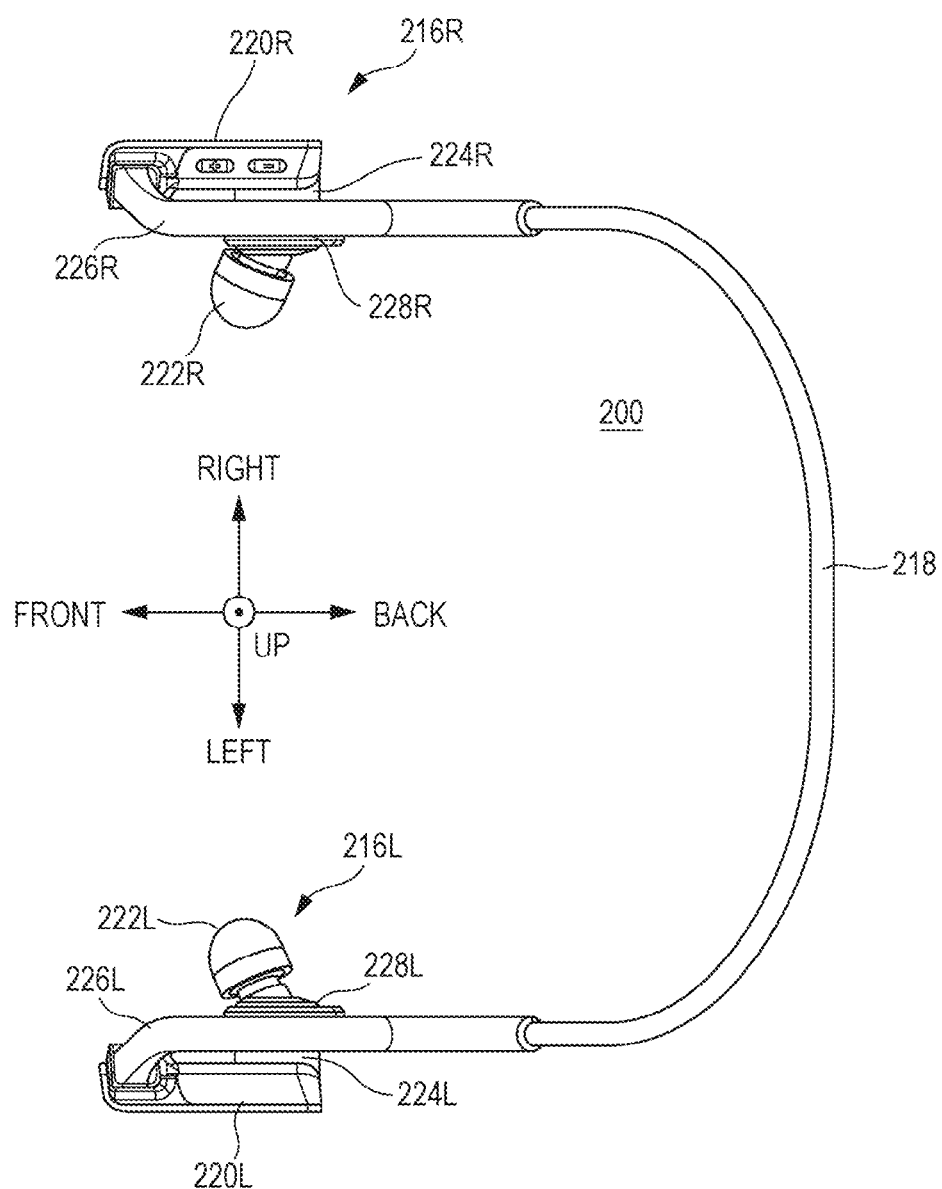
FIG. 30 is a diagram illustrating a biological information measuring apparatus viewed from above.
Figure 31:
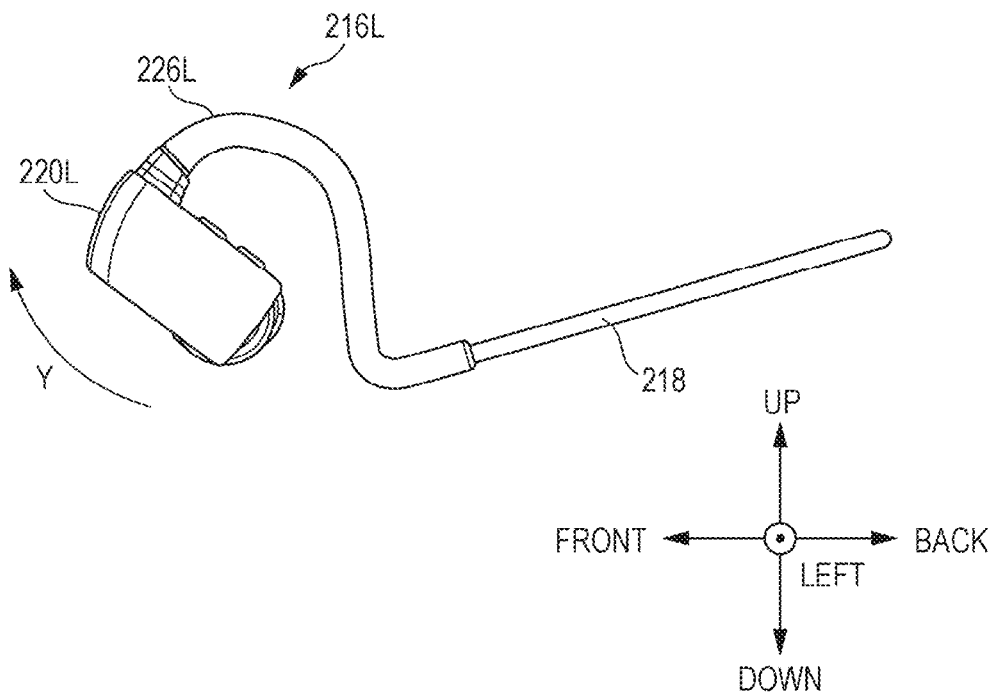
FIG. 31 is a diagram illustrating a left earphone viewed from the left.
Figure 32:
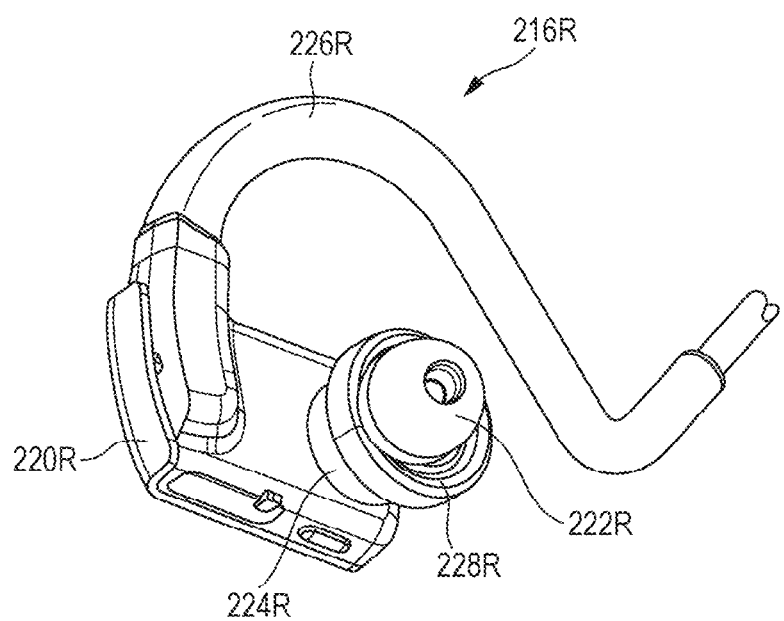
FIG. 32 is a perspective view of a right earphone.
Figure 33:
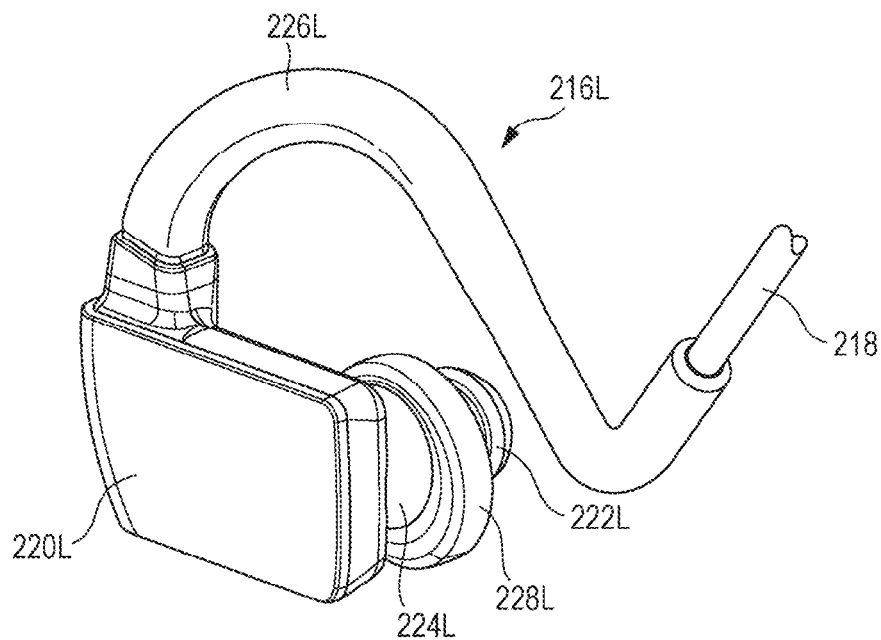
FIG. 33 is a perspective view of the left earphone.
Figure 34:
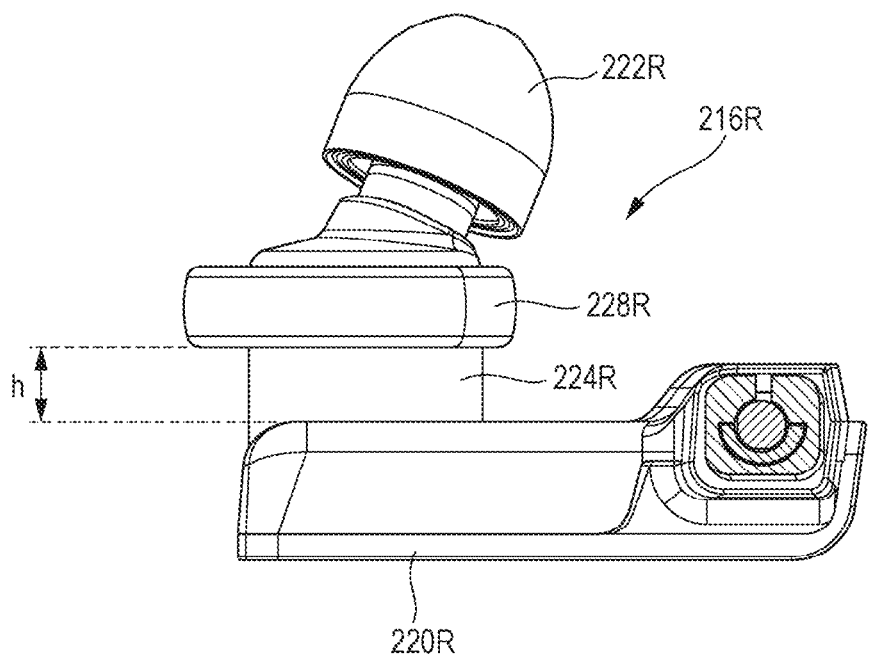
FIG. 34 is a diagram illustrating the right earphone viewed from above.
Figure 35:
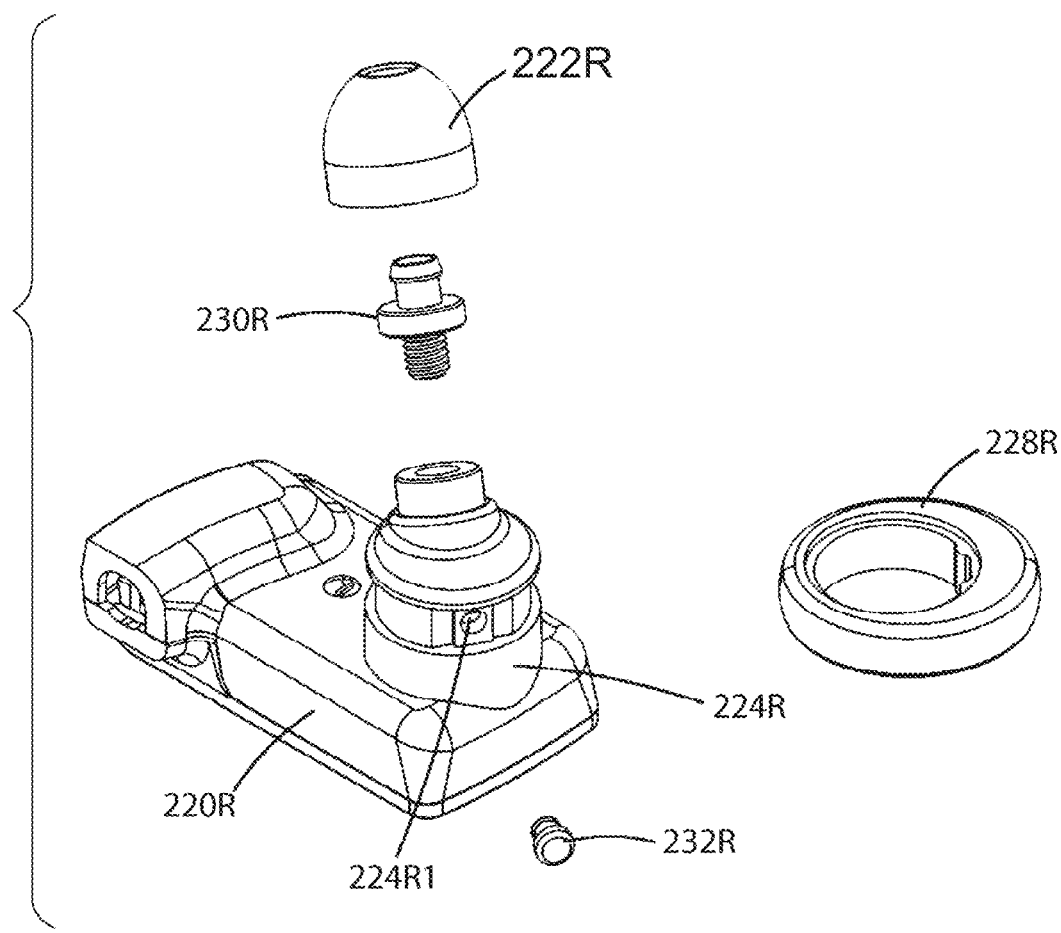
FIG. 35 is an exploded perspective view of the right earphone.
Figure 36:
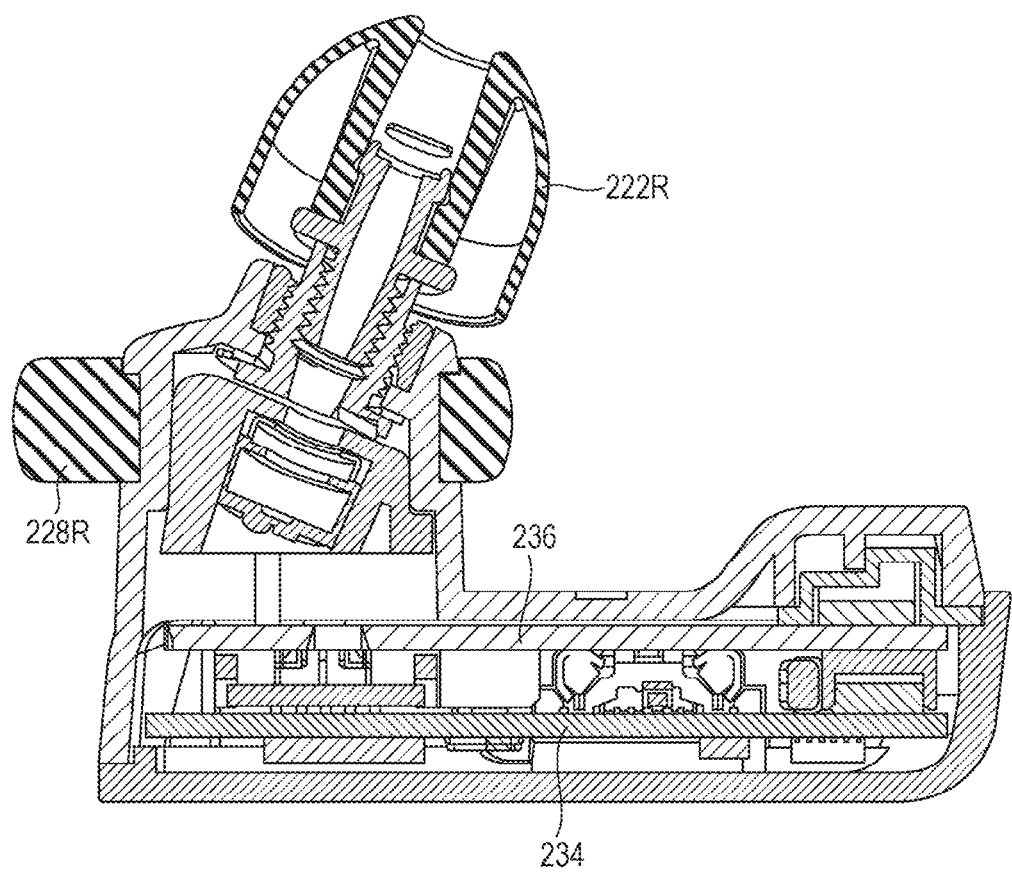
FIG. 36 is a cross-sectional view of the right earphone.
Figure 37:
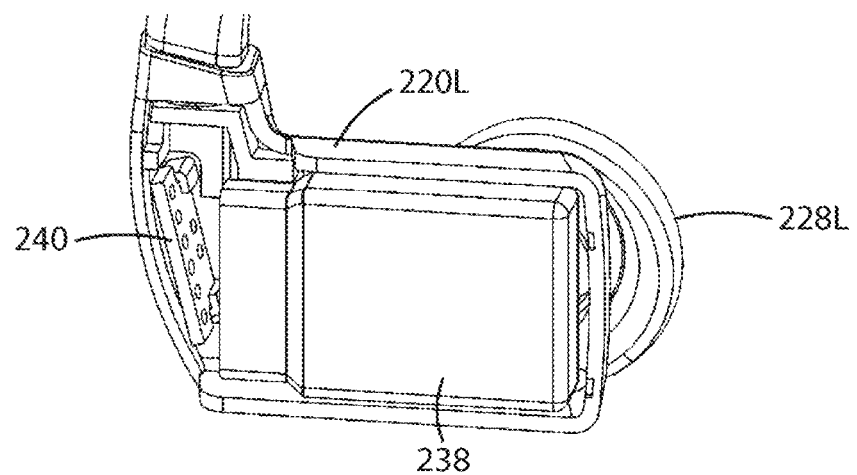
FIG. 37 is a perspective view of the inside of the left earphone.

A potential detected by the sensor electrode will be referred to as a "sensor potential", a potential detected by the reference electrode will be referred to as a "reference potential", and a potential detected by the ground electrode will be referred to as a "ground electrode" hereinafter. FIG. 29 is a perspective view of the entirety of a hearable 200. FIG. 30 is a diagram illustrating the hearable 200 viewed from above. FIG. 31 is a diagram illustrating a left earphone viewed from the left. FIG. 32 is a perspective view of a right earphone. FIG. 33 is a perspective view of the left earphone. FIG. 34 is a diagram illustrating the right earphone viewed from above. FIG. 35 is an exploded perspective view of the right earphone. FIG. 36 is a cross-sectional view of the right earphone. FIG. 37 is a perspective view illustrating the inside of the left earphone.

As illustrated in FIG. 29, front and back directions, up and down directions, and left and right directions are defined for convenience of description. The front direction is a direction in which a person's face is oriented, and the back direction is a direction opposite the front direction. The up direction is a direction in which a top of the person's head is oriented, and the down direction is a direction opposite the up direction. The right direction is a direction of the person's right hand, and the left direction is a direction of the person's left hand. The front and back directions, the up and down directions, and the left and right directions are perpendicular to one another.

It is assumed here, for example, that the hearable 200 measures biological information including brain waves. The hearable 200 may measure biological information other than brain waves in addition to, or instead of the brain waves. When a right earphone 216R and a left earphone 216L, which will be described later, are worn on a person's ears, for example, a potential indicating biological information is detected. A potential signal indicating the detected potential usually includes a potential signal indicating brain waves. In addition to the potential signal indicating brain waves, however, the potential signal might include a potential signal indicating a potential caused by movement based on a facial expression or a potential caused by movement of the neck, the jaw, or the eyes as a potential signal indicating a potential caused by movement of the person's head. In addition, cerebral blood flow, pulse waves relating to cardiac blood flow, heartbeat, or the like might be clearly measured as biological information caused by changes in blood flow due to movement of the person's head. The hearable 200 might thus measure biological information other than brain waves along with the brain waves. The biological information other than brain waves may be processed as noise (e.g., may be removed), or separated from the brain waves and used for some processes.

As illustrated in FIGS. 29 and 30, the hearable 200 roughly includes the right earphone 216R worn on the right ear, the left earphone 216L worn on the left ear, and a cable 218 for electrically connecting the right earphone 216R and the left earphone 216L to each other. The right earphone 216R and the left earphone 216L may communicate signals and data with each other through the cable 218. The cable 218 may be provided with a remote control for controlling the hearable 200.

Either the right earphone 216R or the left earphone 216L may function as a biological information measuring apparatus that measures biological information, or both the right earphone 216R and the left earphone 216L may function as biological information measuring apparatuses.

For example, one of the earphones may include the sensor electrode, the reference electrode, and the ground electrode, and the earphone need not include any electrode.

In another example, both the right earphone 216R and the left earphone 216L may include the sensor electrode, the reference electrode, and the ground electrode.

In yet another example, one of the earphones may include one or two of the sensor electrode, the reference electrode, and the ground electrode, and the other earphone may include an electrode that is not included in the foregoing earphone.

In yet another example, the right earphone 216R and the left earphone 216L may each include one or more electrodes, and the sensor electrode, the reference electrode, and the ground electrode may be distributed between the right earphone 216R and the left earphone 216L.

In yet another example, plural sensor electrodes, plural reference electrodes, and plural ground electrodes may be provided for one of the earphones. For example, plural sensor electrodes may be provided for the right earphone 216R, and plural reference electrodes may be provided for the left earphone 216L.

The right earphone 216R is a canal-type earphone, for example, and includes a right case 220R, a right earpiece 222R, a right support 224R, and a right ear hook 226R, and an electrode member 228R. The earpiece is sometimes called an "earpad".

The right case 220R has a thin rectangular parallelepiped shape, for example, and stores an electronic circuit and the like. The right earpiece 222R and the right support 224R are arranged in the right case 220R on a surface that faces the user's right ear when the user wears the hearable 200. The right case 220R stores a control device, a speaker, a communication device (e.g., a communication chip), an electronic circuit that analyzes and processes biological information, a six-axis sensor (e.g., a sensor including a three-axis sensor that detects acceleration and a three-axis sensor that detects angular velocity etc.), a memory, a GPS sensor, and the like. The communication device is a device for achieving a wireless communication function such as Bluetooth (registered trademark) or BLE. The communication device may include a wireless LAN (e.g., a network that employs Wi-Fi (registered trademark) etc.) or a cellular (3G, 4G, 5G, low-power wide-area (LPWA), etc.) module to achieve a wide communication area and directly transmit data to remote devices through local area devices whose communication distances are longer than that of Bluetooth (registered trademark) or the Internet. The six-axis sensor detects a traveling direction, orientation, and rotation of the right case 220R. Biological information may be stored in the memory. The electronic circuit that analyzes biological information need not be provided for the biological information measuring apparatus 12.

The right support 224R has a columnar shape such as a cylindrical shape and protrudes from a side (e.g., a surface that faces the user's right ear when the user wears the right earphone 216R on his/her right ear) of the right case 220R between the right case 220R and the right earpiece 222R. For example, the outer diameter of the right support 224R is larger than that of the right earpiece 222R. The electrode member 228R is provided for a part or the entirety of a side of the right support 224R.

The electrode member 228R has a ring shape, for example, and is supported by the columnar right support 224R. A part or the entirety of the electrode member 228R functions as an electrode. That is, an electrode may be provided all over a surface of the electrode member 228R, or an electrode may be provided over a part of the surface of the electrode member 228R and need not be provided over the rest of the surface. The electrode member 228R is composed, for example, of a conductive rubber made of carbon. In this case, too, the entirety (e.g., the entirety of the surface) of the electrode member 228R may be composed of the conductive rubber and function as an electrode, or a part (e.g., a part of the surface) of the electrode member 228R may be composed of the conductive rubber and function as an electrode.

The right earpiece 222R is provided at a tip of the right support 224R (i.e., an end of the right support 224R opposite an end connected to the right case 220R). For example, the right earpiece 222R has a cylindrical shape that tapers toward a tip. This shape is just an example, and the right earpiece 222R may have another shape, instead.

The right earpiece 222R stores a sound conduit (e.g., a conductive tube member that will be described later) and the like. A sound output from the speaker goes out of the right earpiece 222R through the sound conduit and the like inside the right earpiece 222R. An electrode is provided over a part or the entirety of an outer surface (e.g., a side etc.) of the right earpiece 222R. The electrode is composed, for example, of conductive rubber made of carbon. The right earpiece 222R itself may be composed of the conductive rubber, instead. For example, a part or the entirety of the right earpiece 222R may be composed of the conductive rubber. That is, a part or the entirety of the surface of the right earpiece 222R may function as an electrode.

The right earpiece 222R and the electrode member 228R may be, for example, elastic members. A resin such as rubber is used for the elastic members. More specifically, a silicone-based rubber (e.g., S1734 manufactured by NOK Corporation), a urethane-based rubber, or the like may be used for the right earpiece 222R and the electrode member 228R. The hardness of the right earpiece 222R and the electrode member 228R (e.g., hardness according to specifications of a type A durometer (instantaneous)) is, for example, 40 to 75. A resin having a hardness of 70, for example, may be used for the right earpiece 222R and the electrode member 228R.

As described later, the right earpiece 222R is arranged on the right ear in such a way as to be inserted into the right ear canal and come into contact with the right ear canal, and the electrode member 228R supported by the right support 224R is arranged on the right ear in such a way as to come into contact with the right ear cavity.

The right ear hook 226R has a curved shape as a whole and is hung on the user's right ear when the user wears the right earphone 216R. For example, the right ear hook 226R is hung on the right ear helix. More specifically, the right ear hook 226R is arranged behind the right ear helix while in contact with the right ear helix. An end of the right ear hook 226R is connected to a front part of the right case 220R. The right ear hook 226R bends from the connection with the right case 220R toward a back part of the right case 220R, thereby forming a curve. The curve is arranged behind the right ear helix while in contact with the right ear helix. For example, the curve has a shape along a shape of the back of the right ear helix. Another end of the right ear hook 226R is connected to an end of the cable 218.

The right earpiece 222R and the right support 224R are replaceable members. For example, plural (e.g., three to five each) right earpieces 222R and right supports 224R having different shapes and sizes are prepared. The right earpiece 222R and the right support 224R may be replaced in accordance with the shape of the user's right ear (e.g., the ear canal, the ear cavity, or another part).

The left earphone 216L is a canal-type earphone, for example, and includes a left case 220L, a left earpiece 222L, a left support 224L, a left ear hook 226L, and an electrode member 228L.

The left case 220L has a thin rectangular parallelepiped shape, for example, and stores a battery and the like. The left earpiece 222L and the left support 224L are arranged in the left case 220L on a surface that faces the user's left ear when the user wears the hearable 200. Power from the battery is supplied to the right earphone 216R and the left earphone 216L to drive the right earphone 216R and the left earphone 216L. For example, power from the battery is supplied to speakers and circuits. The battery may be provided for both the right case 220R and the left case 220L or either the right case 220R or the left case 220L.

The left support 224L has a columnar shape such as a cylindrical shape and protrudes from a side (e.g., a surface that faces the user's left ear when the user wears the left earphone 216L on his/her left ear) of the left case 220L between the left case 220L and the left earpiece 222L. For example, the outer diameter of the left support 224L is larger than that of the left earpiece 222L. The electrode member 228L is provided for a part or the entirety of a side of the left support 224L.

The electrode member 228L has a ring shape, for example, and is supported by the columnar left support 224L. A part or the entirety of the electrode member 228L functions as an electrode. That is, an electrode may be provided all over a surface of the electrode member 228L, or an electrode may be provided over a part of the surface of the electrode member 228L and need not be provided over the rest of the surface. The electrode member 228L is composed, for example, of a conductive rubber made of carbon. In this case, too, the entirety (e.g., the entirety of the surface) of the electrode member 228L may be composed of the conductive rubber and function as an electrode, or a part (e.g., a part of the surface) of the electrode member 228L may be composed of the conductive rubber and function as an electrode.

The left earpiece 222L is provided at a tip of the left support 224L (i.e., an end of the left support 224L opposite an end connected to the left case 220L). For example, the left earpiece 222L has a cylindrical shape that tapers toward a tip. This shape is just an example, and the left earpiece 222L may have another shape, instead.

The left earpiece 222L stores a sound conduit and the like. A sound output from the speaker goes out of the left earpiece 222L through the sound conduit and the like inside the left earpiece 222L. An electrode is provided over a part or the entirety of an outer surface (e.g., a side etc.) of the left earpiece 222L. The electrode is composed, for example, of conductive rubber made of carbon. The left earpiece 222L itself may be composed of the conductive rubber, instead. For example, a part or the entirety of the left earpiece 222L may be composed of the conductive rubber. That is, a part or the entirety of the surface of the left earpiece 222L may function as an electrode.

The left earpiece 222L and the electrode member 228L may be, for example, elastic members. A resin such as rubber is used for the elastic members. More specifically, a silicone-based rubber (e.g., S1734 manufactured by NOK Corporation), a urethane-based rubber, or the like may be used for the left earpiece 222L and the electrode member 228L. The hardness of the left earpiece 222L and the electrode member 228L (e.g., hardness according to specifications of a type A durometer (instantaneous)) is, for example, 40 to 75. A resin having a hardness of 70, for example, may be used for the left earpiece 222L and the electrode member 228L.

As described later, the left earpiece 222L is arranged on the left ear in such a way as to be inserted into the left ear canal and come into contact with the left ear canal, and the electrode member 228L supported by the left support 224L is arranged on the left ear in such a way as to come into contact with the left ear cavity.

The left ear hook 226L has a curved shape as a whole and is hung on the user's left ear when the user wears the left earphone 216L. For example, the left ear hook 226L is hung on the left ear helix. More specifically, the left ear hook 226L is arranged behind the left ear helix while in contact with the left ear helix. An end of the left ear hook 226L is connected to a front part of the left case 220L. The left ear hook 226L bends from the connection with the left case 220L toward a back part of the left case 220L, thereby forming a curve. The curve is arranged behind the left ear helix while in contact with the left ear helix. For example, the curve has a shape along a shape of the back of the ear helix. Another end of the left ear hook 226L is connected to another end of the cable 218.

The left earpiece 222L and the left support 224L are replaceable members. For example, plural (e.g., three to five each) left earpieces 222L and left supports 224L having different shapes and sizes are prepared. The left earpiece 222L and the left support 224L may be replaced in accordance with the shape of the user's left ear (e.g., the ear canal, the ear cavity, or another part).

The control device, the communication device, the electronic circuit, the six-axis sensor, the memory, and the like may be stored in either the right case 220R or the left case 220L or both the right case 220R and the left case 220L.

The right case 220R or the left case 220L is provided with a power supply button, a switch for adjusting sound volume, and the like. The power supply button, the switch, and the like may be provided for both the right case 220R and the left case 220L.

For example, either the electrode provided for the right earpiece 222R or the electrode provided for the left earpiece 222L is used as the sensor electrode, and the other electrode is used as the reference electrode. The electrode member 228R and the electrode member 228L are used as the ground electrodes. Alternatively, either the electrode member 228R or the electrode member 228L may be used as the sensor electrode, the other may be used as the reference electrode, and the electrodes provided for the right earpiece 222R and the left earpiece 222L may be used as the ground electrodes.

In another example, plural electrodes separate from one another may be provided for the right earpiece 222R, and at least one of the electrodes may be used as the sensor electrode, the reference electrode, or the ground electrode. For example, the electrodes may be used as sensor electrodes, and a potential detected by an electrode whose detection sensitivity is the highest, an electrode whose noise is the smallest, or an electrode whose level of noise is the most stable may be used as a sensor potential. The same holds when the electrodes are used as reference electrodes or ground electrodes. The same also holds for the left earpiece 222L, the electrode member 228R, and the electrode member 228L.

As illustrated in FIG. 34, the electrode member 228R supported by the right support 224R is arranged higher than the right case 220R by a height h. That is, a distance between the electrode member 228R and the right case 220R is set at the height h. The height h is set, for example, at a value with which the right case 220R and the ear helix do not interfere with each other and a contact failure does not occur. More specifically, the height h is set such that the right case 220R does not come into contact with the right ear helix when the right earpiece 222R is inserted into the right ear canal and the right earphone 216R is worn on the right ear. That is, the height h is set such that the right case 220R becomes away from the right ear helix. In doing so, for example, an upper surface of the right case 220R does not come into contact with the right ear helix. If the right case 220R comes into contact and interferes with the right ear helix, the right earpiece 222R is not inserted into the ear canal up to a position at which the right earpiece 222R becomes stable, and a contact failure might occur between the electrode of the right earpiece 222R and the ear canal. In addition, the electrode member 228R might not be arranged at a position at which the electrode member 228R has a good contact with the right ear cavity, and a contact failure might occur between the electrode member 228R and the right ear cavity. If such a contact failure occurs, detection sensitivity of sensor potential, reference potential, or ground potential might decrease, thereby decreasing measurement accuracy of biological information. By setting the height h such that the right case 220R does not come into contact with the right ear helix, the right case 220R and the right ear helix do not interfere with each other, the right earpiece 222R can be inserted into the ear canal up to the position at which the right earpiece 222R becomes stable, and the electrode of the right earpiece 222R and the right ear canal have a good contact with each other. In addition, the electrode member 228R can be arranged at the position at which the electrode member 228R has a good contact with the right ear cavity, and the electrode member 228R and the right ear cavity have a good contact with each other. In doing so, detection sensitivity of biopotential improves. The same holds for the left earphone 216L.

As illustrated in FIG. 30, when the right earphone 216R is viewed from above, the right ear hook 226R inclines from the right case 220R toward the right earpiece 222R. That is, when the right earphone 216R is viewed from above, there is a gap between the right case 220R and the right ear hook 226R. In other words, the right ear hook 226R is offset from the right case 220R toward the right earpiece 222R. The gap is for the right ear, that is, the right ear is inserted into the gap. By providing such a gap and make the user insert his/her right ear into the gap, the user's right ear can be inserted into the gap regardless of the size of the right ear, so that the right earphone 216R stays on the right ear. As a result, the electrode of the right earpiece 222R and the right ear canal have a good contact with each other, and the electrode member 228R and the right ear cavity have a good contact with each other. The same holds for the left earphone 216L.

As illustrated in FIG. 35, a conductive tube member 230R composed of a metal is provided for the right support 224R and protrudes from the right case 220R. A bottom of the conductive tube member 230R is mounted on the right support 224R, and the right earpiece 222R is arranged at a top of the conductive tube member 230R. For example, the bottom of the conductive tube member 230R is screwed into a top of the right support 224R. A conductive tube member 232R composed of a metal is provided for a side of the right support 224R and protrudes from the side. The ring electrode member 228R is also provided for the side in such a way as to cover the conductive tube member 232R. More specifically, a groove is formed in the side of the right support 224R along a circumferential direction of the right support 224R, and a hole 224R1 into which an end of the conductive tube member 232R is to be inserted is formed in the groove. When the end of the conductive tube member 232R is inserted into the hole 224R1, the conductive tube member 232R is mounted on the side of the right support 224R. For example, the conductive tube member 232R is screwed into the side of the right support 224R. The electrode member 228R is fitted into the groove in the side of the right support 224R with the conductive tube member 232R mounted on the side of the right support 224R, and the electrode member 228R is mounted on the side of the right support 224R while in contact with the conductive tube member 232R. The conductive tube member 232R is connected to electrical wire in the right support 224R. As a result, a potential signal indicating a potential detected by the electrode member 228R is transmitted to the electrical wire through the conductive tube member 232R, and then to a board 234, which will be described later. The left earphone 216L has the same configuration as the right earphone 216R.

As illustrated in FIG. 36, the right case 220R stores the board 234 and a sub-board 236. Boards other than the board 234 and the sub-board 236 may also be stored in the left case 220L. As illustrated in FIG. 37, the left case 220L stores a battery 238 and a relay board 240. The battery 238 supplies power to the right earphone 216R and the left earphone 216L through the relay board 240.

The cable 218 is hard enough to maintain an overall shape thereof. For example, the cable 218 extends from the right case 220R and the left case 220L rearward so that the cable 218 does not come into contact with the back of the user's head or hair on the back of the user's head when the hearable 200 is worn on the user's ears. Since the cable 218 does not come into contact with the back of the user's head or the hair on the back of the user's head, noise that would otherwise be caused by such a contact is not caused in biological information.

Even if the cable 218 comes into contact with the back of the user's head or the like, a load due to the contact is transmitted to the cable 218, and, as indicated by an arrow Y in FIG. 31, the entirety of the left earphone 216L rotates rearward. As a result, the left earpiece 222L and the electrode member 228L are firmly fixed by the left ear. That is, the entirety of the left earphone 216L rotates in a direction in which the left earpiece 222L and the electrode member 228L are fixed more firmly. As a result, the electrode of the left earpiece 222L and the left ear canal have a better contact with each other and the electrode member 228L and the left ear cavity have a better contact with each other, thereby improving the detection sensitivity. The same holds for the right earphone 216R.

The hearable 200 may be capable of achieving bone conduction. In this case, information can be transmitted to the user through bone conduction, not by sound. Even in the case of a deaf user, therefore, biological information regarding brain waves can be measured and information can be transmitted through bone conduction using the hearable 200.

The above-described examples may be implemented using the hearable 200, instead. That is, biological information regarding the user may be measured using the hearable 200, and the examples may be implemented using the measured biological information. Plural types of biological information may be measured using the hearable 200 and a biological information measuring apparatus 12, and a state of a person (e.g., emotion information, mental information, psychological information, etc.) may be obtained on the basis of the measured types of biological information, instead.

In the embodiments above, the term "processor" refers to hardware in a broad sense. Examples of the processor include general processors (e.g., CPU: Central Processing Unit) and dedicated processors (e.g., GPU: Graphics Processing Unit, ASIC: Application Specific Integrated Circuit, FPGA: Field Programmable Gate Array, and programmable logic device).

In the embodiments above, the term "processor" is broad enough to encompass one processor or plural processors in collaboration which are located physically apart from each other but may work cooperatively. The order of operations of the processor is not limited to one described in the embodiments above, and may be changed.

The foregoing description of the exemplary embodiments of the present disclosure has been provided for the purposes of illustration and description. It is not intended to be exhaustive or to limit the disclosure to the precise forms disclosed. Obviously, many modifications and variations will be apparent to practitioners skilled in the art. The embodiments were chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. An information processing method comprising:
by a processor:
acquiring biological information of at least one user;
based on a determination result from an artificial intelligence, which is input with biological information of the at least one user and context information indicating a context associated with information related to a time at which measurement of the biological information is made, output information that aims to change a state of the at least one user in a real world.

2. The information processing method according to claim 1, wherein a priority of the output information is changed based on historical data corresponding to the output information outputted in a past.

3. The information processing method according to claim 1, wherein the processor is configured to execute the information processing method under either:
(i) a first mode in which, if the output information is to be sent to an external device, before the output information is sent to the external device, the at least one user is inquired for permission of sending of the output information; or (ii) a second mode in which the output information is sent to the external device without inquiring the at least one user for permission of sending of the output information.

4. The information processing method according to claim 1, wherein a result after outputting the output information is stored in memory as a training data for the artificial intelligence.

* * * * *